United States Patent [19]
Gallatin et al.

[11] Patent Number: 5,470,953
[45] Date of Patent: Nov. 28, 1995

[54] HUMAN $\beta_2$ INTEGRIN $\alpha$ SUBUNIT

[75] Inventors: W. Michael Gallatin; Monica Van der Vieren, both of Seattle, Wash.

[73] Assignee: ICOS Corporation, Bothell, Wash.

[21] Appl. No.: 286,889

[22] Filed: Aug. 5, 1994

Related U.S. Application Data

[63] Continuation-in-part of Ser. No. 173,497, Dec. 23, 1993.
[51] Int. Cl.$^6$ .............................. C07K 1/00; C07K 2/00; C07H 19/00; C07H 21/00
[52] U.S. Cl. ...................... 530/350; 536/22.1; 536/23.1; 536/23.4; 536/23.5
[58] Field of Search ................................ 530/350, 380; 536/22.1, 23.1, 23.4, 23.5

[56] References Cited

U.S. PATENT DOCUMENTS

| | | | |
|---|---|---|---|
| 4,271,139 | 6/1981 | Hart | 424/1 |
| 4,568,649 | 2/1986 | Bertoglio-Matte | 436/534 |

FOREIGN PATENT DOCUMENTS

WO94/17100  9/1994  WIPO.

OTHER PUBLICATIONS

Arfors, et al., "A monoclonal antibody to the membrane glycoprotein complex CD18 inhibits polymorphonuclear leukocyte accumulation and plasma leakage in vivo," *Blood* 69:338–340 (1987).
Arnaout, "Structure and function of the leukocyte adhesion molecules CD11/CD18," *Blood* 75:1037–1050 (1990).
Burnett, et al., "The IgA heavy-chain gene family in rabbit: cloning and sequence analysis of 13 C$\alpha$ genes," EMBO J. 8:4041–4047 (1989).
Capecchi, "Altering the genome by homologous recombination, "*Science* 244:1288–1292 (1989).
Chisaka, et al., "Developmental defects of the ear, cranial nerves and hindbrain resulting from targeted disruption of the mouse homeobox gene Hox-1.6," *Nature* 355–516–520 (1992).
Corbi, et al., "The human leukocyte adhesion glycoprotein Mac-1 (complement receptor type 3, CD11b) $\alpha$ subunit," *J. Biol. Chem.* 263:12403–12411 (1988).
Corbi, et al., "cDNA cloning and complete primary structure of the $\alpha$ subunit of a leukocyte adhesion glycoprotein, p150,95," EMBO J. 6:4023–4028 (1987).
Danilenko, et al., "Canine leukocyte cell adhesion molecules (LeuCAMs): Characterization of the CD11/CE18 family," *Tissue Antigens* 40:13–21 (1992).
Diamond, et al. "The I domain is a major recognition site on the leukocyte integrin Mac-1 (CD11b/CD18) for four distrinct adhesion ligands," J. Cell. Biol. 120:1031–1043 (1993).
Fleming, et al., "Structural analysis of the CD11b gene and phylogenetic analysis of the $\alpha$–integrin gene family demonstrate remarkable conservation of genomic organization and suggest early diversification during evolution[1]," J. Immunol. ; 150:480–490 (1993).
Frohman, "Race: rapid amplification of cDNA ends," in PCR *Protocols*, pp. 28–38 (1990).
Greve, et al., "The major human rhinovirus receptor is ICAM-1," *Cell* 56:839–847 (1989).
Hanenberg, et al., "Macrophage infiltration precedes and is a prerequisite for lymphocytic insulitis in pancreatic islets of pre–diabetic BB rats," *Diabetologia* 32:126–134 (1989).
Hart and Greenwald, "Scintillation–proximity assay of antigen–antibody binding kinetics: consice communication," *J. Nuc. Med.* 20:1062–1065 (1979).
Hart and Greenwald, "Scintillation proximity assay (SPA)–a new method of immunoassay," *Mol. Immunol.* 12:265–267 (1979).
Hildreth and Orentas, "Involvement of a leukocyte adhesion receptor (LFA–1) in HIV–induced syncytium formation," *Science* 244:1075–1078 (1989).
Hynes, "Integrins: versatility, modulation, and signaling in cell adhesion," *Cell* 69:11–25 (1992).
Karin and Richards, "Human metallothionein genes–primary structure of the metallothionein–II gene and a related processed gene," *Nature* 299:797–802 (1982).
Kishimoto, et al., "Cloning of the $\beta$ subunit of the leukocyte adhesion proteins: homology to an extracellular matrix receptor defines a novel supergene family," *Cell* 48:681–690 (1987).
Kishimoto, et al., "Heterogeneous mutations in the $\beta$ subunit common to the LFA–1, Mac–1 and p150,95 glycoproteins cause leukocyte adhesion deficiency," *Cell* 50:193–202 (1987).
Landis, et al., "A novel LFA–1 activation epitope maps to the I domain," *J. Cell. Biol.* 120:1519–1527 (1993).
Larson, et al., "Primary structure of the leukocyte function–associated molecule–1, $\alpha$ subunit: an integrin with an embedded domain defining a protein superfamily," *J. Cell Biol.* 108:703–712 (1989).
Larson and Springer, "Structure and function of leukocyte integrins," *Immunol. Rev.* 114:181–217 (1990).
Letvin, et al., "Conservation of myeloid surface antigens on primate granulocytes," *Blood* 61:408–410 (1983).
McCabe, "Production of single–stranded DNA by asymmetric PCR," in PCR *Protocols*, pp. 76–83 (1990).
Metlay, et al., "The distinct leukocyte integrins of mouse spleen dendritic cells as identified with new hamster monoclonal antibodies," *J. Exp. Med.* 171:1753–1771 (1990).
Michishita, et al., "A novel divalent cation–binding site in the A domain of the $\beta$2 Integrin CR3 (CD11b/CD18) is essential for ligand binding," *Cell* 72:857–867 (1993).

(List continued on next page.)

Primary Examiner—Robert A. Wax
Assistant Examiner—Hyosuk Kim
Attorney, Agent, or Firm—Marshall, O'Toole, Gerstein, Murray & Borun

[57] ABSTRACT

DNA encoding a novel human $\beta_2$ integrin $\alpha$ subunit polypeptide, designated $\alpha_d$, is disclosed along with methods and materials for production of the same by recombinant procedures. Binding molecules specific for $\alpha_d$ are also disclosed as useful for modulating the biological activities of $\alpha_d$. DNA from other species which show homology to human $\alpha_d$ encoding sequences are also disclosed.

5 Claims, 4 Drawing Sheets

OTHER PUBLICATIONS

Moore, et al., "Canine leukocyte integrins: characterization of a CD18 homologue," *Tissue antigens* 36:211–220 (1990).

Nourshargh, et al., "Accumulation of $^{111}$In–neutrophils in rabit skin in allergic and non–allergic inflammatory reactions in vivo," *J. Immunol.* 142:3193–3198 (1989).

Patarroyo, et al., "Leukocyte–cell adhesion: A molecular process fundamental in leukocyte physiology," *Immunol. Rev.* 114:67–108 (1990).

Price, et al., "In vivo inhibition of neutrophil function in the rabbit using monoclonal antibody to CD18[1]," *J. Immunol.* 139:4174–4177 (1987).

Randi and Hogg, "I domain of $\beta_2$ Integrin lymphocyte function–associated antigen–1 contains a binding site for ligand intercellular adhesion molecule–1*," *J. Bio. Chem.* 269:12395–12398 (1994).

Rojiani, et al., "In vitro interaction of a polypeptide homologous to human Ro/SS–A antigen (calreticulin) with a highly conserved amino acid sequence in the cytoplasmic domain of integrin $\alpha$ subunits†," *Biochemistry* 30:9859–9866 (1991).

Sambrook, et al., "Immobilization of Bacteriophage $\lambda$ Plaques on Nitrocellulose Filters or Nylon Membranes" *Molecular Cloning:* p. 2.110 (1989).

Sanchez–Madrid, et al., "A Human leukocyte differentiation antigen family with distinct $\alpha$–subunits and a common $\beta$–subunit," *J. Exp. Med.* 158:1785–1803 (1985).

Schneiderman, et al., "Expression of 12 rabbit IgA $C_\alpha$ genes as chimeric rabbit–mouse IgA antibodies," *P.N.A.S(USA)* 86:7521–7565 (1989).

Searle, et al., "Regulation, linkage, and sequence of mouse metallothionein I and II genes," *Mol. Cell. Biol.* 4:1221–1230 (1984).

Shaw et al., "Molecular cloning of the human mucosal lymphocyte integrin $\alpha^E$ subunit," *J. Biol. Chem.* 269:6016–6025 (1994).

Smith, et al., "Interactions of LFA–1 and Mac–1 with intercellular adhesion facilitating adherence and transendothelial migration trophils in vitro," *J. Clin. Invest.* 83:2008–2017 (1989).

Springer, "Adhesion receptors of the immune system," *Nature* 346:425–434 (1990).

Tamura, et al., "Epithelial integrin $\alpha_6 \beta_4$: Complete primary structure of $\alpha_6$ and variant forms of $\beta_4$," *J. Cell. Biol.* 111:1593–1604 (1990).

Varshney, et al., "Structure, organization, and regulation of human metallothionein $I_F$ Gene: differential and cell–type–specific expression in response to heavy metals and glucocorticoids," *Mol. Cel. Biol.* 6:26–37 (1986).

| | | | | | | |
|---|---|---|---|---|---|---|
| αD   | TF-GT--VLL | LSVLASYHGF | NLDVEEPTIF | QEDAGGFGQS | VVQFGGSRLV | 47 |
| CD11B | MA-LR--VLL | LTALTLCHGF | NLDTENAMTF | QENARGFGQS | VVQLQGSRVV | 47 |
| CD11C | MTRTRAALLL | FTALATSLGF | NLDTEELTAF | RVDSAGFGDS | VVQYANSWVV | 50 |
| αD   | VGAPLEVVAA | NQTGRLYDCA | AATGMCQPIP | LHIRPEAVNM | SLGLTLAAST | 97 |
| CD11B | VGAPQEIVAA | NQRGSLYQCD | YSTGSCEPIR | LQVPVEAVNM | SLGLSLAATT | 97 |
| CD11C | VGAPQKIIAA | NQIGGLYQCG | YSTGACEPIG | LQVPPEAVNM | SLGLSLASTT | 100 |
| αD   | NGSRLLACGP | TLHRVCGENS | YSKGSCLLLG | SR-WEIIQTV | PDATPECPHQ | 146 |
| CD11B | SPPQLLACGP | TVHQTCSENT | YVKGLCFLFG | SNLRQQPQKF | PEALRGCPQE | 147 |
| CD11C | SPSQLLACGP | TVHHECGRNM | YLTGLCFLLG | PT--QLTQRL | PVSRQECPRQ | 148 |
| αD   | EMDIVFLIDG | SGSIDQNDFN | QMKGFVQAVM | GQFEGTDTLF | ALMQYSNLLK | 196 |
| CD11B | DSDIAFLIDG | SGSIIPHDFR | RMKEFVSTVM | EQLKKSKTLF | SLMQYSEEFR | 197 |
| CD11C | EQDIVFLIDG | SGSISSRNFA | TMMNFVRAVI | SQFQRPSTQF | SLMQFSNKFQ | 198 |
| αD   | IHFTFTQFRT | SPSQQSLVDP | IVQLKGLTFT | ATGILTVVTQ | LFHHKNGARK | 246 |
| CD11B | IHFTFKEFQN | NPNPRSLVKP | ITQLLGRTHT | ATGIRKVVRE | LFNITNGARK | 247 |
| CD11C | THFTFEEFRR | TSNPLSLLAS | VHQLQGFTYT | ATAIQNVVHR | LFHASYGARR | 248 |
| αD   | SAKKILIVIT | DGQKYKDPLE | YSDVIPQAEK | AGIIRYAIGV | GHAFQGPTAR | 296 |
| CD11B | NAFKILVVIT | DGEKFGDPLG | YEDVIPEADR | EGVIRYVIGV | GDAFRSEKSR | 297 |
| CD11C | DAIKILIVIT | DGKKEGDSLD | YKDVIPMADA | AGIIRYAIGV | GLAFQNRNSW | 298 |

FIGURE 1A

|       |            |            |            |            |            |     |
|-------|------------|------------|------------|------------|------------|-----|
| αD    | QELNTISSAP | PQDHVFKVDN | FAALGSIQKQ | LQEKIYAVEG | TQSRASSSFQ | 346 |
| CD11B | QELNTIASKP | PRDHVFQVNN | FEALKTIQNQ | LREKIFAIEG | TQTGSSSSFE | 347 |
| CD11C | KELNDIASKP | SQEHIFKVED | FDALKDIQNQ | LKEKIFAIEG | TETISSSSFE | 348 |
|       |            |            |            |            |            |     |
| αD    | HEMSQEGFST | ALTMDGLFLG | AVGSFSWSGG | AFLYPPNMSP | TFINMSQENV | 396 |
| CD11B | HEMSQEGFSA | AITSNGPLLS | TVGSYDWAGG | VFLYTSKEKS | TFINMTRVDS | 397 |
| CD11C | LEMAQEGFSA | VFTPDGPVLG | AVGSFTWSGG | AFLYPPNMSP | TFINMSQENV | 398 |
|       |            |            |            |            |            |     |
| αD    | DMRDSYLGYS | TELALWKGVQ | NLVLGAPRYQ | HTGKAVIFTQ | VSRQWRKKAE | 446 |
| CD11B | DMNDAYLGYA | AAIILRNRVQ | SLVLGAPRYQ | HIGLVAMFRQ | NTGMWESNAN | 447 |
| CD11C | DMRDSYLGYS | TELALWKGVQ | SLVLGAPRYQ | HIGKAVIFIQ | VSRQWRMKAE | 448 |
|       |            |            |            |            |            |     |
| αD    | VTGTQIGSYF | GASLCSVDVD | SDGSTDLILI | GAPHYYEQTR | GGQVSVCPLP | 496 |
| CD11B | VKGTQIGAYF | GASLCSVDVD | SNGSTDLVLI | GAPHYYEQTR | GGQVSVCPLP | 497 |
| CD11C | VIGTQIGSYF | GASLCSVDVD | TDGSTDLVLI | GAPHYYEQTR | GGQVSVCPLP | 498 |
|       |            |            |            |            |            |     |
| αD    | RGQRVQWQCD | AVLRGEQGHP | WGRFGAALTV | LGDVNEDKLI | DVAIGAPGEQ | 546 |
| CD11B | RGQRARWQCD | AVLYGEQGQP | WGRFGAALTV | LGDVNGDKLT | DVAIGAPGEE | 547 |
| CD11C | RGWRRWW-CD | AVLYGEQGHP | WGRFGAALTV | LGDVNGDKLT | DVVIGAPGEE | 547 |
|       |            |            |            |            |            |     |
| αD    | ENRGAVYLFH | GASESGISPS | HSQRIASSQL | SPRLQYFGQA | LSGGQDLTQD | 596 |
| CD11B | DNRGAVYLFH | GTSGSGISPS | HSQRIAGSKL | SPRLQYFGQS | LSGGQDLTMD | 597 |
| CD11C | ENRGAVYLFH | GVLGPSISPS | HSQRIAGSQL | SSRLQYFGQA | LSGGQDLTQD | 597 |

FIGURE 1B

```
αD    GLMDLAVGAR GQVLLLRSLP VLKVGVAMRF SPVEVAKAVY RCWEEKPSAL   646
CD11b GLVDLTVGAQ GHVLLLLRSQP VLRVKAIMEF NPREVARNVF ECNDQVVKGK  647
CD11c GLVDLAVGAR GQVLLLRTRP VLWVGVSMQF IPAEIPRSAF ECREQVSEQ    647

αD    EAGDATVCLT IQKSSLDQL- -GDIQSSVRF DLALDPGRLT SRAIFNETKN   694
CD11b EAGEVRVCLH VQKSTRDRLR EGQIQSVVTY DLALDSGRPH SRAVFNETKN   697
CD11c TLVQSNICLY IDKRSKNLLG SRDLQSSVTL DLALAPGRLS PRAIFQETKN   697

αD    PTLTTRKTLG LGIHCETLKL LLPDCVEDVV SPIILHLNFS LVREPIPSPQ   744
CD11b STRRQTQVLG LTQTCETLKL QLPNCIEDPV SPIVLRLNFS LVGTPLSAFG   747
CD11c RSLSRVRVLG LKAHCENFNL LLPSCVEDSV IPIILRLNFT LVGKPLLAFR   747

αD    NLRPVLAVGS QDLFTASLPF EKNCGQDGLC EGDLGVTLSF SGLQTLTVGS   794
CD11b NLRPVLAEDA QRLFTALFPF EKNCGNDNIC QDDLSITFSF MSLDCLVVGG   797
CD11c NLRPMLAALA QRYFTASLPF EKNCGADHIC QDNLGISFSF PGLKSLLVGS   797

αD    SLELNVIVTV WNAGEDSYGT VVSLYYPAGL SHRRVSGAQK QPHQSALRLA   844
CD11b PREFNVTVTV RNDGEDSYRT QVTFFFPLDL SYRKVSTLQN QRSQRSWRLA   847
CD11c NLELNAEVMV WNDGEDSYGT TITFSHPAGL SYRYVAEGQK QGQLRSLHLT   847

αD    CETVPTED-- EGLRSSRCSV NHPIFHEGSN GTFIVTFDVS Y---KATLG    888
CD11b CESASSTEVS GALKSTSCSI NHPIFPENSE ----VTFNIT FDVDSKASLG   893
CD11c CCSA-PVGSQ GTW-STSCRI NHLIFRGGAQ ----ITFLAT FDVSPKAVGL   891
```

FIGURE 1C

```
αD    DRMLMRASAS SENNKASSSK ATFQLELPVK YAVYTMISRQ EESTKYFNFA    938
CD11B NKLLLKANVT SENNMPRTNK TEFQLELPVK YAVYMVTSH  GVSTKYLNFT   943
CD11C DRLLLIANVS SENNIPRTSK TIFQLELPVK YAVYIVVSSH EQFTKYLNFS    941

αD    TS-DEKKMKE AEHRYRVNNL SQRDLAISIN FWVPVLLNGV AVWDVVMEAP    987
CD11B AS-ENTS-RV MQHQYQVSNL GQRSLPISLV FLVPVRLNQT VIWDRPQVTF    991
CD11C ESEEKES-HV AMHRYQVNNL GQRDLPVSIN FWVPVELNQE AVWMDVEVSH    990

αD    SQSLP--CVS ERKPPQHSDF LTQISRSPML DCSIADCLQF RCDVPSFSVQ   1035
CD11B SENLSSTCHT KERLPSHSDF LAELRKAPVV NCSIAVCQRI QCDIPFFGIQ   1041
CD11C PQNPSLRCSS EKIAPPASDF LAHIQKNPVL DCSIAGCLRF RCDVPSFSVQ   1040

αD    EELDFTLKGN LSFGWRETL  QKKVLVVSVA EITFDTSVYS QLPGQEAFMR   1085
CD11B EEFNATLKGN LSFDWYIKTS HNHLLIVSTA EILFNDSVFT LLPGQGAFVR   1091
CD11C EELDFTLKGN LSFGWVRQIL QKKVSVVSVA EIIFDTSVYS QLPGQEAFMR   1090

αD    AQMEMVLEED EVYNAIPIIM GSSVGALLLL ALITATLYKL GFFKRHYKEM   1135
CD11B SQTETKVEPF EVPNPLPLIV GSSVGGLLLL ALITAALYKL GFFKRQYKDM   1141
CD11C AQTITVLEKY KVHNPIPLIV GSSIGGLLLL ALITAVLYKV GFFKRQYKEM   1140

αD    LEDKPED--- ------TATFS GDDFSCVAPN VPLS                   1161
CD11B SEG---     ----GP--P  GAE-----PQ ----                   1153
CD11C M---EEANGQ IAPENGT--Q TPS-----PP SEK                    1163
```

FIGURE 1D

HUMAN β₂ INTEGRIN α SUBUNIT

This application is a continuation-in-part of U.S. application Ser. No. 08/173,497, filed Dec. 23, 1993, which is allowed.

FIELD OF THE INVENTION

The present invention relates to the cloning and expression of nucleotide sequences encoding a novel human $\beta_2$ integrin $\alpha$ subunit, designated $\alpha_d$, which is structurally related to the known human $\beta_2$ integrin $\alpha$ subunits, CD11a, CD11b and CD11c. The present invention also relates to nucleotide sequences isolated other species which show homology to human $\alpha_d$ encoding sequences.

BACKGROUND OF THE INVENTION

The integrins are a class of membrane-associated molecules which actively participate in cellular adhesion. Integrins are transmembrane heterodimers comprising an $\alpha$ subunit in noncovalent association with a $\beta$ subunit. To date, at least fourteen $\alpha$ subunits and eight $\beta$ subunits have been identified [reviewed in Springer, *Nature* 346:425–434 (1990)]. The $\beta$ subunits are generally capable of association with more than one $\alpha$ subunit and the heterodimers sharing a common $\beta$ subunit have been classified as subfamilies within the integrin population.

One class of human integrins, restricted to expression in white blood cells, is characterized by a common $\beta_2$ subunit. As a result of this cell-specific expression, these integrins are commonly referred to as the leukocyte integrins, Leu-CAMs or leukointegrins. Because of the common $\beta_2$ subunit, an alternative designation of this class is the $\beta_2$ integrins. The $\beta_2$ subunit (CD18) has previously been isolated in association with one of three distinct $\alpha$ subunits, CD11a, CD11b or CD11c. The isolation of a cDNA encoding human CD18 is described in Kishimoto, et al., *Cell* 48:681–690 (1987). In official WHO nomenclature, the heterodimeric proteins are referred to as CD11a/CD18, CD11b/CD18, and CD11c/CD18; in common nomenclature they are referred to as LFA-1, Mac-1 or Mo1 and p150,95 or LeuM5, respectively [Cobbold, et al., in *Leukocyte Typing III*, McMichael (ed), Oxford Press, p.788 (1987)]. The human $\beta_2$ integrin $\alpha$ subunits CD11a, CD11b and CD11c have been demonstrated to migrate under reducing condition in electrophoresis with apparent molecular weights of approximately 180 kD, 155 kD and 150 kD, respectively, and DNAs encoding these subunits have been cloned [CD11a, Larson, et al., *J. Cell Biol.* 108:703–712 (1989); CD11b, Corbi, et al., *J. Biol. Chem.* 263:12403–12411 (1988) and CD11c, Corbi, et al. *EMBO J.* 6:4023–4028 (1987)]. Putative homologs of the human $\beta_2$ integrin $\alpha$ and $\beta$ chains, defined by approximate similarity in molecular weight, have been variously identified in other species including monkeys and other primates [Letvin, et al., *Blood* 61:408–410 (1983)], mice [Sanchez-Madrid, et al., *J. Exp. Med.* 154:1517 (1981)], and dogs [Moore, et al., *Tissue Antigens* 36:211–220 (1990)].

The absolute molecular weights of presumed homologs from other species have been shown to vary significantly [see, e.g., Danilenko et al., *Tissue Antigens* 40:13–21 (1992)], and in the absence of sequence information, a definitive correlation between human integrin subunits and those identified in other species has not been possible. Moreover, variation in the number of members in a protein family has been observed between different species. Consider, for example, that more IgA isotypes have been isolated in rabbits than in humans [Burnett, et al., *EMBO J.* 8:4041–4047 (1989) and Schneiderman, et al., *Proc. Natl. Acad. Sci.(USA)* 86:7561–7565 (1989)]. Similarly, in humans, at least six variants of the metallothionine protein have been previously identified [Karin and Richards, *Nature* 299:797–802 (1982) and Varshney, et al., *Mol. Cell. Biol.* 6:26–37, (1986)], whereas in the mouse, only two such variants are in evidence [Searle, et al., *Mol. Cell. Biol.* 4:1221–1230 (1984)]. Therefore, existence of multiple members of a protein family in one species does not necessarily imply that corresponding family members exist in another species.

In the specific context of $\beta_2$ integrins, in dogs it has been observed that the presumed canine $\beta_2$ counterpart to the human CD18 is capable of dimer formation with as many as four potentially distinct $\alpha$ subunits [Danilenko, et al., supra]. Antibodies generated by immunizing mice with canine splenocytes resulted in monoclonal antibodies which immunoprecipitated proteins tentatively designated as canine homologs to human CD18, CD11a, CD11b and CD11c based mainly on similar, but not identical, molecular weights. Another anti-canine splenocyte antibody, Ca11.8H2, recognized and immunoprecipitated a fourth $\alpha$-like canine subunit also capable of association with the $\beta_2$ subunit, but having a unique molecular weight and restricted in expression to a subset of differentiated tissue macrophages. Antibodies generated by immunization of hamsters with murine dendritic cells resulted in two anti-integrin antibodies [Metlay, et al., *J. Exp. Med.* 171:1753–1771 (1990)]. One antibody, 2E6, immunoprecipitated a predominant heterodimer with subunits having approximate molecular weights of 180 kD and 90 kD in addition to minor bands in the molecular weight range of 150–160 kD. The second antibody, N418, precipitated another apparent heterodimer with subunits having approximate molecular weights of 150 kD and 90 Kd. Based on cellular adhesion blocking studies, it was hypothesized that antibody 2E6 recognized a murine counterpart to human CD18. While the molecular weight of the N418 antigen suggested recognition of a murine homolog to human CD11c/CD18, further analysis indicated that the murine antigen exhibited a tissue distribution pattern which was inconsistent with that observed for human CD11c/CD18.

The antigens recognized by the canine Ca11.8H2 antibody and the murine N418 antibody could represent a variant species (e.g., a glycosylation or splice variant) of a previously identified canine or murine $\alpha$ subunit. Alternatively, these antigens may represent unique canine and murine integrin $\alpha$ subunits. In the absence of specific information regarding primary structure, these alternatives cannot be distinguished.

In humans, CD11a/CD18 is expressed on all leukocytes. CD11b/CD18 and CD11c/CD18 are essentially restricted to expression on monocytes, granulocytes, macrophages and natural killer (NK) cells, but CD11c/CD18 is also detected on some B-cell types. In general, CD11a/CD18 predominates on lymphocytes, CD11b/CD18 on granulocytes and CD11c/CD18 on macrophages [see review, Arnaout, *Blood* 75:1037–1050 (1990)]. Expression of the $\alpha$ chains, however, is variable with regard to the state of activation and differentiation of the individual cell types [See review, Larson and Springer, *Immunol. Rev.* 114:181–217 (1990).]

The involvement of the $\beta_2$ integrins in human immune and inflammatory responses has been demonstrated using monoclonal antibodies which are capable of blocking $\beta_2$ integrin-associated cell adhesion. For example, Cd11a/CD18, CD11b/CD18 and CD11c/CD18 actively participate in natural killer (NK) cell binding to lymphoma and adenocarcinoma cells [Patarroyo, et al., *J. Immunol. Rev.* 114:67–108 (1990)], granulocyte accumulation [Nourshargh, et al., *J. Immunol.* 142:3193–3198 (1989)], granulocyte-independent plasma leakage [Arfors, et al., *Blood* 69:338–340 (1987)], chemotactic response of stimulated leukocytes [Arfors, et al., supra] and leukocyte adhesion to vascular endothelium [Price, et al., *J. Immunol.* 139:4174–4177 (1987) and Smith, et al., *J. Clin. Invest.* 83:2008–2017 (1989)]. The fundamental role of $\beta_2$ integrins in immune and inflammatory responses is made apparent in the clinical syndrome referred to as leukocyte adhesion deficiency (LAD), wherein clinical manifestations include recurrent and often life threatening bacterial infections. LAD results from heterogeneous mutations in the $\beta_2$ subunit [Kishimoto, et al., Cell 50:193–202 (1987)] and the severity of the disease state is proportional to the degree of the deficiency in $\beta_2$ subunit expression. Formation of the complete integrin heterodimer is impaired by the $\beta_2$ mutation [Kishimoto, et al., supra].

Interestingly, at least one antibody specific for CD18 has been shown to inhibit human immunodeficiency virus type-1 (HIV-1) syncytia formation in vitro, albeit the exact mechanism of this inhibition is unclear [Hildreth and Orentas, *Science* 244:1075–1078 (1989)]. This observation is consistent with the discovery that a principal counterreceptor of CD11a/CD18, ICAM-1, is also a surface receptor for the major group of rhinovirus serotypes [Greve, et al., *Cell* 56:839 (1989)].

The significance of $\beta_2$ integrin binding activity in human immune and inflammatory responses underscores the necessity to develop a more complete understanding of this class of surface proteins. Identification of yet unknown members of this subfamily, as well as their counterreceptors, and the generation of monoclonal antibodies or other soluble factors which can alter biological activity of the $\beta_2$ integrins will provide practical means for therapeutic intervention in $\beta_2$ integrin-related immune and inflammatory responses.

BRIEF DESCRIPTION OF THE INVENTION

In one aspect, the present invention provides novel purified and isolated polynucleotides (e.g., DNA and RNA transcripts, both sense and antisense strands) encoding a novel human $\beta_2$ integrin α subunit, $\alpha_d$, and variants thereof (i.e., deletion, addition or substitution analogs) which possess binding and/or immunological properties inherent to $\alpha_d$. Preferred DNA molecules of the invention include cDNA, genomic DNA and wholly or partially chemically synthesized DNA molecules. A presently preferred polynucleotide is the DNA as set forth in SEQ ID NO: 1, encoding the polypeptide of SEQ ID NO: 2. Also provided are recombinant plasmid and viral DNA constructions (expression constructs) which include $\alpha_d$ encoding sequences, wherein the $\alpha_d$ encoding sequence is operatively linked to a homologous or heterologous transcriptional regulatory element or elements.

Also provided by the present invention are isolated and purified mouse and rat polynucleotides which exhibit homology to polynucleotides encoding human $\alpha_d$. A preferred mouse polynucleotide is set forth in SEQ ID NO: 45; a preferred rat polynucleotide is set forth in SEQ ID NO: 36.

As another aspect of the invention, prokaryotic or eukaryotic host cells transformed or transfected with DNA sequences of the invention are provided which express $\alpha_d$ polypeptide or variants thereof. Host cells of the invention are particularly useful for large scale production of $\alpha_d$ polypeptide, which can be isolated from either the host cell itself or from the medium in which the host cell is grown. Host cells which express $\alpha_d$ polypeptide on their extracellular membrane surface are also useful as immunogens in the production of $\alpha_d$-specific antibodies. Preferably, host cells transfected with $\alpha_d$ will be cotransfected to express a $\beta_2$ integrin subunit in order to allow surface expression of the heterodimer.

Also provided by the present invention are purified and isolated $\alpha_d$ polypeptides, fragments and variants thereof. Preferred $\alpha_d$ polypeptides are as set forth in SEQ ID NO: 2. Novel $\alpha_d$ products of the invention may be obtained as isolates from natural sources, but, along with $\alpha_d$ variant products, are preferably produced by recombinant procedures involving host cells of the invention. Completely glycosylated, partially glycosylated and wholly deglycosylated forms of the $\alpha_d$ polypeptide may be generated by varying the host cell selected for recombinant production and/or post-isolation processing. Variant $\alpha_d$ polypeptides of the invention may comprise water soluble and insoluble $\alpha_d$ polypeptides including analogs wherein one or more of the amino acids are deleted or replaced: (1) without loss, and preferably with enhancement, of one or more biological activities or immunological characteristics specific for $\alpha_d$; or (2) with specific disablement of a particular ligand/receptor binding or signalling function. Fusion polypeptides are also provided, wherein $\alpha_d$ amino acid sequences are expressed contiguously with amino acid sequences from other polypeptides. Such fusion polypeptides may possess modified biological, biochemical, and/or immunological properties in comparison to wild-type $\alpha_d$. Analog polypeptides including additional amino acid (e.g., lysine or cysteine) residues that facilitate multimer formation are contemplated.

Also comprehended by the present invention are polypeptides and other non-peptide molecules which specifically bind to $\alpha_d$. Preferred binding molecules include antibodies (e.g., monoclonal and polyclonal), counterreceptors (e.g., membrane-associated and soluble forms) and other ligands (e.g., naturally occurring or synthetic molecules), including those which competitively bind $\alpha_d$ in the presence of $\alpha_d$ monoclonal antibodies and/or specific counterreceptors. Binding molecules are useful for purification of $\alpha_d$ polypeptides and identifying cell types which express $\alpha_d$. Binding molecules are also useful for modulating (i.e., inhibiting, blocking or stimulating) of in vivo binding and/or signal transduction activities of $\alpha_d$.

Assays to identify $\alpha_d$ binding molecules are also provided, including immobilized ligand binding assays, solution binding assays, scintillation proximity assays, di-hybrid screening assays, and the like.

In vitro assays for identifying antibodies or other compounds that modulate the activity of $\alpha_d$ may involve, for example, immobilizing $\alpha_d$ or a natural ligand to which $\alpha_d$ binds, detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor of $\alpha_d$ binding.

Another type of assay for identifying compounds that modulate the interaction between $\alpha_d$ and a ligand involves immobilizing $\alpha_d$ or a fragment thereof on a solid support coated (or impregnated with) a fluorescent agent, labelling the ligand with a compound capable of exciting the fluorescent agent, contacting the immobilized $\alpha_d$ with the labelled ligand in the presence and absence of a putative modulator compound, detecting light emission by the fluorescent agent, and identifying modulating compounds as those compounds that affect the emission of light by the fluorescent agent in comparison to the emission of light by the fluorescent agent in the absence of a modulating compound. Alternatively, the $\alpha_d$ ligand may be immobilized and $\alpha_d$ may be labelled in the assay.

Yet another method contemplated by the invention for identifying compounds that modulate the interaction between $\alpha_d$ and a ligand involves transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of $\alpha_d$ and either the DNA binding domain or the activating domain of the transcription factor, expressing in the host cells a second hybrid DNA sequence encoding part or all of the ligand and the DNA binding domain or activating domain of the transcription factor which is not incorporated in the first fusion, evaluating the effect of a putative modulating compound on the interaction between $\alpha_d$ and the ligand by detecting binding of the ligand to $\alpha_d$ in a particular host cell by measuring the production of reporter gene product in the host cell in the presence or absence of the putative modulator, and identifying modulating compounds as those compounds altering production of the reported gene product in comparison to production of the reporter gene product in the absence of the modulating compound. Presently preferred for use in the assay are the ADHI promoter, the lexA DNA binding domain, the GAL4 transactivation domain, the lacZ reporter gene, and a yeast host cell.

A modified version of the foregoing assay may be used in isolating a polynucleotide encoding a protein that binds to $\alpha_d$ by transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of $\alpha_d$ and either the DNA binding domain or the activating domain of the transcription factor, expressing in the host cells a library of second hybrid DNA sequences encoding second fusions of part or all of putative $\alpha_d$ binding proteins and the DNA binding domain or activating domain of the transcription factor which is not incorporated in the first fusion, detecting binding of an $\alpha_d$ binding protein to $\alpha_d$ in a particular host cell by detecting the production of reporter gene product in the host cell, and isolating second hybrid DNA sequences encoding $\alpha_d$ binding protein from the particular host cell.

Hybridoma cell lines which produce antibodies specific for $\alpha_d$ are also comprehended by the invention. Techniques for producing hybridomas which secrete monoclonal antibodies are well known in the art. Hybridoma cell lines may be generated after immunizing an animal with purified $\alpha_d$, variants of $\alpha_d$ or cells which express $\alpha_d$ or a variant thereof on the extracellular membrane surface. Immunogen cell types include cells which express $\alpha_d$ in vivo, or transfected prokaryotic or eukaryotic cell lines which normally do not normally express $\alpha_d$ in vivo.

The value of the information contributed through the disclosure of the DNA and amino acid sequences of $\alpha_d$ is manifest. In one series of examples, the disclosed $\alpha_d$ CDNA sequence makes possible the isolation of the human $\alpha_d$ genomic DNA sequence, including transcriptional control elements for the genomic sequence. Identification of $\alpha_d$ allelic variants and heterologous species (e.g., rat or mouse) DNAs is also comprehended. Isolation of the human $\alpha_d$ genomic DNA and heterologous species DNAs can be accomplished by standard DNA/DNA hybridization techniques, under appropriately stringent conditions, using all or part of the $\alpha_d$ CDNA sequence as a probe to screen an appropriate library. Alternatively, polymerase chain reaction (PCR) using oligonucleotide primers that are designed based on the known CDNA sequence can be used to amplify and identify genomic $\alpha_d$ DNA sequences. Synthetic DNAs encoding the $\alpha_d$ polypeptide, including fragments and other variants thereof, may be produced by conventional synthesis methods.

DNA sequence information of the invention also makes possible the development, by homologous recombination or "knockout" strategies [see, e.g., Kapecchi, *Science* 244:1288–1292 (1989)], to produce rodents that fail to express a functional $\alpha_d$ polypeptide or that express a variant $\alpha_d$ polypeptide. Such rodents are useful as models for studying the activities of $\alpha_d$ and $\alpha_d$ modulators in vivo.

DNA and amino acid sequences of the invention also make possible the analysis of $\alpha_d$ epitopes which actively participate in counterreceptor binding as well as epitopes which may regulate, rather than actively participate in, binding. Identification of epitopes which may participate in transmembrane signal transduction is also comprehended by the invention.

DNA of the invention is also useful for the detection of cell types which express $\alpha_d$ polypeptide. Standard DNA/RNA hybridization techniques which utilize $\alpha_d$ DNA to detect $\alpha_d$ RNA may be used to determine the constitutive level of $\alpha_d$ transcription within a cell, as well as changes in the level of transcription in response to internal or external agents. Identification of agents which modify transcription and/or translation of $\alpha_d$ can, in turn, be assessed for potential therapeutic or prophylactic value. DNA of the invention also makes possible in situ hybridization of $\alpha_d$ DNA to cellular RNA to determine the cellular localization of $\alpha_d$ specific messages within complex cell populations and tissues.

DNA of the invention is also useful for identification of non-human polynucleotide sequences which display homology to human $\alpha_d$ sequences. Possession of non-human $\alpha_d$ DNA sequences permits development of animal models (including, for example, transgenic models) of the human system.

As another aspect of the invention, monoclonal or polyclonal antibodies specific for $\alpha_d$ may be employed in immunohistochemical analysis to localize $\alpha_d$ to subcellular compartments or individual cells within tissues. Immunohistochemical analyses of this type are particularly useful when used in combination with in situ hybridization to localize both $\alpha_d$ mRNA and polypeptide products of the $\alpha_d$ gene.

Identification of cell types which express $\alpha_d$ may have significant ramifications for development of therapeutic and prophylactic agents. It is anticipated that the products of the invention related to $\alpha_d$ can be employed in the treatment of diseases wherein macrophages are an essential element of the disease process.

For example, in BB rats which spontaneously develop type 1 or insulin dependent diabetes, macrophages have been documented as the predominant immune cell infiltrating the earliest detectable pancreatic lesions [Hanenberg, et al., *Diabetologia* 32:126–134 (1989)]. Non-specific removal of macrophages from the system prevents the onset of diabetes. It is therefore anticipated that $\alpha_d$ may play a significant role either in the initial sequestration of the macrophages at the lesion site and/or their subsequent destructive effector functions.

Similarly, the genesis of atherosclerotic lesions is thought to involve the participation of specialized lipid laden macrophages termed foam cells, potentially both as triggering and sustaining elements of lesion progression. Since one ligand of $\alpha_d$, ICAM-R, is known to be expressed on activated endothelial cells at neovascularizing sites as might occur in certain types of nascent atherosclerotic lesions, it is anticipated that interactions mediated by $\alpha_d$ on macrophages may serve both to facilitate the initial sequestration of the cells within the nascent lesion and potentially to promote their activation.

Other diseases which involve activated macrophages as a central participant include, but are not limited to, multiple sclerosis, asthma, psoriasis, and rheumatoid arthritis.

Pharmaceutical compositions for treatment of these and other disease states are provided by the invention. Pharmaceutical compositions are designed for the purpose of inhibiting interaction between $\alpha_d$ and its ligand(s) and include various soluble and membrane-associated forms of $\alpha_d$ (comprising the entire $\alpha_d$ polypeptide, or fragments thereof, which actively participate in $\alpha_d$ binding), soluble and membrane-associated forms of $\alpha_d$ binding proteins (including antibodies, ligands, and the like), intracellular or extracellular modulators of $\alpha_d$ binding activity, and/or modulators of $\alpha_d$ and/or $\alpha_d$-ligand polypeptide expression, including modulators of transcription, translation, posttranslational processing and/or intracellular transport. The invention also comprehends methods for treatment of disease states in which $\alpha_d$ binding is implicated, wherein a patient suffering from said disease state is provided an amount of a pharmaceutical composition of the invention sufficient to modulate levels of $\alpha_d$ binding. The method of treatment of the invention is applicable to disease states such as, but not limited to, type I diabetes, atherosclerosis, multiple sclerosis, asthma, psoriasis, and rheumatoid arthritis.

BRIEF DESCRIPTION OF THE DRAWING

Numerous other aspects and advantages of the present invention will be apparent upon consideration of the following description thereof, reference being made to the drawing wherein:

FIG. 1A through 1D comprises an alignment of the human amino acid sequences of CD11b (SEQ ID NO: 3), CD11c (SEQ ID NO: 4) and $\alpha_d$ (SEQ ID NO: 2).

DETAILED DESCRIPTION OF THE INVENTION

The present invention is illustrated by the following examples relating to the isolation of a cDNA clone encoding $\alpha_d$ from a human spleen cDNA library. More particularly, Example 1 illustrates the use of anti-canine $\alpha_{TM1}$ antibody in an attempt to detect a homologous human protein. Example 2 details purification of canine $\alpha_{TM1}$ and N-terminal sequencing of the polypeptide to design oligonucleotide primers for PCR amplification of the canine $\alpha_{TM1}$ gene. Example 3 addresses large scale purification of canine $\alpha_{TM1}$ for internal sequencing in order to design additional PCR primers. Example 4 describes use of the PCR and internal sequence primers to amplify a fragment of the canine $\alpha_{TM1}$ gene. Example 5 addresses cloning of the human $\alpha_d$-encoding cDNA sequence. Example 6 describes Northern blot hybridization analysis of human tissue and cells for expression of $\alpha_d$ mRNA. Example 7 details the construction of human $\alpha_d$ expression plasmids and transfection of COS cells with the resulting plasmids. Example 8 addresses ELISA analysis of $\alpha_d$ expression in transfected COS cells. Example 9 describes FACS analysis of COS cells transfected with human $\alpha_d$ expression plasmids. Example 10 addresses immunoprecipitation of CD18 in association with $\alpha_d$ in co-transfected COS cells. Example 11 relates to stable transfection of $\alpha_d$ expression constructs in Chinese hamster ovary cells. Example 12 addresses CD18-dependent binding of $\alpha_d$ to the intercellular adhesion molecule, ICAM-R. Example 13 describes scintillation proximity screening assays to identify inhibitors of $\alpha_d$ ligand/anti-ligand binding interactions. Example 14 addresses construction of expression plasmids which encode soluble forms of $\alpha_d$. Example 15 relates to production of $\alpha_d$-specific monoclonal antibodies. Example 16 describes isolation of rat cDNA sequences which show homology to human $\alpha_d$ gene sequences. Example 17 addresses isolation of mouse cDNA sequences which show homology to human $\alpha_d$ gene sequences. Example 18 relates to in situ hybridization analysis of various mouse tissues to determine tissues and cell specific expression of the putative mouse homolog to human $\alpha_d$. Example 19 describes generation of expression constructs which encode the putative mouse homolog of human $\alpha_d$. Example 20 addresses design of a "knockout" mouse wherein the gene encoding the putative mouse homolog of human $\alpha_d$ is disrupted.

EXAMPLE 1

Attempt to Detect a Human Homolog of Canine $\alpha_{TM1}$

The monoclonal antibody Ca11.8H2 [Moore, et al., supra] specific for canine $\alpha_{TM1}$ was tested for cross-reactivity on human peripheral blood leukocytes in an attempt to identify a human homolog of canine $\alpha_{TM1}$. Cell preparations (typically $1 \times 10^6$ cells) were incubated with undiluted hybridoma supernatant or a purified mouse IgG-negative control antibody (10 µg/ml) on ice in the presence of 0.1% sodium azide. Monoclonal antibody binding was detected by subsequent incubation with FITC-conjugated horse anti-mouse IgG (Vector Laboratories, Burlingame, Calif.) at 6 µg/ml. Stained cells were fixed with 2% w/v paraformaldehyde in phosphate buffered saline (PBS) and were analyzed with a Facstar Plus fluorescence-activated cell sorter (Becton Dickinson, Mountain View, Calif.). Typically, 10,000 cells were analyzed using logarithmic amplification for fluorescence intensity.

The results indicated that Ca11.8H2 did not cross-react with surface proteins expressed on human peripheral blood leukocytes, while the control cells, neoplastic canine peripheral blood lymphocytes, were essentially all positive for $\alpha_{TM1}$.

Because the monoclonal antibody Ca11.8H2 specific for the canine α subunit did not cross react with a human homolog, isolation of canine $\alpha_{TM1}$ DNA was deemed a necessary prerequisite to isolate a counterpart human gene if one existed.

EXAMPLE 2

Affinity Purification Of Canine $\alpha_{TM1}$ For N-Terminal Sequencing

Canine $\alpha_{TM1}$ was affinity purified in order to determine N-terminal amino acid sequences for oligonucleotide probe/primer design. Briefly, anti-$\alpha_{TM1}$ monoclonal antibody Ca11.8H2 was coupled to Affigel 10 chromatographic resin (BioRad, Hercules, Calif.) and protein was isolated by specific antibody-protein interaction. Antibody was conjugated to the resin, according to the BioRad suggested protocol, at a concentration of approximately 5 mg antibody per ml of resin. Following the conjugation reaction, excess antibody was removed and the resin blocked with three volumes of 0.1M ethanolamine. The resin was then washed with thirty column volumes of phosphate buffered saline (PBS).

Twenty-five grams of a single dog spleen were homogenized in 250 ml of buffer containing 0.32M sucrose in 25 mM Tris-HCl, Ph 8.0, with protease inhibitors. Nuclei and cellular debris were pelleted with centrifugation at 1000 g for 15 minutes. Membranes were pelleted from the supernatant with centrifugation at 100,000 g for 30 minutes. The membrane pellet was resuspended in 200 ml lysis buffer (50 mM NaCl, 50 mM borate, pH 8.0, with 2 % NP-40) and incubated for 1 hour on ice. Insoluble material was then pelleted by centrifugation at 100,000 g for 60 minutes. Ten milliliters of the cleared lysate were transferred to a 15 ml polypropylene tube with 0.5 ml Call.8H2-conjugated Affigel 10 resin described above. The tube was incubated overnight at 4° C. with rotation and the resin subsequently washed with 50 column volumes D-PBS. The resin was then transferred to a microfuge tube and boiled for ten minutes in 1 ml Laemmli (non-reducing) sample buffer containing 0.1M Tris-HCl, pH 6.8, 2% SDS, 20% glycerol and 0.002% bromophenol blue. The resin was pelleted by centrifugation and discarded; the supernatant was treated with 1/15 volume β-mercaptoethanol (Sigma, St. Louis, Mo.) and run on a 7% polyacrylamide gel. The separated proteins were transferred to Immobilon PVDF membrane (Millipore, Bedford, Mass.) as follows.

The gels were washed once in deionized, Millipore-filtered water and equilibrated for 15–45 minutes in 10 mM 3-[cyclohexylamino]-1-propanesulfonic acid (CAPS) transfer buffer, pH 10.5, with 10% methanol. Immobilon membranes were moistened with methanol, rinsed with filtered water, and equilibrated for 15–30 minutes in CAPS transfer buffer. The initial transfer was carried out using a Biorad transfer apparatus at 70 volts for 3 hours. The Immobilon membrane was removed after transfer and stained in filtered 0.1% R250 Coomassie stain for 10 minutes. Membranes were destained in 50% methanol/10% acetic acid three times, ten minutes each time. After destaining, the membranes were washed in filtered water and air-dried.

Protein bands of approximately 150 kD, 95 kD, 50 kD and 30 kD were detected. Presumably the 50 kD and 30 kD bands resulted from antibody contamination. N-terminal sequencing was then attempted on both the 150 kD and 95 kD bands, but the 95 kD protein was blocked, preventing sequencing. The protein band of 150 kD was excised from the membrane and directly sequenced with an Applied Biosystems (Foster City, Calif.) Model 473A protein sequencer according to the manufacturer's instructions. The resulting amino acid sequence is set in SEQ ID NO: 5 using single letter amino acid designations.

FNLDVEEPMVFQ (SEQ ID NO: 5)

The identified sequence included the FNLD sequence characteristic of α subunits of the integrin family [Tamura, et al., J. Cell. Biol. 111:1593–1604 (1990)].

Primer Design and Attempt to Amplify Canine $\alpha_{TM1}$ Sequences

From the N-terminal sequence information, three oligonucleotide probes were designed for hybridization: a) "Tommer," a fully degenerate oligonucleotide; b) "Patmer," a partially degenerate oligonucleotide; and c) "Guessmer," a nondegenerate oligonucleotide based on mammalian codon usage. These probes are set out below as SEQ ID NOS: 6, 7 and 8, respectively. Nucleic acid symbols are in accordance with 37 C.F.R. §1.882 for these and all other nucleotide sequences herein.

5'-TRYAAYYTGGAYGTNGAROARCCNATGGTNTTYCA-3'

(SEQ ID NO: 6)

5'-TTCAACCTGGACGTGGAGGAGCCCATGGTGTTCCAA-3'

(SEQ ID NO: 7)

5'-TTCAACCTGGACGTNGAASANCCCATGGTCTTCCAA-3'

(SEQ ID NO: 8)

Based on sequencing data, no relevant clones were detected using these oligonucleotides in several low stringency hybridizations to a canine spleen/peripheral blood macrophage cDNA library cloned into λZAP (Stratagene, La Jolla, Calif.).

Four other oligonucleotide primers, designated 5'Deg, 5'Spec, 3'Deg and 3'Spec (as set out in SEQ ID NOS: 9, 10, 11 and 12, respectively, wherein Deg indicates degenerate and Spec indicates non-degenerate) were subsequently designed based on the deduced N-terminal sequence for attempts to amplify canine $\alpha_{TM1}$ sequences by PCR from phage library DNA purified from plate lysates of the Stratagene library described above.

| | |
|---|---|
| 5'-TTYAAYYTNGAYGTNGARGARCC-3' | (SEQ ID NO: 9) |
| 5'-TTYAAYYTGGACGTNGAAGA-3' | (SEQ ID NO: 10) |
| 5'-TGRAANACCATNGGYTC-3' | (SEQ ID NO: 11) |
| 5'-TTGGAAGACCATNGGYTC-3' | (SEQ ID NO: 12) |

The $\alpha_{TM1}$ oligonucleotide primers were paired with T3 or T7 vector primers, as set out in SEQ ID NOS: 13 and 14, respectively, which hybridize to sequences flanking the polylinker region in the Bluescript phagemid found in λZAP.

| | |
|---|---|
| 5'-ATTAACCCTCACTAAAG-3' | (SEQ ID NO: 13) |
| 5'-AATACGACTCACTATAG-3' | (SEQ ID NO: 14) |

The PCR amplification was carried out in Taq buffer (Boehringer Mannheim, Indianapolis, Ind.) containing magnesium with 150 ng of library DNA, 1 μg of each primer, 200 μM dNTPs and 2.5 units Taq polymerase (Boehringer Mannheim) and the products were separated by electrophoresis on a 1% agarose gel in Tris-Acetate-EDTA (TAE) buffer with 0.25 μg/ml ethidium bromide. DNA was transferred to a Hybond (Amersham, Arlington Heights, Ill.) membrane by wicking overnight in 10X SSPE. After transfer, the immobilized DNA was denatured with 0.5M NaOH with 0.6M NaCl, neutralized with 1.0M Tris-HCl, pH 8.0, in 1.5M NaCl, and washed with 2X SSPE before UV crosslinking with a Stratalinker (Stratagene) crosslinking apparatus. The membrane was incubated in prehybridization buffer (5X SSPE, 4X Denhardts, 0.8% SDS, 30% formamide) for 2 hr at 50° C. with agitation.

Oligonucleotide probes 5'Deg, 5'Spec, 3'Deg and 3'Spec (SEQ ID NOS: 9, 10, 11 and 12, respectively) were labeled using a Boehringer Mannheim kinase buffer with 100–300 μCi γP$^{32}$-dATP and 1–3 units of polynucleotide kinase for 1–3 hr at 37° C. Unincorporated label was removed with Sephadex G-25 fine (Pharmacia, Piscataway, N.J.) chromatography using 10 mM Tris-HCl, pH 8.0, 1 mM EDTA (TE) buffer and the flow-through added directly to the prehybridization solution. Membranes were probed for 16 hr at 42° C. with agitation and washed repeatedly, with a final stringency wash of 1X SSPE/0.1% SDS at 50° for 15 min. The blot was then exposed to Kodak X-Omat AR film for 1–4 hours at −80° C.

The oligonucleotides 5'Deg, 5'Spec, 3'Deg and 3'Spec only hybridized to PCR products from the reactions in which they were used as primers and failed to hybridize as expected to PCR products from the reactions in which they were not used as primers. Thus, it was concluded that none of the PCR products were specific for $\alpha_{TM1}$ because no product hybridized with all of the appropriate probes.

EXAMPLE 3

Large Scale Affinity Purification Of Canine $\alpha_{TM1}$ For Internal Sequencing In order to provide additional amino acid sequence for primer design, canine $\alpha TM_1$ was purified for internal sequencing. Three sections of frozen spleen (approximately 50 g each) and frozen cells from two partial spleens from adult dogs were used to generate protein for internal sequencing. Fifty grams of spleen were homogenized in 200–300 ml borate buffer with a Waring blender. The homogenized material was diluted with 1 volume of buffer containing 4 % NP-40, and the mixture then gently agitated for at least one hour. The resulting lysate was cleared of large debris by centrifugation at 2000 g for 20 rain, and then filtered through either a Corning (Corning, N.Y.) prefilter or a Corning 0.8 micron filter. The lysate was further clarified by filtration through the Corning 0.4 micron filter system.

Splenic lysate and the antibody-conjugated Affigel 10 resin described in Example 2 were combined at a 150:1 volume ratio in 100 ml aliquots and incubated overnight at 4° C. with rocking. The lysate was removed after centrifugation at 1000 g for 5 minutes, combined with more antibody-conjugated Affigel 10 resin and incubated overnight as above. The absorbed resin aliquots were then combined and washed with 50 volumes D-PBS/0.1% Tween 20 and the resin transferred to a 50 ml Biorad column. Adsorbed protein was eluted from the resin with 3–5 volumes of 0.1M glycine (pH 2.5); fractions of approximately 900 μl were collected and neutralized with 100 μl 1M Tris buffer, pH 8.0. Aliquots of 15 μl were removed from each fraction and boiled in an equal volume of 2X Laemmli sample buffer with ⅟₁₅ volume 1M dithiothreitol (DTT). These samples were electrophoresed on 8 % Novex (San Diego, Calif.) polyacrylamide gels and visualized either by Coomassie stain or by silver stain using a Daiichi kit (Enprotech, Natick, Mass.) according to the manufacturer's suggested protocol. Fractions which contained the largest amounts of protein were combined and concentrated by vacuum. The remaining solution was diluted by 50% with reducing Laemmli sample buffer and run on 1.5 mm 7% polyacrylamide gels in Tris-glycine/SDS buffer. Protein was transferred from the gels to Immobilon membrane by the procedure described in Example 2 using the Hoefer transfer apparatus.

The protein bands corresponding to canine $\alpha_{TM1}$ were excised from 10 PVDF membranes and resulted in approximately 47 μg total protein. The bands were destained in 4 ml 50% methanol for 5 minutes, air dried and cut into 1×2 mm pieces. The membrane pieces were submerged in 2 ml 95% acetone at 4° C. for 30 minutes with occasional vortexing and then air dried.

Prior to proteolytic cleavage of the membrane bound protein, 3 mg of cyanogen bromide (CNBr) (Pierce, Rockford, Ill.) were dissolved in 1.25 ml 70% formic acid. This solution was then added to a tube containing the PVDF membrane pieces and the tube incubated in the dark at room temperature for 24 hours. The supernatant (S1) was then removed to another tube and the membrane pieces washed with 0.25 ml 70% formic acid. This supernatant (S2) was removed and added to the previous supernatant (S1). Two milliliters of Milli Q water were added to the combined supernatants (S1 and S2) and the solution lyophilized. The PVDF membrane pieces were dried under nitrogen and extracted again with 1.25 ml 60% acetonitrile, 0.1% tetrafluoroacetic acid (TFA) at 42° C. for 17 hours. This supernatant (S3) was removed and the membrane pieces extracted again with 1.0 ml 80% acetonitrile with 0.08% TFA at 42° C. for 1 hour. This supernatant (S4) was combined with the previous supernatants (S1, S2 and S3) and vacuum dried.

The dried CNBr fragments were then dissolved in 63 μl 8M urea, 0.4M NH₄HCO₃. The fragments were reduced in 5 μl 45 mM dithiothreitol (DTT) and subsequently incubated at 50° C. for 15 minutes. The solution was then cooled to room temperature and the fragments alkylated by adding 5 μl 100 mM iodoacetamide (Sigma, St. Louis, Mo.). Following a 15 minute incubation at room temperature, the sample was diluted with 187 μl Milli Q water to a final urea concentration of 2.0M. Trypsin (Worthington, Freehold, N.J.) was then added at a ratio of 1:25 (w:w) of enzyme to protein and the protein digested for 24 hours at 37° C. Digestion was terminated with addition of 30 μl TFA.

The protein fragments were then separated with high performance liquid chromatography (HPLC) on a Waters 625 LC system (Millipore, Milford, Mass.) using a 2.1×250 mm, 5 micron Vydac C-18 column (Vydac, Hesperia, Calif.) equilibrated in 0.05% TFA and HPLC water (buffer A). The peptides were eluted with increasing concentration of 80% acetonitrile in 0.04% TFA (buffer B) with a gradient of 38–75% buffer B for 65–95 minutes and 75–98% buffer B for 95–105 minutes. Peptides were fractionated at a flow rate of 0.2 ml/minute and detected at 210 nm.

Following fractionation, the amino acid sequence of the peptides was analyzed by automated Edman degradation performed on an Applied Biosystems Model 437A protein sequencer using the manufacturer's standard cycles and the Model 610A Data Analysis software program, Version 1.2.1. All sequencing reagents were supplied by Applied Biosystems. The amino acid sequences of seven of the eight internal fragments are set out below wherein "X" indicates the identity of the amino acid was not certain.

| | |
|---|---|
| VFQEXGAGFGQ | (SEQ ID NO: 15) |
| LYDXVAATGLXQPI | (SEQ ID NO: 16) |
| PLEYXDVIPQAE | (SEQ ID NO: 17) |
| FQEGFSXVLX | (SEQ ID NO: 18) |
| TSPTFIXMSQENVD | (SEQ ID NO: 19) |
| LVVGAPLEVVAVXQTGR | (SEQ ID NO: 20) |
| LDXKPXDTA | (SEQ ID NO: 21) |

Primer Design

One internal amino acid sequence (set out in SEQ ID NO: 22) obtained was then used to design a fully degenerate oligonucleotide primer, designated p4(R) as set out in SEQ ID NO: 23.

| | |
|---|---|
| FGEQFSE | (SEQ ID NO: 22) |

5'-RAANCCYTCYTGRAAACTYTC-3'    (SEQ ID NO: 23)

EXAMPLE 4

PCR Cloning Of A Canine $\alpha_{TM1}$ Fragment

The 5' portion of the canine $\alpha_{TM1}$ gene was amplified from double-stranded canine splenic cDNA by PCR.

A. Generation of Double Stranded Canine Spleen cDNA

One gram of frozen material from a juvenile dog spleen was ground in liquid nitrogen on dry ice and homogenized in 20 ml RNA-Stat 60 buffer (Tel-Test B, Inc, Friendswood, Tex.). Four ml chloroform were added, and the solution extracted by centrifugation at 12,000 g for 15 minutes. RNA was precipitated from the aqueous layer with 10 ml ethanol. Poly A⁺ RNA was then selected on Dynal Oligo dT Dynabeads (Dynal, Oslo, Norway). Five aliquots of 100 µg total RNA were combined and diluted with an equal volume of 2X binding buffer (20 mM Tris-HCl, pH 7.5, 1.0M LiCl, 1 mM EDTA, 0.1% SDS). RNA was then incubated 5 minutes with the Oligo dT Dynabeads (1.0 ml or 5 mg beads for all the samples). Beads were washed with buffer containing 10 mM Tris-HCl, pH 7.5, 0.15M LiCl, 1 mM EDTA and 0.1% SDS, according to the manufacturer's suggested protocol prior to elution of poly A⁺ mRNA with 2 mM EDTA, pH 7.5. Double-stranded cDNA was then generated using the eluted poly A⁺ mRNA and the Boehringer Mannheim cDNA Synthesis Kit according to the manufacturer's suggested protocol.

B. Isolation of a Partial Canine $\alpha_{TM1}$ cDNA

Oligonucleotide primers 5'Deg (SEQ ID NO: 9) and p4(R) (SEQ ID NO: 23) were employed in a standard PCR reaction using 150 ng double-stranded cDNA, 500 ng of each primer, 200 µM dNTPs and 1.5 units Taq polymerase (Boehringer Mannheim) in Taq buffer (Boehringer Mannheim) with magnesium. The resulting products (1 µl of the original reaction) were subjected to a second round of PCR with the same primers to increase product yield. This band was eluted from a 1% agarose gel onto Schleicher & Schuell (Keene, N.H.) NA45 paper in a buffer containing 10 mM Tris-HCl, pH 8, 1 mM EDTA, 1.5M NaCl at 65° C., precipitated, and ligated into the pCR™II vector (Invitrogen, San Diego, Calif.) using the TA cloning kit (Invitrogen) and the manufacturer's suggested protocol. The ligation mixture was transformed by electroporation into XL-1 Blue bacteria (Stratagene). One clone, 2.7, was determined to contain sequences corresponding to $\alpha_{TM1}$ peptide sequences which were not utilized in design of the primers.

Sequencing was performed with an Applied Biosystems 373A DNA sequencer (Foster City, Calif.) with a Dye-deoxy terminator cycle sequence kit (ABI) in which fluorescent-labeled dNTPs were incorporated in an asymmetric PCR reaction [McCabe, "Production of Single Stranded DNA by Asymmetric PCR," in PCR Protocols: A Guide to Methods and Applications, Innis, et al. (eds.) pp. 76–83 Academic Press: New York (1990)] as follows. Samples were held at 96° C. for 4 minutes and subjected to 25 cycles of the step sequence: 96° C., for 15 seconds; 50° C. for 1 second; 60° C. for 4 minutes. Sequence data was automatically downloaded into sample files on the computer that included chromatogram and text files. The sequence of the entire insert of clone 2.7 is set out in SEQ ID NO: 24.

Attempts to isolate the full length canine $\alpha_{TM1}$ cDNA from the Stratagene library (as described in Example 2) were unsuccessful. Approximately 1×10⁶ phage plaques were screened by hybridization under low stringency conditions using 30% formamide with clone 2.7 as a probe, but no positive clones resulted. Attempts to amplify relevant sequences downstream from those represented in clone 2.7 using specific oligonucleotides derived from clone 2.7 or degenerate primers based on amino acid sequence from other peptide fragments paired with a degenerate oligonucleotide based on the conserved α subunit amino acid motif GFFKR [Tamura, et al., supra] were also unsuccessful.

EXAMPLE 5

Cloning Of A Putative Human Homolog Of Canine $\alpha_{TM1}$

To attempt the isolation of a human sequence homologous to canine $\alpha_{TM1}$ the approximately 1 kb canine $\alpha_{TM1}$ fragment from clone 2.7 was used as a probe. The probe was generated by PCR under conditions described in Example 2 using NT2 (as set out in SEQ ID NO: 25) and p4(R) (SEQ ID NO: 23) primers.

5'-GTNTTYCARGARGAYGG-3'    (SEQ ID NO: 25)

The PCR product was purified using the Qiagen (Chatsworth, Ga.) Quick Spin kit and the manufacturer's suggested protocol. The purified DNA (200 ng) was labeled with 200 µCi $\alpha^{32}$PdCTP using the Boehringer Mannheim Random Prime Labelling kit and the manufacturer's suggested protocol. Unincorporated isotope was removed with Sephadex G25 (fine) gravity chromatography. The probe was denatured with 0.2N NaOH and neutralized with 0.4M Tris-HCl, pH 8.0, before use.

Colony lifts on Hybond filters (Amersham) of a human spleen cDNA library in pCDNA/Amp (Invitrogen, San Diego, Calif.) were prepared. The filters were initially denatured and neutralized as described in Example 2 and subsequently incubated in a prehybridization solution (8 ml/filter) with 30% formamide at 50° C. with gentle agitation for 2 hours. Labeled probe as described above was added to this solution and incubated with the filters for 14 hours at 42° C. The filters were washed twice in 2X SSC/0.1% SDS at 37° C. and twice in 2X SSC/0.1% SDS at 50° C. Final stringency washes were 1X SSC/0.1% SDS, twice at 65° C. (1X SSC is 150 mM NaCl, 15 mM sodium citrate, pH 7.0). Filters were exposed to Kodak X-Omat AR film for six hours with an intensifying screen. Colonies giving signals on duplicate lifts were streaked on LB medium with magnesium (LBM)/carbenicillin plates and incubated overnight at 37° C. Resulting streaked colonies were lifted with Hybond filters and these filters were treated as above. The filters were hybridized under more stringent conditions with the 1 kb probe from clone 2.7, labeled as previously described, in a 50% formamide hybridization solution at 50° C. for 3 hours. Probed filters were washed with a final stringency of 0.1 X SSC/0.1% SDS at 65 ° C. and exposed to Kodak X-Omar AR film for 2.5 hours at –80° C. with an intensifying screen. Positive colonies were identified and cultured in LBM/carbenicillin medium overnight. DNA from the cultures was prepared using the Promega Wizard miniprep kit according to the manufacturer's suggested protocol and the resulting DNA was sequenced.

The initial screening resulted in 18 positive clones, while the secondary screening under more stringent hybridization conditions produced one positive clone which was designated 19A2. The DNA and deduced amino acid sequences of the human $\alpha_d$ clone 19A2 are set out in SEQ ID NOS: 1 and 2, respectively.

Characteristics Of The Human $\alpha_d$ cDNA and Predicted Polypeptide

Clone 19A2 encompasses the entire coding region for the mature protein, plus 48 bases (16 amino acid residues) of the 5' upstream signal sequence and 241 bases of 3' untranslated sequence which do not terminate in a polyadenylation sequence. The core molecular weight of the mature protein is predicted to be around 125 kD. The extracellular domain is predicted to encompass approximately amino acid residues 17 through 1108 of SEQ ID NO: 2. This extracellular region is contiguous with about a 20 amino acid region homologous to the human CD11c transmembrane region (residues 1109 through 1128 of SEQ ID NO: 2). The cytoplasmic domain comprises approximately 30 amino acids (about residues 1129 through 1161 of SEQ ID NO: 2). The protein also contains a region (around residues 150 through 352) of approximately 202 amino acids homologous to the I (insertion) domain common to CD11a, CD11b and CD11c [Larson and Springer, supra], $\alpha_E$ [Shaw, et al., *J. Biol. Chem.* 269:6016–6025 (1994)] and in VLA-1 and VLA-2, [Tamura, et al., supra]. The I domain in other integrins has been shown to participate in ICAM binding [Landis, et al., *J. Cell. Biol.* 120:1519–1527 (1993); Diamond, et al., *J. Cell. Biol.* 120:1031–1043 (1993)], suggesting that $\alpha_d$ may also bind members of the ICAM family of surface molecules. This region has not been demonstrated to exist in any other integrin subunits.

The deduced amino acid sequence of $\alpha_d$ shows approximately 36% identity to that of CD11a, approximately 60% identity to CD11b and approximately 66% identity to CD11c. An alignment of amino acid sequences for (CD11b SEQ ID NO: 3), CD11c (SEQ ID NO: 4) and $\alpha_d$ (SEQ ID NO: 2) is presented in FIG. 1.

The cytoplasmic domains of $\alpha$ subunits in $\beta_2$ integrins are typically distinct from one another within the same species, while individual $\alpha$ subunits show high degrees of homology across species boundaries. Consistent with these observations, the cytoplasmic region of $\alpha_d$ differs markedly from CD11a, CD11b, and CD11c except for a membrane proximal GFFKR amino acid sequence which has been shown to be conserved among all $\alpha$ integrins [Rojiani, et al., *Biochemistry* 30:9859–9866 (1991)]. Since the cytoplasmic tail region of integrins has been implicated in "inside out" signaling and in avidity regulation [Landis et al., supra], it is possible that $\alpha_d$ interacts with cytosolic molecules distinct from those interacting with CD11a, CD11b, and CD11c, and, as a result, participates in signaling pathways distinct from those involving other $\beta$ integrins.

The extracellular domain of $\alpha_d$ contains a conserved DGSGS amino acid sequence adjacent the I-domain; in CD11b, the DGSGS sequence is a metal-binding region required for ligand interaction [Michishita, et al. *Cell* 72:857–867 (1993)]. Three additional putative cation binding sites in CD11b and CD11c are conserved in the $\alpha_d$ sequence at amino acids 465–474, 518–527, and 592–600 in clone 19A2 (SEQ ID NO: 1 ). The $\alpha_d$ I-domain is 36%, 62%, and 57% identical to the corresponding regions in CD11a, CD11b, and CD11c, respectively, and the relatively low sequence homology in this region suggests that $\alpha_d$ may interact with a set of extracellular proteins distinct from proteins with which other known $\beta$ integrins interact. Alternatively, the affinity of $\alpha_d$ for known $\beta_2$ integrin ligands, for example, ICAM-1, ICAM-2 and/or ICAM-R, may be distinct from that demonstrated for the other $\beta$ integrin/ICAM interactions. [See Example 12.]

EXAMPLE 6

Northern Analysis of Human $\alpha_d$ Expression in Tissues

In order to determine the relative level of expression and tissue specificity of $\alpha_d$, Northern analysis was performed using fragments from clone 19A2 as probes. Approximately 10 μg of total RNA from each of several human tissues or cultured cell lines were loaded on a formaldehyde agarose gel in the presence of 1 μg of ethidium bromide. After electrophoresis at 100 V for 4 hr, the RNA was transferred to a nitrocellulose membrane (Schleicher & Schuell) by wicking in 10X SSC overnight. The membrane was baked 1.5 hr at 80° C. under vacuum. Prehybridization solution containing 50% formamide in 3-(N-morpholino)propane sulfonic acid (MOPS) buffer was used to block the membrane for 3 hr at 42° C. Fragments of clone 19A2 were labeled with the Boehringer Mannheim Random Prime kit according to the manufacturer's instructions including both $\alpha P^{32}dCTP$ and $\alpha P^{32}dTTP$. Unincorporated label was removed on a Sephadex G25 column in TE buffer. The membrane was probed with $1.5\times10^6$ counts per ml of prehybridization buffer. The blot was then washed successively with 2X SSC/0.1% SDS at room temperature, 2X SSC/0.1% SDS at 42° C., 2X SSC/0.1% SDS at 50° C., 1X SSC/0.1% SDS at 50° C., 0.5X SSC/0.1% SDS at 50° C. and 0.1X SSC/0.1% SDS at 50° C. The blot was then exposed to film for 19 hr.

Hybridization using a BstXI fragment from clone 19A2 (corresponding to nucleotides 2011 to 3388 in SEQ ID NO: 1) revealed a weak signal in the approximately 5 kb range in liver, placenta, thymus, and tonsil total RNA. No signal was detected in kidney, brain or heart samples. The amount of RNA present in the kidney lane was minimal, as determined with ethidium bromide staining.

When using a second fragment of clone 19A2 (encompassing the region from bases 500 to 2100 in SEQ ID NO: 1), RNA transcripts of two different sizes were detected in a human multi-tissue Northern (MTN) blot using polyA+ RNA (Clontech). An approximately 6.5 kb band was observed in spleen and skeletal muscle, while a 4.5 kb band was detected in lung and peripheral blood leukocytes. The variation in sizes observed could be caused by tissue specific polyadenylation, cross reactivity of the probe with other integrin family members, or hybridization with alternatively spliced mRNAs.

Northern analysis using a third fragment from clone 19A2, spanning nucleotides 2000 to 3100 in SEQ ID NO: 1, gave results consistent with those using the other clone 19A2 fragments.

RNA from three myeloid lineage cell lines was also probed using the fragments corresponding to nucleotides 500 to 2100 and 2000 to 3100 in SEQ ID NO: 1. A THP-1 cell line, previously stimulated with PMA, gave a diffuse signal in the same size range (approximately 5.0 kb), with a slightly stronger intensity than the tissue signals. RNA from unstimulated and DMSO-stimulated HL-60 cells hybridized with the $\alpha_d$ probe at the same intensity as the tissue samples, however, PMA treatment seemed to increase the signal intensity. Since PMA and DMSO drive HL-60 cell differentiation toward monocyte/macrophage and granulocyte pathways, respectively, this result suggests enhanced $\alpha_d$ expression in monocyte/macrophage cell types. U937 cells expressed the $\alpha_d$ message and this signal did not increase with PMA stimulation. No band was detected in Molt, Daudi, H9, JY, or Jurkat cells.

EXAMPLE 7

Transient Expression of Human $\alpha_d$ Constructs

A. Generation of expression constructs

The human clone 19A2 lacks an initiating methionine codon and possibly some of the 5' signal sequence. Therefore, in order to generate a human expression plasmid containing 19A2 sequences, two different strategies were used. In the first, two plasmids were constructed in which signal peptide sequences derived from genes encoding either CD11b or CD11c were spliced into clone 19A2 to generate a chimeric $\alpha_d$ sequence. In the second approach, a third plasmid was constructed in which an adenosine base was added at position 0 in clone 19A2 to encode an initiating methionine.

The three plasmids contained different regions which encoded the 5' portion of the $\alpha_d$ sequence or the chimeric $\alpha_d$ sequence. The $\alpha_d$ region was PCR amplified (see conditions in Example 2) with a specific 3' primer BamRev (set out below in SEQ ID NO: 26) and one of three 5' primers. The three 5' primers contained in sequence: (1) identical non-specific bases at positions 1–6 allowing for digestion, an EcoRI site from positions 7–12 and a consensus Kozak sequence from positions 13–18; (2) a portion of the CD11b (primer ER1B) or CD11c (primer ER1C) signal sequence, or an adenosine (primer ER1D); and (3) an additional 15–17 bases specifically overlapping 5' sequences from clone 19A2 to allow primer annealing. Primers ER1B, ER1C or ER1D are set out in SEQ ID NOS: 27, 28 or 29, respectively, where the initiating methionine codon is underlined and the EcoRI site is double underlined.

Primer BamRev            (SEQ ID NO: 26)

5'-CCACTGTCAGGATGCCCGTG-3'

Primer ER1B              (SEQ ID NO: 27)

5'-A GTTACGAATTCGCCACC
    ATGGCTCTACGGGTGCTTCTTCTG-3'

Primer ER1C              (SEQ ID NO: 28)

5'-AGTTACGAATTCGCCACC
    ATGACTCGGACTGTGCTTCTTCTG-3'

Primer ER1D              (SEQ ID NO: 29)

5'-AGTTACGAATTCGCCACCATGACCTTCGGCACTGTG-3'

The resulting PCR product was digested with EcoRI and BamHI.

All three plasmids contained a common second $\alpha_d$ region (to be inserted immediately downstream from the 5' region described in the previous paragraph) including the 3' end of the $\alpha_d$ clone. The second $\alpha_d$ region, which extended from nucleotide 625 into the XbaI site in the vector 3' polylinker region of clone 19A2, was isolated by digestion of clone 19A2 with BamHI and XbaI.

Three ligation reactions were prepared in which the 3' $\alpha_d$ BamHI/XbaI fragment was ligated to one of the three 5' $\alpha_d$ EcoRI/BamHI fragments using Boehringer Mannheim ligase buffer and T4 ligase (1 unit per reaction). After a 4 hour incubation at 14° C., an appropriate amount of vector pcDNA.3 (Invitrogen) digested with EcoRI and XbaI was added to each reaction with an additional unit of ligase. Reactions were allowed to continue for another 14 hours. One tenth of the reaction mixture was then transformed into competent XL-1 Blue cells. The resulting colonies were cultured and the DNA isolated as in Example 5. Digestion with EcoRI identified three clones which were positive for that restriction site, and thus, the engineered signal sequences. The clones were designated pATM.B1 (CD11b/$\alpha_d$% from primer ER1B), pATM.C10 (CD11c/$\alpha_d$, from primer ER1C) and pATM.D12 (adenosine/$\alpha_d$ from primer ER1d). The presence of the appropriate signal sequences in each clone was verified by nucleic acid sequencing.

B. Transfection of COS Cells

Expression from the $\alpha_d$ plasmids discussed above was effected by cotransfection of COS cells with the individual plasmids and a CD18 expression plasmid, pRC.CD18. As a positive control, COS cells were also co-transfected with the plasmid pRC.CD18 and a CD11a expression plasmid, pDC.CD11A.

Cells were passaged in culture medium (DMEM/10%FBS/penstrep) into 10 cm Corning tissue culture-treated petri dishes at 50% confluency 16 hours prior to transfection. Cells were removed from the plates with Versene buffer (0.5 mM NaEDTA in PBS) without trypsin for all procedures. Before transfection, the plates were washed once with serum-free DMEM. Fifteen micrograms of each plasmid were added to 5 ml transfection buffer (DMEM with 20 µg/ml DEAE-Dextran and 0.5 mM chloroquine) on each plate. After 1.5 hours incubation at 37° C., the cells were shocked for 1 minute with 5 ml DMEM/10% DMSO. This DMSO solution was then replaced with 10 ml/plate culture medium.

Resulting transfectants were analyzed by ELISA, FACS, and immunoprecipitation as described in Examples 8, 9, and 10.

EXAMPLE 8

ELISA Analysis of COS Transfectants

In order to determine if the COS cells co-transfected with CD18 expression plasmid pRC.CD 18 and an $\alpha_d$ plasmid expressed $\alpha_d$ on the cell surface in association with CD18, ELISAs were performed using primary antibodies raised against CD18 (e.g., TS1/18 purified from ATCC HB203). As a positive control, ELISAs were also performed on cells co-transfected with the CD18 expression plasmid and a CD11a expression plasmid, pDC.CD 11A. The primary antibodies in this control included CD18 antibodies and anti-CD11a antibodies (e.g., TS1/22 purified from ATCC HB202).

For ELISA, cells from each plate were removed with Versene buffer and transferred to a single 96-well flat-bottomed Corning tissue culture plate. Cells were allowed to incubate in culture media 2 days prior to assay. The plates were then washed twice with 150 µl/well D-PBS/0.5% teleost skin gelatin (Sigma) solution. This buffer was used in all steps except during the development. All washes and incubations were performed at room temperature. The wells were blocked with gelatin solution for 1 hour. Primary antibodies were diluted to 10 µg/ml in gelatin solution and 50 µl were then added to each well. Triplicate wells were set up for each primary antibody. After 1 hour incubation, plates were washed 3X with 150 µl/well gelatin solution. Secondary antibody (goat anti-mouse Ig/HRP-Fc specific [Jackson, West Grove, Pa.]) at a 1:3500 dilution was added at 50 µl/well and plates were incubated for 1 hour. After three washes, plates were developed for 20 minutes with 100 µl/well o-phenyldiamine (OPD) (Sigma) solution (1 mg/ml OPD in citrate buffer) before addition of 50 µl/well 15% sulfuric acid.

Analysis of transfectants in the ELISA format with anti-CD18 specific antibodies revealed no significant expression above background in cells transfected only with the plasmid encoding CD18. Cells co-transfected with plasmid containing CD11a and CD18 showed an increase in expression over background when analyzed with CD18 specific antibodies or with reagents specific for CD11a. Further analysis of cells co-transfected with plasmids encoding CD18 and one of the $\alpha_d$ expression constructs (pATM.C10 or pATM.D12)

revealed that cell surface expression of CD18 was rescued by concomitant expression of $\alpha_d$. The increase in detectable CD18 expression in COS cells transfected with pATM.C10 or pATM.D12 was comparable to that observed in co-transfected CD11a/CD 18 positive control cells.

EXAMPLE 9

FACS Analysis of COS Transfectants

For FACS analysis, cells in petri dishes were fed with fresh culture medium the day after transfection and allowed to incubate 2 days prior to the assay. Transfectant cells were removed from the plates with 3 ml Versene, washed once with 5 ml FACS buffer (DMEM/2% FBS/0.2% sodium azide) and diluted to 500,000 cells/sample in 0.1 ml FACS buffer. Ten microliters of either 1 mg/ml FITC-conjugated CD18, CD11a, or CD11b specific antibodies (Becton Dickinson) or 800 µg/ml CFSE-conjugated murine 23F2G (anti-CD18) (ATCC HB11081 ) were added to each sample. Samples were then incubated on ice for 45 minutes, washed 3X with 5 ml/wash FACS buffer and resuspended in 0.2 ml FACS buffer. Samples were processed on a Becton Dickinson FACscan and the data analyzed using Lysys II software (Becton Dickinson).

COS cells transfected with CD18 sequences only did not stain for CD18, CD11a or CD11b. When co-transfected with CD11a/CD18, about 15% of the cells stained with antibodies to CD11a or CD18. All cells transfected with CD18 and any $\alpha_d$ construct resulted in no detectable staining for CD11a and CD11b. The pATM.B1, pATM.C10 and pATM.D12 groups stained 4%, 13% and 8% positive for CD 18, respectively. Fluorescence of the positive population in the CD11a/CD18 group was 4-fold higher than background. In comparison, the co-transfection of $\alpha_d$ constructs with the CD18 construct produced a positive population that showed a 4- to 7-fold increase in fluorescence intensity over background.

EXAMPLE 10

Biotin-Labeled Immunoprecipitation of Human $\alpha d$/CD18 Complexes from Co-transfected COS Cells Immunoprecipitation was attempted on cells co-transfected with CD18 and each of the $\alpha_d$ expression plasmids separately described in Example 7 in order to determine if $\alpha_d$ could be isolated as part of the $\alpha\beta$ heterodimer complex characteristic of integrins.

Transfected cells (1–3×10⁸ cells/group) were removed from petri dishes with Versene buffer and washed 3 times in 50 ml/group D-PBS. Each sample was labeled with 2 mg Sulpho-NHS Biotin (Pierce, Rockford, Ill.) for 15 minutes at room temperature. The reaction was quenched by washing 3 times in 50 ml/sample cold D-PBS. Washed cells were resuspended in 1 ml lysis buffer (1% NP40,50mM Tris-HCl, pH 8.0, 0.2 M NaCl, 2 mM Ca$^{++}$, 2 mM Mg$^{++}$, and protease inhibitors) and incubated 15 minutes on ice. Insoluble material was pelleted by centrifugation at 10,000 g for 5 minutes, and the supernatant removed to fresh tubes. In order to remove material non-specifically reactive with mouse immunoglobulin, a pre-clearance step was initially performed. Twenty-five micrograms of mouse immunoglobulin (Cappel, West Chester, Pa.) was incubated with supernatants at 4° C. After 2.5 hr, 100 µl (25 µg) rabbit anti-mouse Ig conjugated Sepharose (prepared from Protein A Sepharose 4B and rabbit anti-mouse IgG, both from Zymed, San Francisco, Calif.) was added to each sample; incubation was continued at 4° C. with rocking for 16 hours. Sepharose beads were removed from the supernatants by centrifugation. After pre-clearance, the supernatants were then treated with 20 µg anti-CD18 antibody (TS1.18) for 2 hours at 4° C. Antibody/antigen complexes were isolated from supernatants by incubation with 100 µl/sample rabbit anti-mouse/ Protein A-sepharose preparation described above. Beads were washed 4 times with 10 mM HEPES, 0.2M NaCl, and 1% Triton-X 100. Washed beads were pelleted and boiled for 10 minutes in 20 µl 2X Laemmli sample buffer with 2% β-mercaptoethanol. Samples were centrifuged and run on an 8% prepoured Novex polyacrylamide gel (Novex) at 100 V for 30 minutes. Protein was transferred to nitrocellulose membranes (Schleicher & Schuell) in TBS-T buffer at 200 mAmps for 1 hour. Membranes were blocked for 2 hr with 3% BSA in TBS-T. Membranes were treated with 1:6000 dilution of Strep-avidin horse radish peroxidase (POD) (Boehringer Mannheim) for 1 hour, followed by 3 washes in TBS-T. The Amersham Enhanced Chemiluminescence kit was then used according to the manufacturer's instructions to develop the blot. The membrane was exposed to Hyperfilm MP (Amersham) for 0.5 to 2 minutes.

Immunoprecipitation of CD18 complexes from cells transfected with pRC.CD18 and either pATM.B1, pATM.C10 or pATM.D12 revealed surface expression of a heterodimeric species consisting of approximately 100 kD β chain, consistent with the predicted size of CD18, and an α chain of approximately 150 kD, corresponding to $\alpha_d$.

EXAMPLE 11

Stable Transfection of Human $\alpha_d$ in Chinese Hamster Ovary Cells

To determine whether $\alpha_d$ is expressed on the cell surface as a heterodimer in association with CD18, cDNAs encoding each chain were both transiently and stably transfected into a cell line lacking both $\alpha_d$ and CD18.

For these experiments, $\alpha_d$ cDNA was augmented with additional leader sequences and a Kozak consensus sequence, as described in Example 7, and subcloned into expression vector pcDNA3. The final construct, designated pATM.D 12, was co-transfected with a modified commercial vector, pDC1.CD 18 encoding human CD18 into dihydrofolate reductase (DHFR)$^-$ Chinese hamster ovary (CHO) cells. The plasmid pDC1.CD 18 encodes a DHFR$^+$ marker and transfectants can be selected using an appropriate nucleoside-deficient medium. The modifications which resulted in pDC1.CD18 are as follows.

The plasmid pRC/CMV (Invitrogen) is a mammalian expression vector with a cytomegalovirus promoter and ampicillin resistance marker gene. A DHFR gene from the plasmid pSC1190-DHFR was inserted into pRC/CMV 5' of the SV40 origin of replication. In addition, a polylinker from the 5' region of the plasmid pHF2G-DHF was ligated into the pRC/CMV/DHFR construct, 3' to the DHFR gene. CD18 encoding sequences are subsequently cloned into the resulting plasmid between the 5' flanking polylinker region and the bovine growth hormone poly A encoding region.

Surface expression of CD18 was analyzed by flow cytometry using the monoclonal antibody TS1/18. Heterodimer formation detected between $\alpha_d$ and CD18 in this cell line was consistent with the immunoprecipitation described in Example 10 with transient expression in COS cells.

EXAMPLE 12

Human $\alpha_d$ binds to ICAM-R in a CD 18-dependent fashion

In view of reports that demonstrate interactions between the leukocyte integrins and intercellular adhesion molecules (ICAMs) which mediate cell-cell contact [Hynes, *Cell*

69:11–25 (1992)], the ability of CHO cells expressing $\alpha_d$/CD18 to bind ICAM-1, ICAM-R, or VCAM-1 was assessed by two methods.

In replicate assays, soluble ICAM-1, ICAM-R, or VCAM-1 IgG1 fusion proteins were immobilized on plastic and the ability of $\alpha_d$/CD18 CHO transfected cells to bind the immobilized ligand was determined. Transfected cells were labeled internally with calcein, washed in binding buffer (RPMI with 1% BSA), and incubated in either buffer only (with or without 10 ng/ml PMA) or buffer with anti-CD18 monoclonal antibodies at 10 µg/ml. Transfected cells were added to 96-well Immulon 4 microtiter plates previously coated with soluble ICAM-1/IgG1, ICAM-R/IgG1 or VCAM-1/IgG1 fusion protein, or bovine serum albumin (BSA) as a negative control. Design of the soluble forms of these adhesion molecules is described and fully disclosed in co-pending and co-owned U.S. patent application Ser. No. 08/102,852, filed Aug. 5, 1993. Wells were blocked with 1% BSA in PBS prior to addition of labeled cells. After washing the plates by immersion in PBS with 0.1% BSA for 20 minutes, total fluorescence remaining in each well was measured using a Cytofluor 2300 (Millipore, Milford, Mass.).

In experiments with immobilized ICAMs, $\alpha_d$/CD18 cotransfectants consistently showed a 3–5 fold increase in binding to ICAM-R/IgG1 wells over BSA coated wells. The specificity and CD18-dependence of this binding was demonstrated by the inhibitory effects of anti-CD18 antibody TS1/18. The binding of cells transfected with CD11a/CD18 to ICAM-1/IgG1 wells was comparable to the binding observed with BSA coated wells. CD11a/CD18 transfected cells showed a 2–3 fold increase in binding to ICAM-1/IgG1 wells only following pretreatment with PMA. PMA treatment of $\alpha_d$/CD 18 transfectants did not affect binding to ICAM-1/IgG1 or ICAM-R/IgG1 wells. No detectable binding of $\alpha_d$/CD18 transfectants to VCAM-1/IgG1 wells was observed.

Binding of $\alpha_d$/CD18-transfected cells to soluble ICAM-1/IgG1, ICAM-R/IgG1, or VCAM-1/IgG1 fusion proteins was determined by flow cytometry. Approximately one million $\alpha_d$/CD18-transfected CHO cells (grown in spinner flasks for higher expression) per measurement were suspended in 100 µl binding buffer (RPMI and 1% BSA) with or without 10 µg/ml anti-CD18 antibody. After a 20 minute incubation at room temperature, the cells were washed in binding buffer and soluble ICAM-1/IgG1 or ICAM-R/IgG1 fusion protein was added to a final concentration of 5 µg/ml. Binding was allowed to proceed for 30 minute at 37° C., after which the cells were washed three times and resuspended in 100 µl binding buffer containing FITC-conjugated sheep anti-human IgG1 at a 1:100 dilution. After a 30 minute incubation, samples were washed three times and suspended in 200 µl binding buffer for analysis with a Becton Dickinson FACScan.

Approximately 40–50% of the $\alpha_d$/CD18 transfectants indicated binding to ICAM-R/IgG1, but no binding to ICAM-1/IgG1 or VCAM-1/IgG1 proteins. Pretreatment of transfected cells with PMA has no effect on αd/CD18 binding to either ICAM-1/IgG1, ICAM-R/IgG1 or VCAM-1/IgG1, which was consistent with the immobilized adhesion assay. Binding by ICAM-R was reduced to background levels after treatment of $\alpha_d$/CD18 transfectants with anti-CD18 antibody TS1/18.

The collective data from these two binding assays illustrate that $\alpha_{d/CD}18$ binds to ICAM-R and does so preferentially as compared to ICAM-1 and VCAM-1. The αd/CD18 binding preference for ICAM-R over ICAM-1 is opposite that observed with CD11a/CD18 and CD11b/CD18. Thus modulation of $\alpha_d$/CD18 binding may be expected to selectively affect normal and pathologic immune function where ICAM-R plays a prominent role. Moreover, results of similar assays, in which antibodies immunospecific for various extracellular domains of ICAM-R were tested for their ability to inhibit binding of ICAM-R to $\alpha_d$/CD18 transfectants, indicated that $\alpha_d$/CD18 and CD11a/CD18 interact with different domains of ICAM-R.

The failure of CD11a/CD18 to bind ICAM-1/IgG1 or ICAM-R/IgG1 in solution suggests that the affinity of binding between CD11a/CD18 and ICAM-1 or ICAM-R is too low to permit binding in solution. Detection of $\alpha_d$/CD18 binding to ICAM-R/IgG1, however, suggests an unusually high binding affinity.

EXAMPLE 13

Screening by Scintillation Proximity Assay

Specific inhibitors of binding between the $\alpha_d$ ligands of the present invention and their binding partners ($\alpha_d$ ligand/anti-ligand pair) may be determined by a variety of means, such as scintillation proximity assay techniques as generally described in U.S. Pat. No. 4,271,139, Hart and Greenwald, *Mol. Immunol.* 12:265–267 (1979), and Hart and Greenwald, *J. Nuc. Med.* 20:1062–1065 (1979), each of which is incorporated herein by reference.

Briefly, one member of the $\alpha_d$ ligand/anti-ligand pair is bound to a solid support. A fluorescent agent is also bound to the support. Alternatively, the fluorescent agent may be integrated into the solid support as described in U.S. Pat. No. 4,568,649, incorporated herein by reference. The non-support bound member of the $\alpha_d$ ligand/anti-ligand pair is labeled with a radioactive compound that emits radiation capable of exciting the fluorescent agent. When the ligand binds the radiolabeled anti-ligand, the label is brought sufficiently close to the support-bound fluorescer to excite the fluorescer and cause emission of light. When not bound, the label is generally too distant from the solid support to excite the fluorescent agent, and light emissions are low. The emitted light is measured and correlated with binding between the ligand and the anti-ligand. Addition of a binding inhibitor to the sample will decrease the fluorescent emission by keeping the radioactive label from being captured in the proximity of the solid support. Therefore, binding inhibitors may be identified by their effect on fluorescent emissions from the samples. Potential anti-ligands to $\alpha_d$ may also be identified by similar means.

EXAMPLE 14

Soluble Human $\alpha_d$ Expression Constructs

The expression of full-length, soluble human $\alpha_d$/CD18 heterodimeric protein provides easily purified material for immunization and binding assays. The advantage of generating soluble protein is that it can be purified from supernatants rather than from cell lysates (as with full-length membrane-bound $\alpha_d$/CD18); recovery in therefore improved and impurities reduced.

The soluble $\alpha_d$ expression plasmid was constructed as follows. A nucleotide fragment corresponding to the region from bases 0 to 3161 in SEQ ID NO: 1, cloned into plasmid pATM.D12, was isolated by digestion with HindIII and AatII. A PCR fragment corresponding to bases 3130 to 3390 in SEQ ID NO: 1, overlapping the HindIII/AatII fragment and containing an addition MluI restriction site at the 3' terminus, was amplified from pATM.D12 with primers sHAD.5 and sHAD.3 set out in SEQ ID NOS: 30 and 31, respectively.

TTGCTGACTGCCTGCAGTTC  (SEQ ID NO: 30)

GTTCTGACGCGTAATGGCATTGTAGACCTCGTCTTC (SEQ ID NO: 31)

The PCR amplification product was digested with AatII and MluI and ligated to the HindIII/AatII fragment. The resulting product was ligated into HindIII/MluI-digested plasmid PDC.1s.

This construct is co-expressed with soluble CD18 in stably transfected CHO cells, and expression is detected by autoradiographic visualization of immunoprecipitated CD18 complexes derived from $^{35}$S-methionine labeled cells.

Soluble Human $\alpha_d$ I Domain Expression Constructs

It has previously been reported that the I domain in CD11a can be expressed as an independent structural unit that maintains ligand binding capabilities and antibody recognition [Randi and Hogg, *J. Biol. Chem.* 269:12395–12398 (1994); Zhout, et al., *J. Biol. Chem.* 269:17075–17079 (1994)]]. To generate a soluble fusion protein comprising the $\alpha_d$ I domain and human IgG4, the $\alpha_d$ I domain is amplified by PCR using primers designed to add flanking BamHI and XhoI restriction sites to facilitate subcloning. These primers are set out in SEQ ID NOS: 32 and 33 with restriction sites underlined.

ACGTATGCA<u>GGATCC</u>CATCAAGAGATGGACATCGCT (SEQ ID NO: 32)

ACTGCATGT<u>CTCGAG</u>GCTGAAGCCTTCTTGGGACATC (SEQ ID NO: 33)

The C nucleotide immediately 3' to the BamHI site in SEQ ID NO: 32 corresponds to nucleotide 435 in SEQ ID NO: 1; the G nucleotide 3' to the XhoI site in SEQ ID NO: 33 is complementary to nucleotide 1067 in SEQ ID NO: 1. The amplified I domain is digested with the appropriate enzymes, the purified fragment ligated into the mammalian expression vector pDCs and the prokaryotic expression vector pGEX-4T-3 (Pharmacia) and the I domain fragment sequenced. The fusion protein is then expressed in COS, CHO or *E. coli* cells transfected or transformed with an appropriate expression construct.

Given the affinity of $\alpha_d$ for ICAM-R, expression of the $\alpha_d$ I domain may be of sufficient affinity to be a useful inhibitor of cell adhesion in which $\alpha_d$ participates.

EXAMPLE 15

Production of Human $\alpha_d$ Monoclonal Antibodies

Transiently transfected cells from Example 7 were washed three times in Dulbecco's phosphate buffered saline (D-PBS) and injected at 5×10⁶ cells/mouse into Balb/c mice with 50 µg/mouse muramyl dipeptidase (Sigma) in PBS. Mice were injected two more times in the same fashion at two week intervals. The pre-bleed and immunized serum from the mice were screened by FACS analysis as outlined in Example 9 and the spleen from the mouse with the highest reactivity to cells transfected with $\alpha_d$/CD18 was fused. Hybridoma culture supernatants were then screened separately for lack of reactivity against COS cells transfected with CD11a/CD18 and for reactivity with cells cotransfected with an $\alpha_d$ expression plasmid and CD18.

This method resulted in no monoclonal antibodies.

As an alternative, monoclonal antibodies are generated as follows. Affinity purified $\alpha_d$/CD 18 heterodimeric protein from detergent lysates of stably transfected CHP cells is used with 50 µg/ml muramyl dipeptidase to immunize Balb/c mice as described above. Mice receive three immunizations before serum reactivity against $\alpha_d$/CD18 is determined by immunoprecipitation of biotinylated complexes in the CHO transfectants. Hybridomas from positive animals are established according to standard protocols, after which hybridoma cultures are selected by flow cytometry using $\alpha_d$/CD18 transfectants. CD11a/CD18 transfectants are utilized to control for CD18-only reactivity.

As another alternative for production of monoclonal antibodies, soluble $\alpha_d$ I domain IgG4 fusion protein is affinity purified from supernatant of stably transfected CHO cells and used to immunized Balb/c mice as described above. Hybridomas are established and supernatant from these hybridomas are screened by ELISA for reactivity against $\alpha_d$ I domain fusion protein. Positive cultures are then analyzed for reactivity with full length $\alpha_d$/CD18 complexes expressed on CHO transfectants.

As another alternative for monoclonal antibody production, Balb/c mice undergo an immunization/immunosuppression protocol designed to reduce reactivity to CHO cell determinants on transfectants used for immunization. This protocol involves immunization with untransfected CHO cells and subsequent killing of CHO-reactive B-cell blasts with cyclophosphamide treatment. After three rounds of immunization and cyclophosphamide treatment are performed, the mice are immunized with $\alpha_d$/CD18 CHO transfected cells as described above.

EXAMPLE 16

Isolation of Rat cDNA Clones

In view of the existence of both canine and human $\alpha_d$ integrins, attempts were made to isolate homologous genes in other species, including rat (this example) and mouse (Example 17, infra).

A partial sequence of a rat cDNA showing homology to the human $\alpha_d$ gene was obtained from a rat splenic λgt10 library (Clontech). The library was plated at 2×10⁴ pfu/plate onto 150 mm LBM/agar plates. The library was lifted onto Hybond membranes (Amersham), denatured 3 minutes, neutralized 3 minutes and washed 5 minutes with buffers as described in standard protocols [Sambrook, et al., *Molecular Cloning: a laboratory manual*, p.2.110]. The membranes were placed immediately into a Stratalinker (Stratagene) and the DNA crosslinked using the autocrosslinking setting. The membranes were prehybridized and hybridized in 30% or 50% formamide, for low and high stringency conditions, respectively. Membranes were initially screened with a $^{32}$P-labeled probe generated from the human $\alpha_d$ cDNA, corresponding to bases 500 to 2100 in clone 19A2 (SEQ ID NO: 1). The probe was labeled using Boehringer Mannheim's Random Prime Kit according to manufacturer's suggested protocol. Filters were washed with 2X SSC at 55° C.

Two clones, designated 684.3 and 705.1, were identified which showed sequence homology to human $\alpha_d$, human CD11b, and human CD11c. Both clones aligned to the human $\alpha_d$ gene in the 3' region of the gene, starting at base 1871 and extending to base 3012 for clone 684.3, and bases 1551 to 3367 for clone 705.1.

In order to isolate a more complete rat sequence which included the 5' region, the same library was rescreened using the same protocol as employed for the initial screening, but using a mouse probe generated from clone A1160 (See Example 17, infra). Single, isolated plaques were selected from the second screening and maintained as single clones on LBM/agar plates. Sequencing primers 434FL and 434FR (SEQ ID NOS: 34 and 35, respectively) were used in a standard PCR protocol to generate DNA for sequencing.

434FL (SEQ ID NO: 34)

TATAGACTGCTGGGTAGTCCCCAC

434FR (SEQ ID NO: 35)

TGAAGATTGGGGGTAAATACAGA

DNA from the PCR was purified using a Quick Spin Column (Qiagen) according to manufacturer's suggested protocol.

Two clones, designated 741.4 and 741.11, were identified which overlapped clones 684.3 and 705.1; in the overlapping regions, clones 741.1 and 741.11 were 100% homologous to clones 684.3 and 705.1. A composite rat cDNA having homology to the human $\alpha_d$ gene is set out in SEQ ID NO: 36; the predicted amino acid sequence is set forth in SEQ ID NO: 37.

Characteristics of the Rat cDNA and Amino Acid Sequences

Neither nucleic acid nor amino acid sequences have previously been reported for rat $\alpha$ subunits in $\beta_2$ integrins. However sequence comparisons to reported human $\beta_2$ integrin $\alpha$ subunits suggests that the isolated rat clone and its predicted amino acid sequence are most closely related to $\alpha_d$ nucleotide and amino acid sequences.

At the nucleic acid level, the isolated rat cDNA clone shows 80% identity in comparison to the human $\alpha_d$ cDNA; 68% identity in comparison to human CD11b; 70% identity in comparison to human CD11c; and 65% identity in comparison to mouse CD11b. No significant identity is found in comparison to human CD11a and to mouse CD11a.

At the amino acid level, the predicted rat polypeptide encoded by the isolated cDNA shows 70% identity in comparison to human $\alpha_d$ polypeptide; 28% identity in comparison to human CD11a; 58% identity in comparison to human CD11b; 61% identity in comparison to human CD11c; 28% identity in comparison to mouse CD11a; and 55% identity in comparison to mouse CD11b.

EXAMPLE 17

Isolation of Mouse cDNA Clones

Isolation of a mouse cDNA exhibiting homology to human $\alpha_d$ by cross-species hybridization was attempted with two PCR-generated probes: a 1.5 kb fragment corresponding to bases 522 to 2047 from human clone 19A2 (SEQ ID NO: 1), and a 1.0 kb rat fragment which corresponds to bases 1900 to 2900 in human clone 19A2 (SEQ ID NO: 1). The human probe was generated by PCR using primer pairs designated ATM-2 and 9–10.1 set out in SEQ ID NOS: 38 and 9, respectively; the rat probe was generated using primer pairs 434L and 434R, set out in SEQ ID NOS: 34 and 35, respectively. Samples were incubated at 4° C. for 4 minutes and subjected to 30 cycles of the temperature step sequence: 4° C.; 50° C. 2 minutes; 72° C., 4 minutes.

ATM-2 (SEQ ID NO: 38)

5'-GTCCAAGCTGTCATGGGCCAG-3'

9-10.1 (SEQ ID NO: 39)

5'-GTCCAGCAGACTGAAGAGCACGG-3'

The PCR products were purified using the Qiagen Quick Spin kit according to manufacturer's suggested protocol, and approximately 180 ng DNA was labeled with 200 µCi [$^{32}$P]-dCTP using a Boehringer Mannheim Random Primer Labeling kit according to manufacturer's suggested protocol. Unincorporated isotope was removed using a Centri-sep Spin Column (Princeton Separations, Adelphia, N.J.) according to manufacturer's suggested protocol. The probes were denatured with 0.2N NaOH and neutralized with 0.4M Tris-HCl, pH 8.0, before use.

A mouse thymic oligo dT-primed cDNA library in lambda ZAP II (Stratagene) was plated at approximately 30,000 plaques per 15 cm plate. Plaque lifts on nitrocellulose filters (Schleicher & Schuell, Keene, N.H.) were incubated at 50° C. with agitation for 1 hour in a prehybridization solution (8 ml/lift) containing 30% formamide. Labeled human and rat probes were added to the prehybridization solution and incubation continued overnight at 50° C. Filters were washed twice in 2X SSC/0.1% at room temperature, once in 2X SSC/0.1% SDS at 37° C., and once in 2X SSC/0.1% SDS at 42° C. Filters were exposed on Kodak X-Omat AR film at −80° C. for 27 hours with an intensifying screen.

Four plaques giving positive signals on duplicate lifts were restreaked on LB medium with magnesium (LBM)/carbenicillin (100 mg/ml) plates and incubated overnight at 37° C. The phage plaques were lifted with Hybond filters (Amersham), probed as in the initial screen, and exposed on Kodak X-Omat AR film for 24 hours at −80° C. with an intensifying screen.

Twelve plaques giving positive signals were transferred into low $Mg^{++}$ phage diluent containing 10 mM Tris-HCl and 1 mM MgCl$_2$. Insert size was determined by PCR amplification using T3 and T7 primers (SEQ ID NOS: 13 and 14, respectively) and the following reaction conditions. Samples were incubated at 94° C. for 4 minutes and subjected to 30 cycles of the temperature step sequence: 94° C., for 15 seconds; 50° C., for 30 seconds; and 72° C. for 1 minute.

Six samples produced distinct bands that ranged in size from 300 bases to 1 kb. Phagemids were released via co-infection with helper phage and recircularized to generate Bluescript SK$^-$ (Stratagene). The resulting colonies were cultured in LBM/carbenicillin (100 mg/ml) overnight. DNA was isolated with a Promega Wizard miniprep kit (Madison, Wis.) according to manufacturer's suggested protocol. EcoRI restriction analysis of purified DNA confirmed the molecular weights which were detected using PCR. Insert DNA was sequenced with M13 and M13 reverse. 1 primers set out in SEQ ID NOS: 40 and 41, respectively.

5'-TGTAAAACGACGGCCAGT-3' (SEQ ID NO: 40)

5'-GGAAACAGCTATGACCATG-3' (SEQ ID NO: 41)

Sequencing was performed as described in Example 4.

Of the six clones, only two, designated 10.3-1 and 10.5-2, provided sequence information and were identical 600 bp fragments. The 600 bp sequence was 68% identical to a corresponding region of human $\alpha_d$, 40% identical to human CD11a, 58% identical to human CD11c, and 54% identical to mouse CD11b. This 600 bp fragment was then utilized to isolate a more complete cDNA encoding a putative mouse $\alpha_d$ homolog.

A mouse splenic cDNA library (oligo dT$^-$ and random-primed) in lambda Zap II (Stratagene) was plated at 2.5×10$^4$ phage/15 cm LBM plate. Plaques were lifted on Hybond nylon transfer membranes (Amersham), denatured with 0.5M NaOH/1.5M NaCl, neutralized with 0.5M Tris Base/1.5M NaCl/11.6 HCl, and washed in 2X SSC. The DNA was cross-linked to filters by ultraviolet irradiation.

Approximately 500,000 plaques were screened using probes 10.3-1 and 10.5-2 previously labeled as described supra. Probes were added to a prehybridization solution and incubated overnight at 50° C. The filters were washed twice in 2X SSC/0.1% SDS at room temperature, once in 2X SSC/0.1% SDS at 37° C., and once in 2X SSC/0.1% SDS at 42° C. Filters were exposed on Kodak X-Omat AR film for 24 hours at −80° C. with an intensifying screen. Fourteen plaques giving positive signals on duplicate lifts were subjected to a secondary screen identical to that for the initial screen except for additional final high stringency washes in 2X SSC/0.1% SDS at 50° C., in 0.5X SSC/0.1% SDS at 50° C., and at 55° C. in 0.2X SSC/0.1% SDS. The filters were exposed on Kodak X-Omat AR film at −80° C. for 13 hours with an intensifying screen.

Eighteen positive plaques were transferred into low $Mg^{++}$ phage diluent and insert size determined by PCR amplification as described above. Seven of the samples gave single bands that ranged in size from 600 bp to 4 kb. EcoRI restriction analysis of purified DNA confirmed the sizes observed from PCR and the DNA was sequenced with primers M13 and M13 reverse. 1 (SEQ ID NOS: 40 and 41, respectively).

One clone designated B3800 contained a 4 kb insert which corresponded to a region 200 bases downstream of the 5' end of the human $\alpha_d$ 19A2 clone and includes 553 bases of a 3' untranslated region. Clone B3800 showed 77% identity to a corresponding region of human $\alpha_d$, 44% identity to a corresponding region of human CD11a, 59% identity to a corresponding region of human CD11c, and 51% identity to a corresponding region of mouse CD11b. The second clone A1160 was a 1.2 kb insert which aligned to the 5' end of the coding region of human $\alpha_d$ approximately 12 nucleic acids downstream of the initiating methionine. Clone A1160 showed 75% identity to a corresponding region of human $\alpha_d$, 46% identity to a corresponding region of human CD11a, 2% identity to a corresponding region of human CD11c, and 66% identity to a corresponding region of mouse CD11b.

Clone A1160, the fragment closer to the 5' end of human clone 19A2, is 1160 bases in length, and shares a region of overlap with clone B3800 starting at base 205 and continuing to base 1134. Clone A1160 has a 110-base insertion (bases 704–814 of clone A 1160) not present in the overlapping region of clone B3800. This insertion occurs at a probable exon-intron boundary [Fleming, et al., *J. Immunol.* 150:480–490 (1993)] and was removed before subsequent ligation of clones A1160 and B3800.

Rapid Amplification of 5' cDNA End of the Putative Mouse $\alpha_d$ Clone

RACE PCR [Frohman, "RACE: Rapid Amplification of cDNA Ends," in PCR Protocols: A Guide to Methods and Applications, Innis, et al. (eds.) pp. 28–38, Academic Press:New York (1990)] was used to obtain missing 5' sequences of the putative mouse $\alpha_d$ clone, including 5' untranslated sequence and initiating methionine. A mouse splenic RACE-Ready kit (Clontech, Palo Alto, Calif.) was used according to the manufacturer's suggested protocol. Two antisense, gene-specific primers (SEQ ID NOS: 42 and 43) were designed to perform primary and nested PCR.

| A1160 RACE1-primary | (SEQ ID NO: 42) |

5'-GGACATGTTCACTGCCTCTAGG-3'

| A1160 RACE2-nested | (SEQ ID NO: 43) |

5'-GGCGGACAGTCAGACGACTGTCCTG-3'

The primers, SEQ ID NOS: 42 and 43, correspond to regions starting 302 and 247 bases from the 5' end, respectively. PCR was performed as described, supra, using the 5' anchor primer (SEQ ID NO: 44) and mouse spleen cDNA supplied with the kit.

| 5' anchor primer | (SEQ ID NO: 44) |

CTGGTTCGGCCCACCTCTGAAGGTTCCAGAATCGATAG

Electrophoresis of the PCR product revealed a band approximately 280 bases in size, which was subcloned using a TA cloning kit (Invitrogen) according to manufacturer's suggested protocol. Ten resulting colonies were cultured, and the DNA isolated and sequenced. An additional 60 bases of 5' sequence were identified by this method, which correspond to bases 1 to 60 in SEQ ID NO: 45.

Characteristics of the Mouse cDNA and Predicted Amino Acid Sequence

A composite sequence of the mouse cDNA encoding a putative homolog of human $\alpha_d$ is set out in SEQ ID NO: 45. Although homology between the external domains of the human and mouse clones is high, homology between the cytoplasmic domains is only 30%. The observed variation may indicate C-terminal functional differences between the human and mouse proteins. Alternatively, the variation in the cytoplasmic domains may result from splice variation, or may indicate the existence of an additional $\beta_2$ integrin gene(s).

At the amino acid level, the mouse cDNA predicts a protein (SEQ ID NO: 46) with 28% identity to mouse CD11a, 53% identity to mouse CD11b, 28% identity to human CD11a, 55% identity to human CD11b, 59% identity to human CD11c, and 70% identity to human $\alpha_d$. Comparison of the amino acid sequences of the cytoplasmic domains of human $\alpha_d$ and the putative mouse homolog indicates regions of the same length, but having divergent primary structure. Similar sequence length in these regions suggests species variation rather than splice variant forms. In comparison to the predicted rat polypeptide, Example 16,supra, however, mouse and rat cytoplasmic domains show greater than 60% identity.

EXAMPLE 18

In situ hybridizations in Mouse

A single stranded 200 bp mRNA probe was generated from a DNA template, corresponding to nucleotides 3460 to 3707 in the cytoplasmic tail region of the murine cDNA, by in vitro RNA transcription incorporating 35S-UTP (Amersham).

Whole mouse embryos (harvested at days 11–18 after fertilization) and various mouse tissues, including spleen, kidney, liver, intestine, and thymus, were hybridized in situ with the radiolabeled single-stranded mRNA probe.

Tissues were sectioned at 6 μm thickness, adhered to Vectabond (Vector Laboratories, Inc., Burlingame, Calif.) coated slides, and stored at −70° C. Prior to use, slides were removed from −70° C. and placed at 50° C. for approximately 5 minutes. Sections were fixed in 4% paraformaldehyde for 20 minutes at 4° C., dehydrated with an increasing ethanol gradient (70–95–100%) for 1 minute at 4° C. at each concentration, and air dried for 30 minutes at room temperature. Sections were denatured for 2 minutes at 70° C. in 70% formamide/2X SSC, rinsed twice in 2X SSC, dehydrated with the ethanol gradient described supra and air dried for 30 minutes. Hybridization was carried out overnight (12–16 hours) at 55° C. in a solution containing $^{35}$S-labeled riboprobes at 6×10$^5$ cpm/section and diethylpyrocarbonate (DEPC)-treated water to give a final concentration of 50% formamide, 0.3M NaCl, 20 mM Tris-HCl, pH 7.5, 10% dextran sulfate, 1X Denhardt's solution, 100 mM dithiothreitol (DTT) and 5 mM EDTA. After hybridization, sections were washed for 1 hour at room temperature in 4X SSC/10 mM DTT, 40 minutes at 60° C. in 50% formamide/ 2X SSC/10 mM DTT, 30 minutes at room temperature in 2X SSC, and 30 minutes at room temperature in 0.1X SSC. The sections were dehydrated, air dried for 2 hours, coated with Kodak NTB2 photographic emulsion, air dried for 2 hours, developed (after storage at 4° C. in complete darkness) and counter-stained with hematoxylin/eosin.

Spleen tissue showed a strong signal primarily in the red pulp. This pattern is consistent with that of tissue macrophage distribution in the spleen, but does not exclude other cell types.

EXAMPLE 19

Generation of Mouse Expression Constructs

In order to construct an expression plasmid including mouse cDNA sequences exhibiting homology to human $\alpha_d$, inserts from clones A1160 and B3800 were ligated. Prior to this ligation, however, a 5' leader sequence, including an initiating methionine, was added to clone A1160. A primer designated "5' PCR leader" (SEQ ID NO: 47) was designed to contain: (1) identical nonspecific bases at positions 1–6 allowing for digestion; (2) a BamHI site (underlined in SEQ ID NO: 47) from positions 7–12 to facilitate subcloning into an expression vector; (3) a consensus Kozak sequence from positions 13–18, (4) a signal sequence including a codon for an initiating methionine (bold in SEQ ID NO: 47), and (5) an additional 31 bases of specifically overlapping 5' sequence from clone A1160 to allow primer annealing. A second primer designated "3' end frag" (SEQ ID NO: 48) was used with primer "5' PCR leader" to amplify the insert from clone A1160.

| 5' PCR leader | (SEQ ID NO: 47) |
|---|---|

5'-AGTTACGGATCCGGCACCATGACCTTCG-
GCACTGTGATCCTCCTGTGTG-3'

| 3' end flag | (SEQ ID NO: 48) |
|---|---|

5'-GCTGGACGATGGCATCCAC-3'

The resulting PCR product did not digest with BamHI, suggesting that an insufficient number of bases preceded the restriction site, prohibiting recognition by the enzyme. The length of the "tail" sequence preceding the BamHI site in the 5' primer (SEQ ID NO: 47) was increased and PCR was repeated on the amplification product from the first PCR. A 5' primer, designated mAD.5'.2 (SEQ ID NO: 49), was designed with additional nonspecific bases at positions 1–4 and an additional 20 bases specifically overlapping the previously employed "5' PCR leader" primer sequences.

| mAD.5'.2 | (SEQ ID NO: 49) |
|---|---|

5'-GTAGAGTTACGGATCCGGCACCAT-3'

Primers "mAD.5'. 2" and "3' end frag" were used together in PCR with the product from the first amplification as template. A resulting secondary PCR product was subcloned into plasmid pCRtmII (Invitrogen) according to manufacturer's suggested protocol and transformed into competent Oneshot cells (Invitrogen). One clone containing the PCR product was identified by restriction enzyme analysis using BamHI and EcoRI and sequenced. After the sequence was verified, the insert was isolated by digestion with BamHI and EcoRI and gel purified.

The insert from clone B3800 was isolated by digestion with EcoRI and NotI, gel purified, and added to a ligation reaction which included the augmented A1160 BamHI/EcoRI fragment. Ligation was allowed to proceed for 14 hours at 14° C. Vector pcDNA.3 (Invitrogen), digested with BamHi and NotI, was added to the ligation reaction with additional ligase and the reaction was continued for another 12 hours. An aliquot of the reaction mixture was transformed into competent *E. coli* cells, the resulting colonies cultured, and one positive clone identified by PCR analysis with the primers 11.b-½FOR1 and 11.b-½REV11 (SEQ ID NOS: 50 and 51, respectively).

| 5'-GCAGCCAGCTTCGGACAGAC-3' | (SEQ ID NO: 50) |
|---|---|
| 5'-CCATGTCCACAGAACAGAGAG-3' | (SEQ ID NO: 51) |

These primers bridge the A1160 and B3800 fragments, therefore detection of an amplification product indicates the two fragments were ligated. The sequence of the positive clone was verified with the primers set out in SEQ ID NOS: 50 and 51, which amplify from base 100 to 1405 after the initiating methionine.

EXAMPLE 20

Construction of a Knock-out Mouse

In order to more accurately assess the immunological role of the protein encoded by the putative mouse $\alpha_d$ cDNA, a "knock-out" mouse is designed wherein the genomic DNA sequence encoding the putative $\alpha_d$ homolog is disrupted by homologous recombination. The significance of the protein encoded by the disrupted gene is thereby assessed by the absence of the encoded protein.

Design of such a mouse begins with construction of a plasmid containing sequences to be "knocked out" by homologous recombination events. A 750 base pair fragment of the mouse cDNA (corresponding to nucleotides 1985 to 2733 in SEQ ID NO: 45)was used to identify a mouse genomic sequence encoding the putative mouse $\alpha_d$ homolog from a λFIX library. Primary screening resulted in 14 positive plaques, seven of which were confirmed by secondary screening. Liquid lysates were obtained from two of the plaques giving the strongest signal and the α DNA was isolated by conventional methods. Restriction mapping and Southern analysis confirmed the authenticity of one clone, designated 14-1, and the insert DNA was isolated by digestion with NotI. This fragment was cloned into Bluescript SKII⁺.

In order to identify a restriction fragment of approximately 9 to 14 kb, a length reported to optimize the probability of homologous recombination events, Southern hybridization was performed with the 750 bp cDNA probe. Prior to hybridization, a restriction map was constructed for clone 14-1. A 12 kb fragment was identified as a possible candidate and this fragment was subcloned into pBluescript SKII⁺ in a position wherein the mouse DNA is flanked by thymidine kinase encoding cassettes.

A neomycin resistance (neo$^r$) gene is then inserted into the resulting plasmid in a manner that interrupts the protein coding sequence of the genomic mouse DNA. The resulting plasmid therefore contains a neo$^r$ gene within the mouse genomic DNA sequences, all of which are positioned within a thymidine kinase encoding region. Plasmid construction in this manner is required to favor homologous recombination over random recombination [Chisaka, et al., *Nature* 355:516–520 (1992)].

Numerous modifications and variations in the invention as set forth in the above illustrative examples are expected to occur to those skilled in the art. Consequently only such limitations as appear in the appended claims should be placed on the invention.

---

What is claimed is:

1. A purified and isolated $\alpha_d$ extracellular domain polypeptide fragment consisting of about amino acid 17 to about amino acid 1108 of the human $\alpha_d$ amine acid sequence set out in SEQ IN NO: 2.1

2. A purified and isolated $\alpha_d$ I domain polypeptide fragment consisting of about amine acid 145 to about amino acid of the human $\alpha_d$ amine acid sequence set out in SEQ ID NO: 2.

3. A fusion protein comprising an $\alpha_d$ extracellular domain polypeptide fragment and immunoglobulin constant domain sequences, said $\alpha_d$ extracellular domain polypeptide fragment consisting of about amino acid 17 to about amino acid 1108 of SEQ ID NO: 2.

4. A purified and isolated $\alpha_d$ I domain polypeptide fragment consisting of about amino acid 150 to about amino acid 352 of the human $\alpha_d$ amino acid sequence set out in SEQ ID NO: 2.

5. A purified and isolated $\alpha_d$ polypeptide consisting of the amino acid sequence set out in SEQ ID NO: 2.

* * * * *

UNITED STATES PATENT AND TRADEMARK OFFICE
CERTIFICATE OF CORRECTION

PATENT NO. : 5,470,953  Page 1 of 3
DATED : November 28, 1995
INVENTOR(S) : Gallatin et al.

It is certified that error appears in the above-identified patent and that said Letters Patent is hereby corrected as shown below: ON THE TITLE PAGE:

Col. 1, Chisaka, et al.: Please delete "355-516-520", and insert - -355:516-520--.

Col. 2, Danilenko et al.: Please delete "CD11/CE18", and insert - -CD11/CD18- -.

Col. 1, line 3: Please delete "in-pan", and insert - -in-part- -.

Col. 2, line 66: Please delete "Cd11a", and insert - -CD11a- -.

Col. 10, line 7: Please delete "TRYAAYYTGGAYGTNGAROARCCNATGGTNTTYCA", and insert - -TTYAAYYTGGAYGTNGARGARCCNATGGTNTTYCA- -.

Col 10, line 17: Please delete "dam", and insert - -data- -.

Col 11, line 29: Please delete "20 rain", and insert - -20 min.- -

Col 11, line 30: Please delete "Coming (Coming, N.Y.)", and insert - -Corning (Corning, N.Y.)- -.

Col. 11, line 31: Please delete "Coming 0.8", and insert - -Corning 0.8- -.

Col. 13, line 29: Please delete "$_{cDNA}$", and insert - -cDNA- -.

Col. 15, lines 43: Please delete "β", and insert - -$β_2$- -.

Col. 15, lines 56: Please delete "β", and insert - -$β_2$- -.

Col. 15, lines 59: Please delete "β", and insert - -$β_2$- -.

Col. 17, line 64: Please delete "$α_d$%", and insert - -$α_d$,- -.

UNITED STATES PATENT AND TRADEMARK OFFICE
CERTIFICATE OF CORRECTION

PATENT NO. : 5,470,953
DATED : November 28, 1995
INVENTOR(S) : Gallatin et al.

It is certified that error appears in the above-identified patent and that said Letters Patent is hereby corrected as shown below:

Col. 21, line 58: Please delete "αd/CD18", and insert - -$\alpha_d$/CD18- -.

Col. 21, line 65: Please delete "αd/CD18", and insert - -$\alpha_d$/CD18- -.

Col. 21, line 66: Please delete "αd/CD18", and insert - -$\alpha_d$/CD18- -.

Col. 25, line 13: Please delete "TGAAGATTGGGGGTAAATACAGA", and insert - - TGAAGATTGGGGGTAAATAACAGA- -.

Col. 25, line 53: Please delete "9", and insert - -39- -.

Col. 25, line 55: Please delete "4$^\circ$C", and insert - -94$^\circ$C- -.

Col. 25, line 57: Please delete "4$^\circ$C", and insert - -94$^\circ$C- -.

Col. 27, line 35: Please delete "2%", and insert - -62%- -.

Col. 27, line 50: Please delete "Press-", and insert - -Press- -.

Col. 28, line 47: Please delete "35S-UTP", and insert - -$^{35}$S-UTP- -.

Col. 29, line 11: Please delete "counter-stained", and insert - -counterstained- -.

Col. 29, line 40: Please delete "ATGGACGGATCCGGCACCATGACCTTCG", and insert - - ATGGACGGATCCGGCACCATGACCTTCG- -.

Col. 29, line 43: Please delete "flag" and insert --frag--.

Col. 30, line 8: Please delete "Bam Hi", and insert - -Bam HI--.

Col. 30, line 44: Please delete "αDNA", and insert - -λDNA- -.

UNITED STATES PATENT AND TRADEMARK OFFICE
CERTIFICATE OF CORRECTION

PATENT NO. : 5,470,953
DATED : November 28, 1995
INVENTOR(S) : Gallatin et al.

It is certified that error appears in the above-identified patent and that said Letters Patent is hereby corrected as shown below:

Col. 30, line 62: Please delete "aneo$^r$", and insert -- a neo$^r$ --

Col. 78, line 5: Please delete "TAGGAATC", and insert -- TAGGAATCCA --.

Col. 101, line 22: Please delete "amine", and insert -- amino --.

Col. 101, line 23: Please delete "2.1", and insert -- 2. --.

Col. 101, line 25: Please delete "amine", and insert -- amino --.

Col. 101, line 27: Please delete "acid of", and insert -- acid 355 of --.

Col. 101, line 26: Please delete "amine", and insert -- amino --.

Signed and Sealed this

Twenty-first Day of November, 2000

Attest:

Q. TODD DICKINSON

*Attesting Officer*   *Director of Patents and Trademarks*

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
        ( A ) LENGTH: 3726 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..3485

( x i ) SEQUENCE DESCRIPTION: SEQ ID NO:1:

```
TG ACC TTC GGC ACT GTG CTT CTT CTG AGT GTC CTG GCT TCT TAT CAT        47
   Thr Phe Gly Thr Val Leu Leu Leu Ser Val Leu Ala Ser Tyr His
   1               5                   10                  15

GGA TTC AAC CTG GAT GTG GAG GAG CCT ACG ATC TTC CAG GAG GAT GCA        95
Gly Phe Asn Leu Asp Val Glu Glu Pro Thr Ile Phe Gln Glu Asp Ala
                20                  25                  30

GGC GGC TTT GGG CAG AGC GTG GTG CAG TTC GGT GGA TCT CGA CTC GTG       143
Gly Gly Phe Gly Gln Ser Val Val Gln Phe Gly Gly Ser Arg Leu Val
            35                  40                  45

GTG GGA GCA CCC CTG GAG GTG GTG GCG GCC AAC CAG ACG GGA CGG CTG       191
Val Gly Ala Pro Leu Glu Val Val Ala Ala Asn Gln Thr Gly Arg Leu
        50                  55                  60

TAT GAC TGC GCA GCT GCC ACC GGC ATG TGC CAG CCC ATC CCG CTG CAC       239
Tyr Asp Cys Ala Ala Ala Thr Gly Met Cys Gln Pro Ile Pro Leu His
        65                  70                  75

ATC CGC CCT GAG GCC GTG AAC ATG TCC TTG GGC CTG ACC CTG GCA GCC       287
Ile Arg Pro Glu Ala Val Asn Met Ser Leu Gly Leu Thr Leu Ala Ala
80                  85                  90                  95

TCC ACC AAC GGC TCC CGG CTC CTG GCC TGT GGC CCG ACC CTG CAC AGA       335
Ser Thr Asn Gly Ser Arg Leu Leu Ala Cys Gly Pro Thr Leu His Arg
                100                 105                 110

GTC TGT GGG GAG AAC TCA TAC TCA AAG GGT TCC TGC CTC CTG CTG GGC       383
Val Cys Gly Glu Asn Ser Tyr Ser Lys Gly Ser Cys Leu Leu Leu Gly
            115                 120                 125

TCG CGC TGG GAG ATC ATC CAG ACA GTC CCC GAC GCC ACG CCA GAG TGT       431
Ser Arg Trp Glu Ile Ile Gln Thr Val Pro Asp Ala Thr Pro Glu Cys
        130                 135                 140

CCA CAT CAA GAG ATG GAC ATC GTC TTC CTG ATT GAC GGC TCT GGA AGC       479
Pro His Gln Glu Met Asp Ile Val Phe Leu Ile Asp Gly Ser Gly Ser
        145                 150                 155

ATT GAC CAA AAT GAC TTT AAC CAG ATG AAG GGC TTT GTC CAA GCT GTC       527
Ile Asp Gln Asn Asp Phe Asn Gln Met Lys Gly Phe Val Gln Ala Val
160                 165                 170                 175

ATG GGC CAG TTT GAG GGC ACT GAC ACC CTG TTT GCA CTG ATG CAG TAC       575
Met Gly Gln Phe Glu Gly Thr Asp Thr Leu Phe Ala Leu Met Gln Tyr
                180                 185                 190

TCA AAC CTC CTG AAG ATC CAC TTC ACC TTC ACC CAA TTC CGG ACC AGC       623
Ser Asn Leu Leu Lys Ile His Phe Thr Phe Thr Gln Phe Arg Thr Ser
            195                 200                 205
```

| | | | | | | | | | | | | | | | | |
|---|---|---|---|---|---|---|---|---|---|---|---|---|---|---|---|---|
| CCG | AGC | CAG | CAG | AGC | CTG | GTG | GAT | CCC | ATC | GTC | CAA | CTG | AAA | GGC | CTG | 671 |
| Pro | Ser | Gln | Gln | Ser | Leu | Val | Asp | Pro | Ile | Val | Gln | Leu | Lys | Gly | Leu | |
| | | 210 | | | | 215 | | | | | 220 | | | | | |
| ACG | TTC | ACG | GCC | ACG | GGC | ATC | CTG | ACA | GTG | GTG | ACA | CAG | CTA | TTT | CAT | 719 |
| Thr | Phe | Thr | Ala | Thr | Gly | Ile | Leu | Thr | Val | Val | Thr | Gln | Leu | Phe | His | |
| | 225 | | | | | 230 | | | | | 235 | | | | | |
| CAT | AAG | AAT | GGG | GCC | CGA | AAA | AGT | GCC | AAG | AAG | ATC | CTC | ATT | GTC | ATC | 767 |
| His | Lys | Asn | Gly | Ala | Arg | Lys | Ser | Ala | Lys | Lys | Ile | Leu | Ile | Val | Ile | |
| 240 | | | | | 245 | | | | | 250 | | | | | 255 | |
| ACA | GAT | GGG | CAG | AAG | TAC | AAA | GAC | CCC | CTG | GAA | TAC | AGT | GAT | GTC | ATC | 815 |
| Thr | Asp | Gly | Gln | Lys | Tyr | Lys | Asp | Pro | Leu | Glu | Tyr | Ser | Asp | Val | Ile | |
| | | | | 260 | | | | | 265 | | | | | 270 | | |
| CCC | CAG | GCA | GAG | AAG | GCT | GGC | ATC | ATC | CGC | TAC | GCT | ATC | GGG | GTG | GGA | 863 |
| Pro | Gln | Ala | Glu | Lys | Ala | Gly | Ile | Ile | Arg | Tyr | Ala | Ile | Gly | Val | Gly | |
| | | | 275 | | | | | 280 | | | | | 285 | | | |
| CAC | GCT | TTC | CAG | GGA | CCC | ACT | GCC | AGG | CAG | GAG | CTG | AAT | ACC | ATC | AGC | 911 |
| His | Ala | Phe | Gln | Gly | Pro | Thr | Ala | Arg | Gln | Glu | Leu | Asn | Thr | Ile | Ser | |
| | | 290 | | | | | 295 | | | | | 300 | | | | |
| TCA | GCG | CCT | CCG | CAG | GAC | CAC | GTG | TTC | AAG | GTG | GAC | AAC | TTT | GCA | GCC | 959 |
| Ser | Ala | Pro | Pro | Gln | Asp | His | Val | Phe | Lys | Val | Asp | Asn | Phe | Ala | Ala | |
| 305 | | | | | 310 | | | | | 315 | | | | | | |
| CTT | GGC | AGC | ATC | CAG | AAG | CAG | CTG | CAG | GAG | AAG | ATC | TAT | GCA | GTT | GAG | 1007 |
| Leu | Gly | Ser | Ile | Gln | Lys | Gln | Leu | Gln | Glu | Lys | Ile | Tyr | Ala | Val | Glu | |
| 320 | | | | | 325 | | | | | 330 | | | | | 335 | |
| GGA | ACC | CAG | TCC | AGG | GCA | AGC | AGC | TCC | TTC | CAG | CAC | GAG | ATG | TCC | CAA | 1055 |
| Gly | Thr | Gln | Ser | Arg | Ala | Ser | Ser | Ser | Phe | Gln | His | Glu | Met | Ser | Gln | |
| | | | | 340 | | | | | 345 | | | | | 350 | | |
| GAA | GGC | TTC | AGC | ACA | GCC | CTC | ACA | ATG | GAT | GGC | CTC | TTC | CTG | GGG | GCT | 1103 |
| Glu | Gly | Phe | Ser | Thr | Ala | Leu | Thr | Met | Asp | Gly | Leu | Phe | Leu | Gly | Ala | |
| | | | 355 | | | | | 360 | | | | | 365 | | | |
| GTG | GGG | AGC | TTT | AGC | TGG | TCT | GGA | GGT | GCC | TTC | CTG | TAT | CCC | CCA | AAT | 1151 |
| Val | Gly | Ser | Phe | Ser | Trp | Ser | Gly | Gly | Ala | Phe | Leu | Tyr | Pro | Pro | Asn | |
| | | 370 | | | | | 375 | | | | | 380 | | | | |
| ATG | AGC | CCC | ACC | TTC | ATC | AAC | ATG | TCT | CAG | GAG | AAT | GTG | GAC | ATG | AGG | 1199 |
| Met | Ser | Pro | Thr | Phe | Ile | Asn | Met | Ser | Gln | Glu | Asn | Val | Asp | Met | Arg | |
| | 385 | | | | | 390 | | | | | 395 | | | | | |
| GAC | TCT | TAC | CTG | GGT | TAC | TCC | ACC | GAG | CTA | GCC | CTG | TGG | AAG | GGG | GTA | 1247 |
| Asp | Ser | Tyr | Leu | Gly | Tyr | Ser | Thr | Glu | Leu | Ala | Leu | Trp | Lys | Gly | Val | |
| 400 | | | | | 405 | | | | | 410 | | | | | 415 | |
| CAG | AAC | CTG | GTC | CTG | GGG | GCC | CCC | CGC | TAC | CAG | CAT | ACC | GGG | AAG | GCT | 1295 |
| Gln | Asn | Leu | Val | Leu | Gly | Ala | Pro | Arg | Tyr | Gln | His | Thr | Gly | Lys | Ala | |
| | | | | 420 | | | | | 425 | | | | | 430 | | |
| GTC | ATC | TTC | ACC | CAG | GTG | TCC | AGG | CAA | TGG | AGG | AAG | AAG | GCC | GAA | GTC | 1343 |
| Val | Ile | Phe | Thr | Gln | Val | Ser | Arg | Gln | Trp | Arg | Lys | Lys | Ala | Glu | Val | |
| | | | 435 | | | | | 440 | | | | | 445 | | | |
| ACA | GGG | ACG | CAG | ATC | GGC | TCC | TAC | TTC | GGG | GCC | TCC | CTC | TGC | TCC | GTG | 1391 |
| Thr | Gly | Thr | Gln | Ile | Gly | Ser | Tyr | Phe | Gly | Ala | Ser | Leu | Cys | Ser | Val | |
| | | 450 | | | | | 455 | | | | | 460 | | | | |
| GAT | GTG | GAC | AGC | GAT | GGC | AGC | ACC | GAC | CTG | ATC | CTC | ATT | GGG | GCC | CCC | 1439 |
| Asp | Val | Asp | Ser | Asp | Gly | Ser | Thr | Asp | Leu | Ile | Leu | Ile | Gly | Ala | Pro | |
| | 465 | | | | | 470 | | | | | 475 | | | | | |
| CAT | TAC | TAT | GAG | CAG | ACC | CGA | GGG | GGC | CAG | GTG | TCC | GTG | TGT | CCC | TTG | 1487 |
| His | Tyr | Tyr | Glu | Gln | Thr | Arg | Gly | Gly | Gln | Val | Ser | Val | Cys | Pro | Leu | |
| 480 | | | | | 485 | | | | | 490 | | | | | 495 | |
| CCT | AGG | GGG | CAG | AGG | GTG | CAG | TGG | CAG | TGT | GAC | GCT | GTT | CTC | CGT | GGT | 1535 |
| Pro | Arg | Gly | Gln | Arg | Val | Gln | Trp | Gln | Cys | Asp | Ala | Val | Leu | Arg | Gly | |
| | | | | 500 | | | | | 505 | | | | | 510 | | |
| GAG | CAG | GGC | CAC | CCC | TGG | GGC | CGC | TTT | GGG | GCA | GCC | CTG | ACA | GTG | TTG | 1583 |
| Glu | Gln | Gly | His | Pro | Trp | Gly | Arg | Phe | Gly | Ala | Ala | Leu | Thr | Val | Leu | |

|  |  |  |  |  | 515 |  |  |  |  | 520 |  |  |  |  | 525 |  |  |
|---|---|---|---|---|---|---|---|---|---|---|---|---|---|---|---|---|---|
| GGG | GAT | GTG | AAT | GAG | GAC | AAG | CTG | ATA | GAC | GTG | GCC | ATT | GGG | GCC | CCG |  | 1631 |
| Gly | Asp | Val | Asn | Glu | Asp | Lys | Leu | Ile | Asp | Val | Ala | Ile | Gly | Ala | Pro |  |  |
|  |  | 530 |  |  |  |  | 535 |  |  |  |  | 540 |  |  |  |  |  |
| GGA | GAG | CAG | GAG | AAC | CGG | GGT | GCT | GTC | TAC | CTG | TTT | CAC | GGA | GCC | TCA |  | 1679 |
| Gly | Glu | Gln | Glu | Asn | Arg | Gly | Ala | Val | Tyr | Leu | Phe | His | Gly | Ala | Ser |  |  |
|  | 545 |  |  |  |  | 550 |  |  |  |  | 555 |  |  |  |  |  |  |
| GAA | TCC | GGC | ATC | AGC | CCC | TCC | CAC | AGC | CAG | CGG | ATT | GCC | AGC | TCC | CAG |  | 1727 |
| Glu | Ser | Gly | Ile | Ser | Pro | Ser | His | Ser | Gln | Arg | Ile | Ala | Ser | Ser | Gln |  |  |
| 560 |  |  |  |  | 565 |  |  |  |  | 570 |  |  |  |  | 575 |  |  |
| CTC | TCC | CCC | AGG | CTG | CAG | TAT | TTT | GGG | CAG | GCG | CTG | AGT | GGG | GGT | CAG |  | 1775 |
| Leu | Ser | Pro | Arg | Leu | Gln | Tyr | Phe | Gly | Gln | Ala | Leu | Ser | Gly | Gly | Gln |  |  |
|  |  |  |  | 580 |  |  |  |  | 585 |  |  |  |  | 590 |  |  |  |
| GAC | CTC | ACC | CAG | GAT | GGA | CTG | ATG | GAC | CTG | GCC | GTG | GGG | GCC | CGG | GGC |  | 1823 |
| Asp | Leu | Thr | Gln | Asp | Gly | Leu | Met | Asp | Leu | Ala | Val | Gly | Ala | Arg | Gly |  |  |
|  |  |  | 595 |  |  |  |  | 600 |  |  |  |  | 605 |  |  |  |  |
| CAG | GTG | CTC | CTG | CTC | AGG | AGT | CTG | CCG | GTG | CTG | AAA | GTG | GGG | GTG | GCC |  | 1871 |
| Gln | Val | Leu | Leu | Leu | Arg | Ser | Leu | Pro | Val | Leu | Lys | Val | Gly | Val | Ala |  |  |
|  |  | 610 |  |  |  |  | 615 |  |  |  |  | 620 |  |  |  |  |  |
| ATG | AGA | TTC | AGC | CCT | GTG | GAG | GTG | GCC | AAG | GCT | GTG | TAC | CGG | TGC | TGG |  | 1919 |
| Met | Arg | Phe | Ser | Pro | Val | Glu | Val | Ala | Lys | Ala | Val | Tyr | Arg | Cys | Trp |  |  |
|  | 625 |  |  |  |  | 630 |  |  |  |  | 635 |  |  |  |  |  |  |
| GAA | GAG | AAG | CCC | AGT | GCC | CTG | GAA | GCT | GGG | GAC | GCC | ACC | GTC | TGT | CTC |  | 1967 |
| Glu | Glu | Lys | Pro | Ser | Ala | Leu | Glu | Ala | Gly | Asp | Ala | Thr | Val | Cys | Leu |  |  |
| 640 |  |  |  |  | 645 |  |  |  |  | 650 |  |  |  |  | 655 |  |  |
| ACC | ATC | CAG | AAA | AGC | TCA | CTG | GAC | CAG | CTA | GGT | GAC | ATC | CAA | AGC | TCT |  | 2015 |
| Thr | Ile | Gln | Lys | Ser | Ser | Leu | Asp | Gln | Leu | Gly | Asp | Ile | Gln | Ser | Ser |  |  |
|  |  |  |  | 660 |  |  |  |  | 665 |  |  |  |  | 670 |  |  |  |
| GTC | AGG | TTT | GAT | CTG | GCA | CTG | GAC | CCA | GGT | CGT | CTG | ACT | TCT | CGT | GCC |  | 2063 |
| Val | Arg | Phe | Asp | Leu | Ala | Leu | Asp | Pro | Gly | Arg | Leu | Thr | Ser | Arg | Ala |  |  |
|  |  |  | 675 |  |  |  |  | 680 |  |  |  |  | 685 |  |  |  |  |
| ATT | TTC | AAT | GAA | ACC | AAG | AAC | CCC | ACT | TTG | ACT | CGA | AGA | AAA | ACC | CTG |  | 2111 |
| Ile | Phe | Asn | Glu | Thr | Lys | Asn | Pro | Thr | Leu | Thr | Arg | Arg | Lys | Thr | Leu |  |  |
|  |  | 690 |  |  |  |  | 695 |  |  |  |  | 700 |  |  |  |  |  |
| GGA | CTG | GGG | ATT | CAC | TGT | GAA | ACC | CTG | AAG | CTG | CTT | TTG | CCA | GAT | TGT |  | 2159 |
| Gly | Leu | Gly | Ile | His | Cys | Glu | Thr | Leu | Lys | Leu | Leu | Leu | Pro | Asp | Cys |  |  |
|  | 705 |  |  |  |  | 710 |  |  |  |  | 715 |  |  |  |  |  |  |
| GTG | GAG | GAT | GTG | GTG | AGC | CCC | ATC | ATT | CTG | CAC | CTC | AAC | TTC | TCA | CTG |  | 2207 |
| Val | Glu | Asp | Val | Val | Ser | Pro | Ile | Ile | Leu | His | Leu | Asn | Phe | Ser | Leu |  |  |
| 720 |  |  |  |  | 725 |  |  |  |  | 730 |  |  |  |  | 735 |  |  |
| GTG | AGA | GAG | CCC | ATC | CCC | TCC | CCC | CAG | AAC | CTG | CGT | CCT | GTG | CTG | GCC |  | 2255 |
| Val | Arg | Glu | Pro | Ile | Pro | Ser | Pro | Gln | Asn | Leu | Arg | Pro | Val | Leu | Ala |  |  |
|  |  |  |  | 740 |  |  |  |  | 745 |  |  |  |  | 750 |  |  |  |
| GTG | GGC | TCA | CAA | GAC | CTC | TTC | ACT | GCT | TCT | CTC | CCC | TTC | GAG | AAG | AAC |  | 2303 |
| Val | Gly | Ser | Gln | Asp | Leu | Phe | Thr | Ala | Ser | Leu | Pro | Phe | Glu | Lys | Asn |  |  |
|  |  |  | 755 |  |  |  |  | 760 |  |  |  |  | 765 |  |  |  |  |
| TGT | GGG | CAA | GAT | GGC | CTC | TGT | GAA | GGG | GAC | CTG | GGT | GTC | ACC | CTC | AGC |  | 2351 |
| Cys | Gly | Gln | Asp | Gly | Leu | Cys | Glu | Gly | Asp | Leu | Gly | Val | Thr | Leu | Ser |  |  |
|  |  | 770 |  |  |  |  | 775 |  |  |  |  | 780 |  |  |  |  |  |
| TTC | TCA | GGC | CTG | CAG | ACC | CTG | ACC | GTG | GGG | AGC | TCC | CTG | GAG | CTC | AAC |  | 2399 |
| Phe | Ser | Gly | Leu | Gln | Thr | Leu | Thr | Val | Gly | Ser | Ser | Leu | Glu | Leu | Asn |  |  |
|  | 785 |  |  |  |  | 790 |  |  |  |  | 795 |  |  |  |  |  |  |
| GTG | ATT | GTG | ACT | GTG | TGG | AAC | GCA | GGT | GAG | GAT | TCC | TAC | GGA | ACC | GTG |  | 2447 |
| Val | Ile | Val | Thr | Val | Trp | Asn | Ala | Gly | Glu | Asp | Ser | Tyr | Gly | Thr | Val |  |  |
| 800 |  |  |  |  | 805 |  |  |  |  | 810 |  |  |  |  | 815 |  |  |
| GTC | AGC | CTC | TAC | TAT | CCA | GCA | GGG | CTG | TCG | CAC | CGA | CGG | GTG | TCA | GGA |  | 2495 |
| Val | Ser | Leu | Tyr | Tyr | Pro | Ala | Gly | Leu | Ser | His | Arg | Arg | Val | Ser | Gly |  |  |
|  |  |  |  | 820 |  |  |  |  | 825 |  |  |  |  | 830 |  |  |  |
| GCC | CAG | AAG | CAG | CCC | CAT | CAG | AGT | GCC | CTG | CGC | CTG | GCA | TGT | GAG | ACA |  | 2543 |

-continued

| | | | | | | | | | | | | | | | | |
|---|---|---|---|---|---|---|---|---|---|---|---|---|---|---|---|---|
| Ala | Gln | Lys | Gln | Pro | His | Gln | Ser | Ala | Leu | Arg | Leu | Ala | Cys | Glu | Thr | |
| | | | 835 | | | | 840 | | | | | 845 | | | | |

| GTG | CCC | ACT | GAG | GAT | GAG | GGC | CTA | AGA | AGC | AGC | CGC | TGC | AGT | GTC | AAC | 2591 |
|---|---|---|---|---|---|---|---|---|---|---|---|---|---|---|---|---|
| Val | Pro | Thr | Glu | Asp | Glu | Gly | Leu | Arg | Ser | Ser | Arg | Cys | Ser | Val | Asn | |
| | | 850 | | | | | 855 | | | | | 860 | | | | |

| CAC | CCC | ATC | TTC | CAT | GAG | GGC | TCT | AAC | GGC | ACC | TTC | ATA | GTC | ACA | TTC | 2639 |
|---|---|---|---|---|---|---|---|---|---|---|---|---|---|---|---|---|
| His | Pro | Ile | Phe | His | Glu | Gly | Ser | Asn | Gly | Thr | Phe | Ile | Val | Thr | Phe | |
| | 865 | | | | | 870 | | | | | 875 | | | | | |

| GAT | GTC | TCC | TAC | AAG | GCC | ACC | CTG | GGA | GAC | AGG | ATG | CTT | ATG | AGG | GCC | 2687 |
|---|---|---|---|---|---|---|---|---|---|---|---|---|---|---|---|---|
| Asp | Val | Ser | Tyr | Lys | Ala | Thr | Leu | Gly | Asp | Arg | Met | Leu | Met | Arg | Ala | |
| 880 | | | | | 885 | | | | | 890 | | | | | 895 | |

| AGT | GCA | AGC | AGT | GAG | AAC | AAT | AAG | GCT | TCA | AGC | AGC | AAG | GCC | ACC | TTC | 2735 |
|---|---|---|---|---|---|---|---|---|---|---|---|---|---|---|---|---|
| Ser | Ala | Ser | Ser | Glu | Asn | Asn | Lys | Ala | Ser | Ser | Ser | Lys | Ala | Thr | Phe | |
| | | | | 900 | | | | 905 | | | | | 910 | | | |

| CAG | CTG | GAG | CTC | CCG | GTG | AAG | TAT | GCA | GTC | TAC | ACC | ATG | ATC | AGC | AGG | 2783 |
|---|---|---|---|---|---|---|---|---|---|---|---|---|---|---|---|---|
| Gln | Leu | Glu | Leu | Pro | Val | Lys | Tyr | Ala | Val | Tyr | Thr | Met | Ile | Ser | Arg | |
| | | | 915 | | | | | 920 | | | | | 925 | | | |

| CAG | GAA | GAA | TCC | ACC | AAG | TAC | TTC | AAC | TTT | GCA | ACC | TCC | GAT | GAG | AAG | 2831 |
|---|---|---|---|---|---|---|---|---|---|---|---|---|---|---|---|---|
| Gln | Glu | Glu | Ser | Thr | Lys | Tyr | Phe | Asn | Phe | Ala | Thr | Ser | Asp | Glu | Lys | |
| | | 930 | | | | | 935 | | | | | 940 | | | | |

| AAA | ATG | AAA | GAG | GCT | GAG | CAT | CGA | TAC | CGT | GTG | AAT | AAC | CTC | AGC | CAG | 2879 |
|---|---|---|---|---|---|---|---|---|---|---|---|---|---|---|---|---|
| Lys | Met | Lys | Glu | Ala | Glu | His | Arg | Tyr | Arg | Val | Asn | Asn | Leu | Ser | Gln | |
| | 945 | | | | | 950 | | | | | 955 | | | | | |

| CGA | GAT | CTG | GCC | ATC | AGC | ATT | AAC | TTC | TGG | GTT | CCT | GTC | CTG | CTG | AAC | 2927 |
|---|---|---|---|---|---|---|---|---|---|---|---|---|---|---|---|---|
| Arg | Asp | Leu | Ala | Ile | Ser | Ile | Asn | Phe | Trp | Val | Pro | Val | Leu | Leu | Asn | |
| 960 | | | | | 965 | | | | | 970 | | | | | 975 | |

| GGG | GTG | GCT | GTG | TGG | GAT | GTG | GTC | ATG | GAG | GCC | CCA | TCT | CAG | AGT | CTC | 2975 |
|---|---|---|---|---|---|---|---|---|---|---|---|---|---|---|---|---|
| Gly | Val | Ala | Val | Trp | Asp | Val | Val | Met | Glu | Ala | Pro | Ser | Gln | Ser | Leu | |
| | | | | 980 | | | | 985 | | | | | 990 | | | |

| CCC | TGT | GTT | TCA | GAG | AGA | AAA | CCT | CCC | CAG | CAT | TCT | GAC | TTC | CTG | ACC | 3023 |
|---|---|---|---|---|---|---|---|---|---|---|---|---|---|---|---|---|
| Pro | Cys | Val | Ser | Glu | Arg | Lys | Pro | Pro | Gln | His | Ser | Asp | Phe | Leu | Thr | |
| | | | 995 | | | | | 1000 | | | | | 1005 | | | |

| CAG | ATT | TCA | AGA | AGT | CCC | ATG | CTG | GAC | TGC | TCC | ATT | GCT | GAC | TGC | CTG | 3071 |
|---|---|---|---|---|---|---|---|---|---|---|---|---|---|---|---|---|
| Gln | Ile | Ser | Arg | Ser | Pro | Met | Leu | Asp | Cys | Ser | Ile | Ala | Asp | Cys | Leu | |
| | | | 1010 | | | | 1015 | | | | | 1020 | | | | |

| CAG | TTC | CGC | TGT | GAC | GTC | CCC | TCC | TTC | AGC | GTC | CAG | GAG | GAG | CTG | GAT | 3119 |
|---|---|---|---|---|---|---|---|---|---|---|---|---|---|---|---|---|
| Gln | Phe | Arg | Cys | Asp | Val | Pro | Ser | Phe | Ser | Val | Gln | Glu | Glu | Leu | Asp | |
| | | | 1025 | | | | 1030 | | | | | 1035 | | | | |

| TTC | ACC | CTG | AAG | GGC | AAT | CTC | AGT | TTC | GGC | TGG | GTC | CGC | GAG | ACA | TTG | 3167 |
|---|---|---|---|---|---|---|---|---|---|---|---|---|---|---|---|---|
| Phe | Thr | Leu | Lys | Gly | Asn | Leu | Ser | Phe | Gly | Trp | Val | Arg | Glu | Thr | Leu | |
| 1040 | | | | | 1045 | | | | | 1050 | | | | | 1055 | |

| CAG | AAG | AAG | GTG | TTG | GTC | GTG | AGT | GTG | GCT | GAA | ATT | ACG | TTC | GAC | ACA | 3215 |
|---|---|---|---|---|---|---|---|---|---|---|---|---|---|---|---|---|
| Gln | Lys | Lys | Val | Leu | Val | Val | Ser | Val | Ala | Glu | Ile | Thr | Phe | Asp | Thr | |
| | | | 1060 | | | | | 1065 | | | | | 1070 | | | |

| TCC | GTG | TAC | TCC | CAG | CTT | CCA | GGA | CAG | GAG | GCA | TTT | ATG | AGA | GCT | CAG | 3263 |
|---|---|---|---|---|---|---|---|---|---|---|---|---|---|---|---|---|
| Ser | Val | Tyr | Ser | Gln | Leu | Pro | Gly | Gln | Glu | Ala | Phe | Met | Arg | Ala | Gln | |
| | | | 1075 | | | | | 1080 | | | | | 1085 | | | |

| ATG | GAG | ATG | GTG | CTA | GAA | GAA | GAC | GAG | GTC | TAC | AAT | GCC | ATT | CCC | ATC | 3311 |
|---|---|---|---|---|---|---|---|---|---|---|---|---|---|---|---|---|
| Met | Glu | Met | Val | Leu | Glu | Glu | Asp | Glu | Val | Tyr | Asn | Ala | Ile | Pro | Ile | |
| | | | 1090 | | | | | 1095 | | | | | 1100 | | | |

| ATC | ATG | GGC | AGC | TCT | GTG | GGG | GCT | CTG | CTA | CTG | CTG | GCG | CTC | ATC | ACA | 3359 |
|---|---|---|---|---|---|---|---|---|---|---|---|---|---|---|---|---|
| Ile | Met | Gly | Ser | Ser | Val | Gly | Ala | Leu | Leu | Leu | Leu | Ala | Leu | Ile | Thr | |
| | | | 1105 | | | | | 1110 | | | | | 1115 | | | |

| GCC | ACA | CTG | TAC | AAG | CTT | GGC | TTC | TTC | AAA | CGC | CAC | TAC | AAG | GAA | ATG | 3407 |
|---|---|---|---|---|---|---|---|---|---|---|---|---|---|---|---|---|
| Ala | Thr | Leu | Tyr | Lys | Leu | Gly | Phe | Phe | Lys | Arg | His | Tyr | Lys | Glu | Met | |
| 1120 | | | | | 1125 | | | | | 1130 | | | | | 1135 | |

| CTG | GAG | GAC | AAG | CCT | GAA | GAC | ACT | GCC | ACA | TTC | AGT | GGG | GAC | GAT | TTC | 3455 |
|---|---|---|---|---|---|---|---|---|---|---|---|---|---|---|---|---|
| Leu | Glu | Asp | Lys | Pro | Glu | Asp | Thr | Ala | Thr | Phe | Ser | Gly | Asp | Asp | Phe | |
| | | | 1140 | | | | | 1145 | | | | | 1150 | | | |

```
AGC TGT GTG GCC CCA AAT GTG CCT TTG TCC TAATAATCCA CTTTCCTGTT      3505
Ser Cys Val Ala Pro Asn Val Pro Leu Ser
            1155              1160

TATCTCTACC ACTGTGGGCT GGACTTGCTT GCAACCATAA ATCAACTTAC ATGGAAACAA   3565

CTTCTGCATA GATCTGCACT GGCCTAAGCA ACCTACCAGG TGCTAAGCAC CTTCTCGGAG   3625

AGATAGAGAT TGTAATGTTT TTACATATCT GTCCATCTTT TTCAGCAATG ACCCACTTTT   3685

TACAGAAGCA GGCATGGTGC CAGCATAAAT TTTCATATGC T                      3726
```

( 2 ) INFORMATION FOR SEQ ID NO:2:

( i ) SEQUENCE CHARACTERISTICS:
        ( A ) LENGTH: 1161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Thr Phe Gly Thr Val Leu Leu Leu Ser Val Leu Ala Ser Tyr His Gly
 1           5                   10                  15
Phe Asn Leu Asp Val Glu Glu Pro Thr Ile Phe Gln Glu Asp Ala Gly
            20                  25                  30
Gly Phe Gly Gln Ser Val Val Gln Phe Gly Gly Ser Arg Leu Val Val
        35                  40                  45
Gly Ala Pro Leu Glu Val Val Ala Ala Asn Gln Thr Gly Arg Leu Tyr
    50                  55                  60
Asp Cys Ala Ala Ala Thr Gly Met Cys Gln Pro Ile Pro Leu His Ile
65                  70                  75                  80
Arg Pro Glu Ala Val Asn Met Ser Leu Gly Leu Thr Leu Ala Ala Ser
                85                  90                  95
Thr Asn Gly Ser Arg Leu Leu Ala Cys Gly Pro Thr Leu His Arg Val
            100                 105                 110
Cys Gly Glu Asn Ser Tyr Ser Lys Gly Ser Cys Leu Leu Leu Gly Ser
        115                 120                 125
Arg Trp Glu Ile Ile Gln Thr Val Pro Asp Ala Thr Pro Glu Cys Pro
    130                 135                 140
His Gln Glu Met Asp Ile Val Phe Leu Ile Asp Gly Ser Gly Ser Ile
145                 150                 155                 160
Asp Gln Asn Asp Phe Asn Gln Met Lys Gly Phe Val Gln Ala Val Met
                165                 170                 175
Gly Gln Phe Glu Gly Thr Asp Thr Leu Phe Ala Leu Met Gln Tyr Ser
            180                 185                 190
Asn Leu Leu Lys Ile His Phe Thr Phe Thr Gln Phe Arg Thr Ser Pro
        195                 200                 205
Ser Gln Gln Ser Leu Val Asp Pro Ile Val Gln Leu Lys Gly Leu Thr
    210                 215                 220
Phe Thr Ala Thr Gly Ile Leu Thr Val Val Thr Gln Leu Phe His His
225                 230                 235                 240
Lys Asn Gly Ala Arg Lys Ser Ala Lys Lys Ile Leu Ile Val Ile Thr
                245                 250                 255
Asp Gly Gln Lys Tyr Lys Asp Pro Leu Glu Tyr Ser Asp Val Ile Pro
            260                 265                 270
Gln Ala Glu Lys Ala Gly Ile Ile Arg Tyr Ala Ile Gly Val Gly His
        275                 280                 285
Ala Phe Gln Gly Pro Thr Ala Arg Gln Glu Leu Asn Thr Ile Ser Ser
```

-continued

|     | 290 |     |     |     | 295 |     |     |     | 300 |     |     |     |     |     |
|-----|-----|-----|-----|-----|-----|-----|-----|-----|-----|-----|-----|-----|-----|-----|
| Ala 305 | Pro | Pro | Gln | Asp 310 | His | Val | Phe | Lys | Val 315 | Asp | Asn | Phe | Ala | Ala 320 Leu |
| Gly | Ser | Ile | Gln | Lys 325 | Gln | Leu | Gln | Glu | Lys 330 | Ile | Tyr | Ala | Val | Glu 335 Gly |
| Thr | Gln | Ser | Arg 340 | Ala | Ser | Ser | Ser | Phe 345 | Gln | His | Glu | Met | Ser 350 | Gln Glu |
| Gly | Phe | Ser 355 | Thr | Ala | Leu | Thr | Met 360 | Asp | Gly | Leu | Phe | Leu 365 | Gly | Ala Val |
| Gly | Ser 370 | Phe | Ser | Trp | Ser | Gly 375 | Gly | Ala | Phe | Leu | Tyr 380 | Pro | Pro | Asn Met |
| Ser 385 | Pro | Thr | Phe | Ile | Asn 390 | Met | Ser | Gln | Glu | Asn 395 | Val | Asp | Met | Arg | Asp 400 |
| Ser | Tyr | Leu | Gly | Tyr 405 | Ser | Thr | Glu | Leu | Ala 410 | Leu | Trp | Lys | Gly | Val 415 | Gln |
| Asn | Leu | Val | Leu 420 | Gly | Ala | Pro | Arg | Tyr 425 | Gln | His | Thr | Gly | Lys 430 | Ala | Val |
| Ile | Phe | Thr 435 | Gln | Val | Ser | Arg | Gln 440 | Trp | Arg | Lys | Lys | Ala 445 | Glu | Val | Thr |
| Gly | Thr 450 | Gln | Ile | Gly | Ser | Tyr 455 | Phe | Gly | Ala | Ser | Leu 460 | Cys | Ser | Val | Asp |
| Val 465 | Asp | Ser | Asp | Gly | Ser 470 | Thr | Asp | Leu | Ile | Leu 475 | Ile | Gly | Ala | Pro | His 480 |
| Tyr | Tyr | Glu | Gln | Thr 485 | Arg | Gly | Gly | Gln | Val 490 | Ser | Val | Cys | Pro | Leu 495 | Pro |
| Arg | Gly | Gln | Arg 500 | Val | Gln | Trp | Gln | Cys 505 | Asp | Ala | Val | Leu | Arg 510 | Gly | Glu |
| Gln | Gly | His | Pro 515 | Trp | Gly | Arg | Phe 520 | Gly | Ala | Ala | Leu | Thr 525 | Val | Leu | Gly |
| Asp | Val | Asn 530 | Glu | Asp | Lys | Leu 535 | Ile | Asp | Val | Ala | Ile 540 | Gly | Ala | Pro | Gly |
| Glu 545 | Gln | Glu | Asn | Arg | Gly 550 | Ala | Val | Tyr | Leu | Phe 555 | His | Gly | Ala | Ser | Glu 560 |
| Ser | Gly | Ile | Ser | Pro 565 | Ser | His | Ser | Gln | Arg 570 | Ile | Ala | Ser | Ser | Gln 575 | Leu |
| Ser | Pro | Arg | Leu 580 | Gln | Tyr | Phe | Gly | Gln 585 | Ala | Leu | Ser | Gly | Gly 590 | Gln | Asp |
| Leu | Thr | Gln 595 | Asp | Gly | Leu | Met | Asp 600 | Leu | Ala | Val | Gly | Ala 605 | Arg | Gly | Gln |
| Val | Leu 610 | Leu | Leu | Arg | Ser | Leu 615 | Pro | Val | Leu | Lys | Val 620 | Gly | Val | Ala | Met |
| Arg 625 | Phe | Ser | Pro | Val | Glu 630 | Val | Ala | Lys | Ala | Val 635 | Tyr | Arg | Cys | Trp | Glu 640 |
| Glu | Lys | Pro | Ser | Ala 645 | Leu | Glu | Ala | Gly | Asp 650 | Ala | Thr | Val | Cys | Leu 655 | Thr |
| Ile | Gln | Lys | Ser 660 | Ser | Leu | Asp | Gln | Leu 665 | Gly | Asp | Ile | Gln | Ser 670 | Ser | Val |
| Arg | Phe | Asp 675 | Leu | Ala | Leu | Asp | Pro 680 | Gly | Arg | Leu | Thr | Ser 685 | Arg | Ala | Ile |
| Phe | Asn | Glu 690 | Thr | Lys | Asn | Pro | Thr 695 | Leu | Thr | Arg | Arg | Lys 700 | Thr | Leu | Gly |
| Leu 705 | Gly | Ile | His | Cys | Glu 710 | Thr | Leu | Lys | Leu | Leu 715 | Leu | Pro | Asp | Cys | Val 720 |

```
Glu  Asp  Val  Val  Ser  Pro  Ile  Ile  Leu  His  Leu  Asn  Phe  Ser  Leu  Val
               725                      730                      735

Arg  Glu  Pro  Ile  Pro  Ser  Pro  Gln  Asn  Leu  Arg  Pro  Val  Leu  Ala  Val
               740                      745                      750

Gly  Ser  Gln  Asp  Leu  Phe  Thr  Ala  Ser  Leu  Pro  Phe  Glu  Lys  Asn  Cys
               755                      760                      765

Gly  Gln  Asp  Gly  Leu  Cys  Glu  Gly  Asp  Leu  Gly  Val  Thr  Leu  Ser  Phe
               770                      775                      780

Ser  Gly  Leu  Gln  Thr  Leu  Thr  Val  Gly  Ser  Ser  Leu  Glu  Leu  Asn  Val
785                      790                      795                      800

Ile  Val  Thr  Val  Trp  Asn  Ala  Gly  Glu  Asp  Ser  Tyr  Gly  Thr  Val  Val
               805                      810                      815

Ser  Leu  Tyr  Tyr  Pro  Ala  Gly  Leu  Ser  His  Arg  Arg  Val  Ser  Gly  Ala
               820                      825                      830

Gln  Lys  Gln  Pro  His  Gln  Ser  Ala  Leu  Arg  Leu  Ala  Cys  Glu  Thr  Val
               835                      840                      845

Pro  Thr  Glu  Asp  Glu  Gly  Leu  Arg  Ser  Ser  Arg  Cys  Ser  Val  Asn  His
     850                      855                      860

Pro  Ile  Phe  His  Glu  Gly  Ser  Asn  Gly  Thr  Phe  Ile  Val  Thr  Phe  Asp
865                      870                      875                      880

Val  Ser  Tyr  Lys  Ala  Thr  Leu  Gly  Asp  Arg  Met  Leu  Met  Arg  Ala  Ser
               885                      890                      895

Ala  Ser  Ser  Glu  Asn  Asn  Lys  Ala  Ser  Ser  Lys  Ala  Thr  Phe  Gln
               900                      905                      910

Leu  Glu  Leu  Pro  Val  Lys  Tyr  Ala  Val  Tyr  Thr  Met  Ile  Ser  Arg  Gln
          915                      920                      925

Glu  Glu  Ser  Thr  Lys  Tyr  Phe  Asn  Phe  Ala  Thr  Ser  Asp  Glu  Lys  Lys
     930                      935                      940

Met  Lys  Glu  Ala  Glu  His  Arg  Tyr  Arg  Val  Asn  Asn  Leu  Ser  Gln  Arg
945                      950                      955                      960

Asp  Leu  Ala  Ile  Ser  Ile  Asn  Phe  Trp  Val  Pro  Val  Leu  Leu  Asn  Gly
               965                      970                      975

Val  Ala  Val  Trp  Asp  Val  Val  Met  Glu  Ala  Pro  Ser  Gln  Ser  Leu  Pro
               980                      985                      990

Cys  Val  Ser  Glu  Arg  Lys  Pro  Pro  Gln  His  Ser  Asp  Phe  Leu  Thr  Gln
          995                      1000                     1005

Ile  Ser  Arg  Ser  Pro  Met  Leu  Asp  Cys  Ser  Ile  Ala  Asp  Cys  Leu  Gln
     1010                     1015                     1020

Phe  Arg  Cys  Asp  Val  Pro  Ser  Phe  Ser  Val  Gln  Glu  Glu  Leu  Asp  Phe
1025                     1030                     1035                     1040

Thr  Leu  Lys  Gly  Asn  Leu  Ser  Phe  Gly  Trp  Val  Arg  Glu  Thr  Leu  Gln
               1045                     1050                     1055

Lys  Lys  Val  Leu  Val  Val  Ser  Val  Ala  Glu  Ile  Thr  Phe  Asp  Thr  Ser
               1060                     1065                     1070

Val  Tyr  Ser  Gln  Leu  Pro  Gly  Gln  Glu  Ala  Phe  Met  Arg  Ala  Gln  Met
          1075                     1080                     1085

Glu  Met  Val  Leu  Glu  Glu  Asp  Glu  Val  Tyr  Asn  Ala  Ile  Pro  Ile  Ile
     1090                     1095                     1100

Met  Gly  Ser  Ser  Val  Gly  Ala  Leu  Leu  Leu  Leu  Ala  Leu  Ile  Thr  Ala
1105                     1110                     1115                     1120

Thr  Leu  Tyr  Lys  Leu  Gly  Phe  Phe  Lys  Arg  His  Tyr  Lys  Glu  Met  Leu
               1125                     1130                     1135
```

```
Glu Asp Lys Pro Glu Asp Thr Ala Thr Phe Ser Gly Asp Asp Phe Ser
         1140               1145                1150

Cys Val Ala Pro Asn Val Pro Lys Ser
         1155            1160
```

( 2 ) INFORMATION FOR SEQ ID NO:3:

( i ) SEQUENCE CHARACTERISTICS:
        ( A ) LENGTH: 1153 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Met Ala Leu Arg Val Leu Leu Leu Thr Ala Leu Thr Leu Cys His Gly
 1               5                   10                  15

Phe Asn Leu Asp Thr Glu Asn Ala Met Thr Phe Gln Glu Asn Ala Arg
             20                  25                  30

Gly Phe Gly Gln Ser Val Val Gln Leu Gln Gly Ser Arg Val Val Val
         35                  40                  45

Gly Ala Pro Gln Glu Ile Val Ala Ala Asn Gln Arg Gly Ser Leu Tyr
 50                  55                  60

Gln Cys Asp Tyr Ser Thr Gly Ser Cys Glu Pro Ile Arg Leu Gln Val
 65                  70                  75                  80

Pro Val Glu Ala Val Asn Met Ser Leu Gly Leu Ser Leu Ala Ala Thr
                 85                  90                  95

Thr Ser Pro Pro Gln Leu Leu Ala Cys Gly Pro Thr Val His Gln Thr
             100                 105                 110

Cys Ser Glu Asn Thr Tyr Val Lys Gly Leu Cys Phe Leu Phe Gly Ser
             115                 120                 125

Asn Leu Arg Gln Gln Pro Gln Lys Phe Pro Glu Ala Leu Arg Gly Cys
         130                 135                 140

Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
             165                 170                 175

Met Glu Gln Leu Lys Lys Ser Lys Thr Leu Phe Ser Leu Met Gln Tyr
             180                 185                 190

Ser Glu Glu Phe Arg Ile His Phe Thr Phe Lys Glu Phe Gln Asn Asn
         195                 200                 205

Pro Asn Pro Arg Ser Leu Val Lys Pro Ile Thr Gln Leu Leu Gly Arg
210                 215                 220

Thr His Thr Ala Thr Gly Ile Arg Lys Val Val Arg Glu Leu Phe Asn
225                 230                 235                 240

Ile Thr Asn Gly Ala Arg Lys Asn Ala Phe Lys Ile Leu Val Val Ile
             245                 250                 255

Thr Asp Gly Glu Lys Phe Gly Asp Pro Leu Gly Tyr Glu Asp Val Ile
             260                 265                 270

Pro Glu Ala Asp Arg Glu Gly Val Ile Arg Tyr Val Ile Gly Val Gly
         275                 280                 285

Asp Ala Phe Arg Ser Glu Lys Ser Arg Gln Glu Leu Asn Thr Ile Ala
         290                 295                 300

Ser Lys Pro Pro Arg Asp His Val Phe Gln Val Asn Asn Phe Glu Ala
305                 310                 315                 320
```

```
Leu Lys Thr Ile Gln Asn Gln Leu Arg Glu Lys Ile Phe Ala Ile Glu
            325                 330                 335

Gly Thr Gln Thr Gly Ser Ser Ser Phe Glu His Glu Met Ser Gln
            340             345                 350

Glu Gly Phe Ser Ala Ala Ile Thr Ser Asn Gly Pro Leu Leu Ser Thr
            355             360             365

Val Gly Ser Tyr Asp Trp Ala Gly Gly Val Phe Leu Tyr Thr Ser Lys
    370             375                 380

Glu Lys Ser Thr Phe Ile Asn Met Thr Arg Val Asp Ser Asp Met Asn
385             390             395                         400

Asp Ala Tyr Leu Gly Tyr Ala Ala Ala Ile Ile Leu Arg Asn Arg Val
                405             410                 415

Gln Ser Leu Val Leu Gly Ala Pro Arg Tyr Gln His Ile Gly Leu Val
            420             425                 430

Ala Met Phe Arg Gln Asn Thr Gly Met Trp Glu Ser Asn Ala Asn Val
        435             440                 445

Lys Gly Thr Gln Ile Gly Ala Tyr Phe Gly Ala Ser Leu Cys Ser Val
    450             455             460

Asp Val Asp Ser Asn Gly Ser Thr Asp Leu Val Leu Ile Gly Ala Pro
465             470             475                         480

His Tyr Tyr Glu Gln Thr Arg Gly Gly Gln Val Ser Val Cys Pro Leu
            485             490                 495

Pro Arg Gly Gln Arg Ala Arg Trp Gln Cys Asp Ala Val Leu Tyr Gly
        500             505                 510

Glu Gln Gly Gln Pro Trp Gly Arg Phe Gly Ala Ala Leu Thr Val Leu
    515             520                 525

Gly Asp Val Asn Gly Asp Lys Leu Thr Asp Val Ala Ile Gly Ala Pro
    530             535             540

Gly Glu Glu Asp Asn Arg Gly Ala Val Tyr Leu Phe His Gly Thr Ser
545             550             555                         560

Gly Ser Gly Ile Ser Pro Ser His Ser Gln Arg Ile Ala Gly Ser Lys
            565             570                 575

Leu Ser Pro Arg Leu Gln Tyr Phe Gly Gln Ser Leu Ser Gly Gly Gln
        580             585             590

Asp Leu Thr Met Asp Gly Leu Val Asp Leu Thr Val Gly Ala Gln Gly
        595             600             605

His Val Leu Leu Leu Arg Ser Gln Pro Val Leu Arg Val Lys Ala Ile
    610             615             620

Met Glu Phe Asn Pro Arg Glu Val Ala Arg Asn Val Phe Glu Cys Asn
625             630             635                         640

Asp Gln Val Val Lys Gly Lys Glu Ala Gly Glu Val Arg Val Cys Leu
            645             650                 655

His Val Gln Lys Ser Thr Arg Asp Arg Leu Arg Glu Gly Gln Ile Gln
        660             665             670

Ser Val Val Thr Tyr Asp Leu Ala Leu Asp Ser Gly Arg Pro His Ser
        675             680             685

Arg Ala Val Phe Asn Glu Thr Lys Asn Ser Thr Arg Arg Gln Thr Gln
    690             695             700

Val Leu Gly Leu Thr Gln Thr Cys Glu Thr Leu Lys Leu Gln Leu Pro
705             710             715                         720

Asn Cys Ile Glu Asp Pro Val Ser Pro Ile Val Leu Arg Leu Asn Phe
            725             730                 735

Ser Leu Val Gly Thr Pro Leu Ser Ala Phe Gly Asn Leu Arg Pro Val
```

-continued

|   |   |   |   | 740 |   |   |   |   |   | 745 |   |   |   |   | 750 |   |   |
|---|---|---|---|---|---|---|---|---|---|---|---|---|---|---|---|---|---|

Leu Ala Glu Asp Ala Gln Arg Leu Phe Thr Ala Leu Phe Pro Phe Glu
           755                     760                 765

Lys Asn Cys Gly Asn Asp Asn Ile Cys Gln Asp Asp Leu Ser Ile Thr
        770             775                 780

Phe Ser Phe Met Ser Leu Asp Cys Leu Val Val Gly Gly Pro Arg Glu
785                 790                 795                 800

Phe Asn Val Thr Val Thr Val Arg Asn Asp Gly Glu Asp Ser Tyr Arg
            805             810                 815

Thr Gln Val Thr Phe Phe Phe Pro Leu Asp Leu Ser Tyr Arg Lys Val
            820             825                 830

Ser Thr Leu Gln Asn Gln Arg Ser Gln Arg Ser Trp Arg Leu Ala Cys
        835             840                 845

Glu Ser Ala Ser Ser Thr Glu Val Ser Gly Ala Leu Lys Ser Thr Ser
850                 855                 860

Cys Ser Ile Asn His Pro Ile Phe Pro Glu Asn Ser Glu Val Thr Phe
865                 870             875                 880

Asn Ile Thr Phe Asp Val Asp Ser Lys Ala Ser Leu Gly Asn Lys Leu
            885             890                 895

Leu Leu Lys Ala Asn Val Thr Ser Glu Asn Asn Met Pro Arg Thr Asn
            900             905                 910

Lys Thr Glu Phe Gln Leu Glu Leu Pro Val Lys Tyr Ala Val Tyr Met
        915             920             925

Val Val Thr Ser His Gly Val Ser Thr Lys Tyr Leu Asn Phe Thr Ala
930                 935             940

Ser Glu Asn Thr Ser Arg Val Met Gln His Gln Tyr Gln Val Ser Asn
945             950             955             960

Leu Gly Gln Arg Ser Leu Pro Ile Ser Leu Val Phe Leu Val Pro Val
            965             970             975

Arg Leu Asn Gln Thr Val Ile Trp Asp Arg Pro Gln Val Thr Phe Ser
        980             985             990

Glu Asn Leu Ser Ser Thr Cys His Thr Lys Glu Arg Leu Pro Ser His
        995             1000                1005

Ser Asp Phe Leu Ala Glu Leu Arg Lys Ala Pro Val Val Asn Cys Ser
    1010                1015                1020

Ile Ala Val Cys Gln Arg Ile Gln Cys Asp Ile Pro Phe Phe Gly Ile
1025                1030                1035                1040

Gln Glu Glu Phe Asn Ala Thr Leu Lys Gly Asn Leu Ser Phe Asp Trp
            1045                1050                1055

Tyr Ile Lys Thr Ser His Asn His Leu Leu Ile Val Ser Thr Ala Glu
        1060                1065                1070

Ile Leu Phe Asn Asp Ser Val Phe Thr Leu Leu Pro Gly Gln Gly Ala
        1075                1080                1085

Phe Val Arg Ser Gln Thr Glu Thr Lys Val Glu Pro Phe Glu Val Pro
    1090                1095                1100

Asn Pro Leu Pro Leu Ile Val Gly Ser Ser Val Gly Gly Leu Leu Leu
1105                1110                1115                1120

Leu Ala Leu Ile Thr Ala Ala Leu Tyr Lys Leu Gly Phe Phe Lys Arg
            1125                1130                1135

Gln Tyr Lys Asp Met Met Ser Glu Gly Gly Pro Pro Gly Ala Glu Pro
            1140                1145                1150

Gln ( 2 ) INFORMATION FOR SEQ ID NO:4:

( i ) SEQUENCE CHARACTERISTICS:
        ( A ) LENGTH: 1163 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met Thr Arg Thr Arg Ala Ala Leu Leu Leu Phe Thr Ala Leu Ala Thr
 1               5                  10                  15

Ser Leu Gly Phe Asn Leu Asp Thr Glu Glu Leu Thr Ala Phe Arg Val
            20                  25                  30

Asp Ser Ala Gly Phe Gly Asp Ser Val Val Gln Tyr Ala Asn Ser Trp
        35                  40                  45

Val Val Gly Ala Pro Gln Lys Ile Ile Ala Ala Asn Gln Ile Gly
 50                  55                  60

Gly Leu Tyr Gln Cys Gly Tyr Ser Thr Gly Ala Cys Glu Pro Ile Gly
 65                  70                  75                  80

Leu Gln Val Pro Pro Glu Ala Val Asn Met Ser Leu Gly Leu Ser Leu
                85                  90                  95

Ala Ser Thr Thr Ser Pro Ser Gln Leu Leu Ala Cys Gly Pro Thr Val
            100                 105                 110

His His Glu Cys Gly Arg Asn Met Tyr Leu Thr Gly Leu Cys Phe Leu
        115                 120                 125

Leu Gly Pro Thr Gln Leu Thr Gln Arg Leu Pro Val Ser Arg Gln Glu
130                 135                 140

Cys Pro Arg Gln Glu Gln Asp Ile Val Phe Leu Ile Asp Gly Ser Gly
145                 150                 155                 160

Ser Ile Ser Ser Arg Asn Phe Ala Thr Met Met Asn Phe Val Arg Ala
                165                 170                 175

Val Ile Ser Gln Phe Gln Arg Pro Ser Thr Gln Phe Ser Leu Met Gln
            180                 185                 190

Phe Ser Asn Lys Phe Gln Thr His Phe Thr Phe Glu Glu Phe Arg Arg
        195                 200                 205

Thr Ser Asn Pro Leu Ser Leu Leu Ala Ser Val His Gln Leu Gln Gly
210                 215                 220

Phe Thr Tyr Thr Ala Thr Ala Ile Gln Asn Val Val His Arg Leu Phe
225                 230                 235                 240

His Ala Ser Tyr Gly Ala Arg Arg Asp Ala Ile Lys Ile Leu Ile Val
                245                 250                 255

Ile Thr Asp Gly Lys Lys Glu Gly Asp Ser Leu Asp Tyr Lys Asp Val
            260                 265                 270

Ile Pro Met Ala Asp Ala Ala Gly Ile Ile Arg Tyr Ala Ile Gly Val
        275                 280                 285

Gly Leu Ala Phe Gln Asn Arg Asn Ser Trp Lys Glu Leu Asn Asp Ile
290                 295                 300

Ala Ser Lys Pro Ser Gln Glu His Ile Phe Lys Val Glu Asp Phe Asp
305                 310                 315                 320

Ala Leu Lys Asp Ile Gln Asn Gln Leu Lys Glu Lys Ile Phe Ala Ile
                325                 330                 335

Glu Gly Thr Glu Thr Ile Ser Ser Ser Ser Phe Glu Leu Glu Met Ala
            340                 345                 350
```

-continued

| | | | | | | | | | | | | | | |
|---|---|---|---|---|---|---|---|---|---|---|---|---|---|---|
| Gln | Glu | Gly 355 | Phe | Ser | Ala | Val | Phe 360 | Thr | Pro | Asp | Gly 365 | Pro | Val | Leu | Gly |
| Ala | Val 370 | Gly | Ser | Phe | Thr | Trp 375 | Ser | Gly | Gly | Ala | Phe 380 | Leu | Tyr | Pro | Pro |
| Asn 385 | Met | Ser | Pro | Thr | Phe 390 | Ile | Asn | Met | Ser | Gln 395 | Glu | Asn | Val | Asp | Met 400 |
| Arg | Asp | Ser | Tyr | Leu 405 | Gly | Tyr | Ser | Thr | Glu 410 | Leu | Ala | Leu | Trp | Lys 415 | Gly |
| Val | Gln | Ser | Leu 420 | Val | Leu | Gly | Ala | Pro 425 | Arg | Tyr | Gln | His | Ile 430 | Gly | Lys |
| Ala | Val | Ile 435 | Phe | Ile | Gln | Val | Ser 440 | Arg | Gln | Trp | Arg | Met 445 | Lys | Ala | Glu |
| Val | Ile 450 | Gly | Thr | Gln | Ile | Gly 455 | Ser | Tyr | Phe | Gly | Ala 460 | Ser | Leu | Cys | Ser |
| Val 465 | Asp | Val | Asp | Thr | Asp 470 | Gly | Ser | Thr | Asp | Leu 475 | Val | Leu | Ile | Gly | Ala 480 |
| Pro | His | Tyr | Tyr | Glu 485 | Gln | Thr | Arg | Gly | Gly 490 | Gln | Val | Ser | Val | Cys 495 | Pro |
| Leu | Pro | Arg | Gly 500 | Trp | Arg | Arg | Trp 505 | Cys | Asp | Ala | Val | Leu 510 | Tyr | Gly | |
| Glu | Gln | Gly 515 | His | Pro | Trp | Gly | Arg 520 | Phe | Gly | Ala | Ala | Leu 525 | Thr | Val | Leu |
| Gly | Asp 530 | Val | Asn | Gly | Asp | Lys 535 | Leu | Thr | Asp | Val | Val 540 | Ile | Gly | Ala | Pro |
| Gly 545 | Glu | Glu | Glu | Asn | Arg 550 | Gly | Ala | Val | Tyr | Leu 555 | Phe | His | Gly | Val | Leu 560 |
| Gly | Pro | Ser | Ile | Ser 565 | Pro | Ser | His | Ser | Gln 570 | Arg | Ile | Ala | Gly | Ser 575 | Gln |
| Leu | Ser | Ser | Arg 580 | Leu | Gln | Tyr | Phe | Gly 585 | Gln | Ala | Leu | Ser | Gly 590 | Gly | Gln |
| Asp | Leu | Thr 595 | Gln | Asp | Gly | Leu | Val 600 | Asp | Leu | Ala | Val | Gly 605 | Ala | Arg | Gly |
| Gln | Val 610 | Leu | Leu | Leu | Arg | Thr 615 | Arg | Pro | Val | Leu | Trp 620 | Val | Gly | Val | Ser |
| Met 625 | Gln | Phe | Ile | Pro | Ala 630 | Glu | Ile | Pro | Arg | Ser 635 | Ala | Phe | Glu | Cys | Arg 640 |
| Glu | Gln | Val | Val | Ser 645 | Glu | Gln | Thr | Leu | Val 650 | Gln | Ser | Asn | Ile | Cys 655 | Leu |
| Tyr | Ile | Asp | Lys 660 | Arg | Ser | Lys | Asn | Leu 665 | Leu | Gly | Ser | Arg | Asp 670 | Leu | Gln |
| Ser | Ser | Val 675 | Thr | Leu | Asp | Leu | Ala 680 | Leu | Ala | Pro | Gly | Arg 685 | Leu | Ser | Pro |
| Arg | Ala 690 | Ile | Phe | Gln | Glu | Thr 695 | Lys | Asn | Arg | Ser | Leu 700 | Ser | Arg | Val | Arg |
| Val 705 | Leu | Gly | Leu | Lys | Ala 710 | His | Cys | Glu | Asn | Phe 715 | Asn | Leu | Leu | Leu | Pro 720 |
| Ser | Cys | Val | Glu | Asp 725 | Ser | Val | Ile | Pro | Ile 730 | Ile | Leu | Arg | Leu | Asn 735 | Phe |
| Thr | Leu | Val | Gly 740 | Lys | Pro | Leu | Leu | Ala 745 | Phe | Arg | Asn | Leu | Arg 750 | Pro | Met |
| Leu | Ala | Ala 755 | Leu | Ala | Gln | Arg | Tyr 760 | Phe | Thr | Ala | Ser | Leu 765 | Pro | Phe | Glu |
| Lys | Asn | Cys | Gly | Ala | Asp | His | Ile | Cys | Gln | Asp | Asn | Leu | Gly | Ile | Ser |

-continued

|  |  |  | 770 |  |  |  |  | 775 |  |  |  |  | 780 |  |  |
|---|---|---|---|---|---|---|---|---|---|---|---|---|---|---|---|
| Phe | Ser | Phe | Pro | Gly | Leu | Lys | Ser | Leu | Leu | Val | Gly | Ser | Asn | Leu | Glu |
| 785 |  |  |  |  | 790 |  |  |  |  | 795 |  |  |  |  | 800 |
| Leu | Asn | Ala | Glu | Val | Met | Val | Trp | Asn | Asp | Gly | Glu | Asp | Ser | Tyr | Gly |
|  |  |  |  | 805 |  |  |  |  | 810 |  |  |  |  | 815 |  |
| Thr | Thr | Ile | Thr | Phe | Ser | His | Pro | Ala | Gly | Leu | Ser | Tyr | Arg | Tyr | Val |
|  |  |  | 820 |  |  |  |  | 825 |  |  |  |  | 830 |  |  |
| Ala | Glu | Gly | Gln | Lys | Gln | Gly | Gln | Leu | Arg | Ser | Leu | His | Leu | Thr | Cys |
|  |  | 835 |  |  |  |  | 840 |  |  |  |  | 845 |  |  |  |
| Cys | Ser | Ala | Pro | Val | Gly | Ser | Gln | Gly | Thr | Trp | Ser | Thr | Ser | Cys | Arg |
|  | 850 |  |  |  |  | 855 |  |  |  |  | 860 |  |  |  |  |
| Ile | Asn | His | Leu | Ile | Phe | Arg | Gly | Gly | Ala | Gln | Ile | Thr | Phe | Leu | Ala |
| 865 |  |  |  |  | 870 |  |  |  |  | 875 |  |  |  |  | 880 |
| Thr | Phe | Asp | Val | Ser | Pro | Lys | Ala | Val | Gly | Leu | Asp | Arg | Leu | Leu | Leu |
|  |  |  |  | 885 |  |  |  |  | 890 |  |  |  |  | 895 |  |
| Ile | Ala | Asn | Val | Ser | Ser | Glu | Asn | Asn | Ile | Pro | Arg | Thr | Ser | Lys | Thr |
|  |  |  | 900 |  |  |  |  | 905 |  |  |  |  | 910 |  |  |
| Ile | Phe | Gln | Leu | Glu | Leu | Pro | Val | Lys | Tyr | Ala | Val | Tyr | Ile | Val | Val |
|  |  | 915 |  |  |  |  | 920 |  |  |  |  | 925 |  |  |  |
| Ser | Ser | His | Glu | Gln | Phe | Thr | Lys | Tyr | Leu | Asn | Phe | Ser | Glu | Ser | Glu |
|  | 930 |  |  |  |  | 935 |  |  |  |  | 940 |  |  |  |  |
| Glu | Lys | Glu | Ser | His | Val | Ala | Met | His | Arg | Tyr | Gln | Val | Asn | Asn | Leu |
| 945 |  |  |  |  | 950 |  |  |  |  | 955 |  |  |  |  | 960 |
| Gly | Gln | Arg | Asp | Leu | Pro | Val | Ser | Ile | Asn | Phe | Trp | Val | Pro | Val | Glu |
|  |  |  |  | 965 |  |  |  |  | 970 |  |  |  |  | 975 |  |
| Leu | Asn | Gln | Glu | Ala | Val | Trp | Met | Asp | Val | Glu | Val | Ser | His | Pro | Gln |
|  |  |  | 980 |  |  |  |  | 985 |  |  |  |  | 990 |  |  |
| Asn | Pro | Ser | Leu | Arg | Cys | Ser | Ser | Glu | Lys | Ile | Ala | Pro | Pro | Ala | Ser |
|  |  | 995 |  |  |  |  | 1000 |  |  |  |  | 1005 |  |  |  |
| Asp | Phe | Leu | Ala | His | Ile | Gln | Lys | Asn | Pro | Val | Leu | Asp | Cys | Ser | Ile |
|  |  | 1010 |  |  |  |  | 1015 |  |  |  |  | 1020 |  |  |  |
| Ala | Gly | Cys | Leu | Arg | Phe | Arg | Cys | Asp | Val | Pro | Ser | Phe | Ser | Val | Gln |
| 1025 |  |  |  |  | 1030 |  |  |  |  | 1035 |  |  |  |  | 1040 |
| Glu | Glu | Leu | Asp | Phe | Thr | Leu | Lys | Gly | Asn | Leu | Ser | Phe | Gly | Trp | Val |
|  |  |  |  | 1045 |  |  |  |  | 1050 |  |  |  |  | 1055 |  |
| Arg | Gln | Ile | Leu | Gln | Lys | Lys | Val | Ser | Val | Val | Ser | Val | Ala | Glu | Ile |
|  |  |  | 1060 |  |  |  |  | 1065 |  |  |  |  | 1070 |  |  |
| Ile | Phe | Asp | Thr | Ser | Val | Tyr | Ser | Gln | Leu | Pro | Gly | Gln | Glu | Ala | Phe |
|  |  | 1075 |  |  |  |  | 1080 |  |  |  |  | 1085 |  |  |  |
| Met | Arg | Ala | Gln | Thr | Ile | Thr | Val | Leu | Glu | Lys | Tyr | Lys | Val | His | Asn |
|  |  | 1090 |  |  |  |  | 1095 |  |  |  |  | 1100 |  |  |  |
| Pro | Ile | Pro | Leu | Ile | Val | Gly | Ser | Ser | Ile | Gly | Gly | Leu | Leu | Leu | Leu |
| 1105 |  |  |  |  | 1110 |  |  |  |  | 1115 |  |  |  |  | 1120 |
| Ala | Leu | Ile | Thr | Ala | Val | Leu | Tyr | Lys | Val | Gly | Phe | Phe | Lys | Arg | Gln |
|  |  |  |  | 1125 |  |  |  |  | 1130 |  |  |  |  | 1135 |  |
| Tyr | Lys | Glu | Met | Met | Glu | Glu | Ala | Asn | Gly | Gln | Ile | Ala | Pro | Glu | Asn |
|  |  |  | 1140 |  |  |  |  | 1145 |  |  |  |  | 1150 |  |  |
| Gly | Thr | Gln | Thr | Pro | Ser | Pro | Ser | Glu | Lys |  |  |  |  |  |  |
|  |  | 1155 |  |  |  |  | 1160 |  |  |  |  |  |  |  |  |

( 2 ) INFORMATION FOR SEQ ID NO:5:

( i ) SEQUENCE CHARACTERISTICS:
( A ) LENGTH: 12 amino acids (B) TYPE: amino acid
(D) TOPOLOGY: linear (ii) MOLECULE TYPE: peptide (xi) SEQUENCE DESCRIPTION: SEQ ID NO:5:

Phe Asn Leu Asp Val Glu Glu Pro Met Val Phe Gln
1               5                   10

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

TTYAAYYTGG AYGTNGARGA RCCNATGGTN TTYCA                    35

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TTCAACCTGG ACGTGGAGGA GCCCATGGTG TTCCAA                    36

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

TTCAACCTGG ACGTNGAASA NCCCATGGTC TTCCAA                    36

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

TTYAAYYTNG AYGTNGARGA RCC                                  23

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear

```
        ( i i ) MOLECULE TYPE: DNA ( x i ) SEQUENCE DESCRIPTION: SEQ ID NO:10:

TTYAAYYTGG ACGTNGAAGA                                                                    20

( 2 ) INFORMATION FOR SEQ ID NO:11:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:11:

TGRAANACCA TNGGYTC                                                                       17

( 2 ) INFORMATION FOR SEQ ID NO:12:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:12:

TTGGAAGACC ATNGGYTC                                                                      18

( 2 ) INFORMATION FOR SEQ ID NO:13:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:13:

ATTAACCCTC ACTAAAG                                                                       17

( 2 ) INFORMATION FOR SEQ ID NO:14:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:14:

AATACGACTC ACTATAG                                                                       17

( 2 ) INFORMATION FOR SEQ ID NO:15:

( i ) SEQUENCE CHARACTERISTICS:
                ( A ) LENGTH: 11 amino acids
                ( B ) TYPE: amino acid
                ( D ) TOPOLOGY: linear ( i i ) MOLECULE TYPE: peptide ( x i ) SEQUENCE DESCRIPTION: SEQ ID NO:15:

Val  Phe  Gln  Glu  Xaa  Gly  Ala  Gly  Phe  Gly  Gln
```

(2) INFORMATION FOR SEQ ID NO:16:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:16:

```
Leu  Tyr  Asp  Xaa  Val  Ala  Ala  Thr  Gly  Leu  Xaa  Gln  Pro  Ile
 1                   5                        10
```

(2) INFORMATION FOR SEQ ID NO:17:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:17:

```
Pro  Leu  Glu  Tyr  Xaa  Asp  Val  Ile  Pro  Gln  Ala  Glu
 1                   5                        10
```

(2) INFORMATION FOR SEQ ID NO:18:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:18:

```
Phe  Gln  Glu  Gly  Phe  Ser  Xaa  Val  Leu  Xaa
 1                   5                        10
```

(2) INFORMATION FOR SEQ ID NO:19:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:19:

```
Thr  Ser  Pro  Thr  Phe  Ile  Xaa  Met  Ser  Gln  Glu  Asn  Val  Asp
 1                   5                        10
```

(2) INFORMATION FOR SEQ ID NO:20:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:20:

```
Leu  Val  Val  Gly  Ala  Pro  Leu  Glu  Val  Val  Ala  Val  Xaa  Gln  Thr  Gly
 1                   5                        10                       15
Arg
```

( 2 ) INFORMATION FOR SEQ ID NO:21:

( i ) SEQUENCE CHARACTERISTICS:
  ( A ) LENGTH: 9 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:21:

Leu Asp Xaa Lys Pro Xaa Asp Thr Ala
  1               5

( 2 ) INFORMATION FOR SEQ ID NO:22:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:22:

Phe Gly Glu Gln Phe Ser Glu
  1               5

( 2 ) INFORMATION FOR SEQ ID NO:23:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:23:

RAANCCYTCY TGRAAACTYT C                                                                 21

( 2 ) INFORMATION FOR SEQ ID NO:24:

( i ) SEQUENCE CHARACTERISTICS:
  ( A ) LENGTH: 1006 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:24:

| | | | | | |
|---|---|---|---|---|---|
| TTCAACCTGG | ACGTGGAGGA | GCCCATGGTG | TTCAAGAGGA | TGGAGCTGGC | TTTGGACAGA | 60 |
| GCGTGGCCCA | GCTTGGCGGA | TCTAGACTCG | TGGTGGGAGC | CCCCCTGGAG | GTGGTGGCGG | 120 |
| TCAACCAAAC | AGGAAGGTTG | TATGACTGTG | TGGCTGCCAC | TGGCCTTGTC | AACCCATACC | 180 |
| CCTGCACACA | CCCCCAGATG | CTGTGAACAT | GTCCCTGGGT | CTGTCCCTGT | CAGCCGCCGC | 240 |
| CAGTCGCCCC | TGGCTGCTGG | CCTGTGGCCC | AACCATGCAC | AGAGCCTGTG | GGGAGAATAT | 300 |
| GTATGCAGAA | GGCTTTTGCC | TCCTGTTGGA | CTCCCATCTG | CAGACCATTT | GGACAGTACC | 360 |
| TGCTGCCCTA | CCAGAGTGTC | CAAGTCAAGA | GATGGACATT | GTCTTCCTGA | TTGATGGTTC | 420 |
| TGGCAGTATG | AGCAAAGTGA | CTTTAAACAA | ATGAAGGATT | TGTGAGAGCT | GTGATGGGAC | 480 |
| AGTTTGAGGG | CACCCAAACC | CTGTTCTCAC | TGATACAGTA | TCCCACCTCC | CTGAAGATCC | 540 |
| ACTTCACCTT | CACGCAATTC | CAGAGCAGCT | GGAACCCTCT | GAGCCTGGTG | GATCCCATTG | 600 |

-continued

| | | | | | | |
|---|---|---|---|---|---|---|
| TCCAACTGGA | CGGCCTGACA | TATACAGCCA | CGGGCATCCG | GAAAGTGGTG | GAGGAACTGT | 660 |
| TTCATAGTAA | GAATGGGGCC | CGTAAAAGTG | CCAAGAAGAT | CCTCATTGTC | ATCACAGATG | 720 |
| GCAAAAATAC | AAAGACCCCC | TGGAGTACGA | GGACGTATCC | CCAGGCAGAG | AGAGCGGATC | 780 |
| ATCCGCTATG | CCATTGGGGT | GGGAGATGCT | TTCTGGAAAC | CCAGTGCCAA | GCAGGAGCTG | 840 |
| GACAACATTG | GCTCAGAGCC | GGCTCAGGAC | CATGTGTTCA | GGGTGGACAA | CTTTGCAGCA | 900 |
| CTCAGCAGCA | TCCAGGAGCA | GCTGCAGGAG | AAGATCTTTG | CACTCGAAGG | AACCCAGTCG | 960 |
| ACGACAAGTA | GCTCTTTCCA | ACATGAGATG | TTCCAAGAAG | GGTTCA | | 1006 |

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

| | |
|---|---|
| GTNTTYCARG ARGAYGG | 17 |

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

| | |
|---|---|
| CCACTGTCAG GATGCCCGTG | 20 |

( 2 ) INFORMATION FOR SEQ ID NO:27:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

| | |
|---|---|
| AGTTACGAAT TCGCCACCAT GGCTCTACGG GTGCTTCTTC TG | 42 |

( 2 ) INFORMATION FOR SEQ ID NO:28:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

| | |
|---|---|
| AGTTACGAAT TCGCCACCAT GACTCGGACT GTGCTTCTTC TG | 42 |

( 2 ) INFORMATION FOR SEQ ID NO:29:

( i ) SEQUENCE CHARACTERISTICS:
        ( A ) LENGTH: 36 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:29:

AGTTACGAAT TCGCCACCAT GACCTTCGGC ACTGTG　　　　　　　　　　36

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

TTGCTGACTG CCTGCAGTTC　　　　　　　　　　20

(2) INFORMATION FOR SEQ ID NO:31:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

GTTCTGACGC GTAATGGCAT TGTAGACCTC GTCTTC　　　　　　　　　　36

(2) INFORMATION FOR SEQ ID NO:32:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

ACGTATGCAG GATCCCATCA AGAGATGGAC ATCGCT　　　　　　　　　　36

(2) INFORMATION FOR SEQ ID NO:33:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

ACTGCATGTC TCGAGGCTGA AGCCTTCTTG GGACATC　　　　　　　　　　37

(2) INFORMATION FOR SEQ ID NO:34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

TATAGACTGC TGGGTAGTCC CCAC 24

(2) INFORMATION FOR SEQ ID NO:35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

TGAAGATTGG GGGTAAATAA CAGA 24

(2) INFORMATION FOR SEQ ID NO:36:

(i) SEQUENCE CHARACTERISTICS:
        (A) LENGTH: 3528 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..3456

(xi) SEQUENCE DESCRIPTION: SEQ ID NO:36:

```
GGC TGG GCC CTG GCT TCC TGT CAT GGG TCT AAC CTG GAT GTG GAG GAA    48
Gly Trp Ala Leu Ala Ser Cys His Gly Ser Asn Leu Asp Val Glu Glu
 1               5                  10                  15

CCC ATC GTG TTC AGA GAG GAT GCA GCC AGC TTT GGA CAG ACT GTG GTG    96
Pro Ile Val Phe Arg Glu Asp Ala Ala Ser Phe Gly Gln Thr Val Val
             20                  25                  30

CAG TTT GGT GGA TCT CGA CTC GTG GTG GGA GCC CCT CTG GAG GCG GTG   144
Gln Phe Gly Gly Ser Arg Leu Val Val Gly Ala Pro Leu Glu Ala Val
         35                  40                  45

GCA GTC AAC CAA ACA GGA CGG TTG TAT GAC TGT GCA CCT GCC ACT GGC   192
Ala Val Asn Gln Thr Gly Arg Leu Tyr Asp Cys Ala Pro Ala Thr Gly
     50                  55                  60

ATG TGC CAG CCC ATC GTA CTG CGC AGT CCC CTA GAG GCA GTG AAC ATG   240
Met Cys Gln Pro Ile Val Leu Arg Ser Pro Leu Glu Ala Val Asn Met
 65                  70                  75                  80

TCC CTG GGC CTG TCT CTG GTG ACT GCC ACC AAT AAC GCC CAG TTG CTG   288
Ser Leu Gly Leu Ser Leu Val Thr Ala Thr Asn Asn Ala Gln Leu Leu
                 85                  90                  95

GCT TGT GGT CCA ACT GCA CAG AGA GCT TGT GTG AAG AAC ATG TAT GCG   336
Ala Cys Gly Pro Thr Ala Gln Arg Ala Cys Val Lys Asn Met Tyr Ala
            100                 105                 110

AAA GGT TCC TGC CTC CTT CTC GGC TCC AGC TTG CAG TTC ATC CAG GCA   384
Lys Gly Ser Cys Leu Leu Leu Gly Ser Ser Leu Gln Phe Ile Gln Ala
        115                 120                 125

GTC CCT GCC TCC ATG CCA GAG TGT CCA AGA CAA GAG ATG GAC ATT GCT   432
Val Pro Ala Ser Met Pro Glu Cys Pro Arg Gln Glu Met Asp Ile Ala
    130                 135                 140

TTC CTG ATT GAT GGT TCT GGC AGC ATT AAC CAA AGG GAC TTT GCC CAG   480
Phe Leu Ile Asp Gly Ser Gly Ser Ile Asn Gln Arg Asp Phe Ala Gln
145                 150                 155                 160

ATG AAG GAC TTT GTC AAA GCT TTG ATG GGA GAG TTT GCG AGC ACC AGC   528
```

```
Met Lys Asp Phe Val Lys Ala Leu Met Gly Glu Phe Ala Ser Thr Ser
            165                 170                 175

ACC TTG TTC TCC CTG ATG CAA TAC TCG AAC ATC CTG AAG ACC CAT TTT    576
Thr Leu Phe Ser Leu Met Gln Tyr Ser Asn Ile Leu Lys Thr His Phe
        180                 185                 190

ACC TTC ACT GAA TTC AAG AAC ATC CTG GAC CCT CAG AGC CTG GTG GAT    624
Thr Phe Thr Glu Phe Lys Asn Ile Leu Asp Pro Gln Ser Leu Val Asp
            195                 200                 205

CCC ATT GTC CAG CTG CAA GGC CTG ACC TAC ACA GCC ACA GGC ATC CGG    672
Pro Ile Val Gln Leu Gln Gly Leu Thr Tyr Thr Ala Thr Gly Ile Arg
    210                 215                 220

ACA GTG ATG GAA GAG CTA TTT CAT AGC AAG AAT GGG TCC CGT AAA AGT    720
Thr Val Met Glu Glu Leu Phe His Ser Lys Asn Gly Ser Arg Lys Ser
225                 230                 235                 240

GCC AAG AAG ATC CTC CTT GTC ATC ACA GAT GGG CAG AAA TAC AGA GAC    768
Ala Lys Lys Ile Leu Leu Val Ile Thr Asp Gly Gln Lys Tyr Arg Asp
                245                 250                 255

CCC CTG GAG TAT AGT GAT GTC ATT CCC GCC GCA GAC AAA GCT GGC ATC    816
Pro Leu Glu Tyr Ser Asp Val Ile Pro Ala Ala Asp Lys Ala Gly Ile
            260                 265                 270

ATT CGT TAT GCT ATT GGG GTG GGA GAT GCC TTC CAG GAG CCC ACT GCC    864
Ile Arg Tyr Ala Ile Gly Val Gly Asp Ala Phe Gln Glu Pro Thr Ala
        275                 280                 285

CTG AAG GAG CTG AAC ACC ATT GGC TCA GCT CCC CCA CAG GAC CAC GTG    912
Leu Lys Glu Leu Asn Thr Ile Gly Ser Ala Pro Pro Gln Asp His Val
    290                 295                 300

TTC AAG GTA GGC AAC TTT GCA GCA CTT CGC AGC ATC CAG AGG CAA CTT    960
Phe Lys Val Gly Asn Phe Ala Ala Leu Arg Ser Ile Gln Arg Gln Leu
305                 310                 315                 320

CAG GAG AAA ATC TTC GCC ATT GAG GGA ACT CAA TCA AGG TCA AGT AGT   1008
Gln Glu Lys Ile Phe Ala Ile Glu Gly Thr Gln Ser Arg Ser Ser Ser
                325                 330                 335

TCC TTT CAG CAC GAG ATG TCA CAA GAA GGT TTC AGT TCA GCT CTC ACA   1056
Ser Phe Gln His Glu Met Ser Gln Glu Gly Phe Ser Ser Ala Leu Thr
            340                 345                 350

TCG GAT GGA CCC GTT CTG GGG GCC GYG GGA AGC TTC AGC TGG TCC GGA   1104
Ser Asp Gly Pro Val Leu Gly Ala Xaa Gly Ser Phe Ser Trp Ser Gly
        355                 360                 365

GGT GCC TTC TTA TAT CCC CCA AAT ACG AGA CCC ACC TTT ATC AAC ATG   1152
Gly Ala Phe Leu Tyr Pro Pro Asn Thr Arg Pro Thr Phe Ile Asn Met
    370                 375                 380

TCT CAG GAG AAT GTG GAC ATG AGA GAC TCC TAC CTG GGT TAC TCC ACC   1200
Ser Gln Glu Asn Val Asp Met Arg Asp Ser Tyr Leu Gly Tyr Ser Thr
385                 390                 395                 400

GCA GTG GCC TTT TGG AAG GGG GTT CAC AGC CTG ATC CTG GGG GCC CCG   1248
Ala Val Ala Phe Trp Lys Gly Val His Ser Leu Ile Leu Gly Ala Pro
                405                 410                 415

CGT CAC CAG CAC ACG GGG AAG GTT GTC ATC TTT ACC CAG GAA GCC AGG   1296
Arg His Gln His Thr Gly Lys Val Val Ile Phe Thr Gln Glu Ala Arg
            420                 425                 430

CAT TGG AGG CCC AAG TCT GAA GTC AGA GGG ACA CAG ATC GGC TCC TAC   1344
His Trp Arg Pro Lys Ser Glu Val Arg Gly Thr Gln Ile Gly Ser Tyr
        435                 440                 445

TTC GGG GCC TCT CTC TGT TCT GTG GAC GTG GAT AGA GAT GGC AGC ACY   1392
Phe Gly Ala Ser Leu Cys Ser Val Asp Val Asp Arg Asp Gly Ser Xaa
    450                 455                 460

GAC CTG GTC CTG ATC GGA GCC CCC CAT TAC TAT GAG CAG ACC CGA GGG   1440
Asp Leu Val Leu Ile Gly Ala Pro His Tyr Tyr Glu Gln Thr Arg Gly
465                 470                 475                 480
```

| | | | | | | | | | | | | | | | | |
|---|---|---|---|---|---|---|---|---|---|---|---|---|---|---|---|---|
| GGG | CAG | GTC | TCA | GTG | TKC | CCC | GTG | CCC | GGT | GTG | AGG | GGC | AGG | TGG | CAG | 1488 |
| Gly | Gln | Val | Ser | Val<br>485 | Xaa | Pro | Val | Pro<br>490 | Gly | Val | Arg | Gly | Arg | Trp<br>495 | Gln | |
| TGT | GAG | GCC | ACC | CTC | CAC | GGG | GAG | CAG | GRC | CAT | CCT | TGG | GGC | CGC | TTT | 1536 |
| Cys | Glu | Ala | Thr<br>500 | Leu | His | Gly | Glu | Gln<br>505 | Xaa | His | Pro | Trp | Gly<br>510 | Arg | Phe | |
| GGG | GTG | GCT | CTG | ACA | GTG | CTG | GGG | GAC | GTA | AAC | GGG | GAC | AAT | CTG | GCA | 1584 |
| Gly | Val | Ala<br>515 | Leu | Thr | Val | Leu<br>520 | Gly | Asp | Val | Asn | Gly<br>525 | Asp | Asn | Leu | Ala | |
| GAC | GTG | GCT | ATT | GGT | GCC | CCT | GGA | GAG | GAG | GAG | AGC | AGA | GGT | GCT | GTC | 1632 |
| Asp | Val<br>530 | Ala | Ile | Gly | Ala | Pro<br>535 | Gly | Glu | Glu | Glu | Ser<br>540 | Arg | Gly | Ala | Val | |
| TAC | ATA | TTT | CAT | GGA | GCC | TCG | AGA | CTG | GAG | ATC | ATG | CCC | TCA | CCC | AGC | 1680 |
| Tyr<br>545 | Ile | Phe | His | Gly | Ala<br>550 | Ser | Arg | Leu | Glu | Ile<br>555 | Met | Pro | Ser | Pro | Ser<br>560 | |
| CAG | CGG | GTC | ACT | GGC | TCC | CAG | CTC | TCC | CTG | AGA | CTG | CAG | TAT | TTT | GGG | 1728 |
| Gln | Arg | Val | Thr | Gly<br>565 | Ser | Gln | Leu | Ser | Leu<br>570 | Arg | Leu | Gln | Tyr | Phe<br>575 | Gly | |
| CAG | TCA | TTG | AGT | GGG | GGT | CAG | GAC | CTT | ACA | CAG | GAT | GGC | CTG | GTG | GAC | 1776 |
| Gln | Ser | Leu | Ser<br>580 | Gly | Gly | Gln | Asp | Leu<br>585 | Thr | Gln | Asp | Gly | Leu<br>590 | Val | Asp | |
| CTG | GCC | GTG | GGA | GCC | CAG | GGG | CAC | GTA | CTG | CTC | CTC | AGG | AGT | CTG | CCT | 1824 |
| Leu | Ala | Val<br>595 | Gly | Ala | Gln | Gly<br>600 | His | Val | Leu | Leu | Leu<br>605 | Arg | Ser | Leu | Pro | |
| CTG | CTG | AAA | GTG | GAG | CTC | TCC | ATA | AGA | TTC | GCC | CCC | ATG | GAG | GTG | GCA | 1872 |
| Leu<br>610 | Leu | Lys | Val | Glu | Leu<br>615 | Ser | Ile | Arg | Phe | Ala<br>620 | Pro | Met | Glu | Val | Ala | |
| AAG | GCT | GTG | TAC | CAG | TGC | TGG | GAA | AGG | ACT | CCC | ACT | GTC | CTC | GAA | GCT | 1920 |
| Lys<br>625 | Ala | Val | Tyr | Gln | Cys<br>630 | Trp | Glu | Arg | Thr | Pro<br>635 | Thr | Val | Leu | Glu | Ala<br>640 | |
| GGA | GAG | GCC | ACT | GTC | TGT | CTC | ACT | GTC | CAC | AAA | GGC | TCA | CCT | GAC | CTG | 1968 |
| Gly | Glu | Ala | Thr | Val<br>645 | Cys | Leu | Thr | Val | His<br>650 | Lys | Gly | Ser | Pro | Asp<br>655 | Leu | |
| TTA | GGT | AAT | GTC | CAA | GGC | TCT | GTC | AGG | TAT | GAT | CTG | GCG | TTA | GAT | CCG | 2016 |
| Leu | Gly | Asn | Val<br>660 | Gln | Gly | Ser | Val | Arg<br>665 | Tyr | Asp | Leu | Ala | Leu<br>670 | Asp | Pro | |
| GGC | CGC | CTG | ATT | TCT | CGT | GCC | ATT | TTT | GAT | GAG | ACT | AAG | AAC | TGC | ACT | 2064 |
| Gly | Arg | Leu<br>675 | Ile | Ser | Arg | Ala | Ile<br>680 | Phe | Asp | Glu | Thr | Lys<br>685 | Asn | Cys | Thr | |
| TTG | ACG | GGA | AGG | AAG | ACT | CTG | GGG | CTT | GGT | GAT | CAC | TGC | GAA | ACA | GTG | 2112 |
| Leu | Thr<br>690 | Gly | Arg | Lys | Thr | Leu<br>695 | Gly | Leu | Gly | Asp | His<br>700 | Cys | Glu | Thr | Val | |
| AAG | CTG | CTT | TTG | CCG | GAC | TGT | GTG | GAA | GAT | GCA | GTG | AGC | CCT | ATC | ATC | 2160 |
| Lys<br>705 | Leu | Leu | Leu | Pro | Asp<br>710 | Cys | Val | Glu | Asp | Ala<br>715 | Val | Ser | Pro | Ile | Ile<br>720 | |
| CTG | CGC | CTC | AAC | TTT | TCC | CTG | GTG | AGA | GAC | TCT | GCT | TCA | CCC | AGG | AAC | 2208 |
| Leu | Arg | Leu | Asn | Phe<br>725 | Ser | Leu | Val | Arg | Asp<br>730 | Ser | Ala | Ser | Pro | Arg<br>735 | Asn | |
| CTG | CAT | CCT | GTG | CTG | GCT | GTG | GGC | TCA | CAA | GAC | CAC | ATA | ACT | GCT | TCT | 2256 |
| Leu | His | Pro | Val<br>740 | Leu | Ala | Val | Gly | Ser<br>745 | Gln | Asp | His | Ile | Thr<br>750 | Ala | Ser | |
| CTG | CCG | TTT | GAG | AAG | AAC | TGT | AAG | CAA | GAA | CTC | CTG | TGT | GAG | GGG | GAC | 2304 |
| Leu | Pro | Phe<br>755 | Glu | Lys | Asn | Cys | Lys<br>760 | Gln | Glu | Leu | Leu | Cys<br>765 | Glu | Gly | Asp | |
| CTG | GGC | ATC | AGC | TTT | AAC | TTC | TCA | GGC | CTG | CAG | GTC | TTG | GTG | GTG | GGA | 2352 |
| Leu | Gly | Ile<br>770 | Ser | Phe | Asn | Phe | Ser<br>775 | Gly | Leu | Gln | Val | Leu<br>780 | Val | Val | Gly | |
| GGC | TCC | CCA | GAG | CTC | ACT | GTG | ACA | GTC | ACT | GTG | TGG | AAT | GAG | GGT | GAG | 2400 |
| Gly<br>785 | Ser | Pro | Glu | Leu | Thr<br>790 | Val | Thr | Val | Thr<br>795 | Val | Trp | Asn | Glu | Gly<br>800 | Glu | |

-continued

| | | | | | | | | | | | | | | | | |
|---|---|---|---|---|---|---|---|---|---|---|---|---|---|---|---|---|
| GAC | AGC | TAT | GGA | ACT | TTA | GTC | AAG | TTC | TAC | TAC | CCA | GCA | GGG | CTA | TCT | 2448 |
| Asp | Ser | Tyr | Gly | Thr | Leu | Val | Lys | Phe | Tyr | Tyr | Pro | Ala | Gly | Leu | Ser | |
| | | | | 805 | | | | 810 | | | | | | 815 | | |
| TAC | CGA | CGG | GTA | ACA | GGG | ACT | CAG | CAA | CCT | CAT | CAG | TAC | CCA | CTA | CGC | 2496 |
| Tyr | Arg | Arg | Val | Thr | Gly | Thr | Gln | Gln | Pro | His | Gln | Tyr | Pro | Leu | Arg | |
| | | | 820 | | | | | 825 | | | | | 830 | | | |
| TTG | GCC | TGT | GAG | GCT | GAG | CCC | GCT | GCC | CAG | GAG | GAC | CTG | AGG | AGC | AGC | 2544 |
| Leu | Ala | Cys | Glu | Ala | Glu | Pro | Ala | Ala | Gln | Glu | Asp | Leu | Arg | Ser | Ser | |
| | | 835 | | | | | | 840 | | | | | 845 | | | |
| AGC | TGT | AGC | ATT | AAT | CAC | CCC | ATC | TTC | CGA | GAA | GGT | GCA | AAG | ACC | ACC | 2592 |
| Ser | Cys | Ser | Ile | Asn | His | Pro | Ile | Phe | Arg | Glu | Gly | Ala | Lys | Thr | Thr | |
| | 850 | | | | | 855 | | | | | | 860 | | | | |
| TTC | ATG | ATC | ACA | TTC | GAT | GTC | TCC | TAC | AAG | GCC | TTC | CTA | GGA | GAC | AGG | 2640 |
| Phe | Met | Ile | Thr | Phe | Asp | Val | Ser | Tyr | Lys | Ala | Phe | Leu | Gly | Asp | Arg | |
| 865 | | | | | 870 | | | | 875 | | | | | | 880 | |
| TTG | CTT | CTG | AGG | GCC | AAA | GCC | AGC | AGT | GAG | AAT | AAT | AAG | CCT | GAT | ACC | 2688 |
| Leu | Leu | Leu | Arg | Ala | Lys | Ala | Ser | Ser | Glu | Asn | Asn | Lys | Pro | Asp | Thr | |
| | | | | 885 | | | | | 890 | | | | | 895 | | |
| AAC | AAG | ACT | GCC | TTC | CAG | CTG | GAG | CTC | CCA | GTG | AAG | TAC | ACC | GTC | TAT | 2736 |
| Asn | Lys | Thr | Ala | Phe | Gln | Leu | Glu | Leu | Pro | Val | Lys | Tyr | Thr | Val | Tyr | |
| | | | 900 | | | | | 905 | | | | | 910 | | | |
| ACC | CTG | ATC | AGT | AGG | CAA | GAA | GAT | TCC | ACC | AAC | CAT | GTC | AAC | TTT | TCA | 2784 |
| Thr | Leu | Ile | Ser | Arg | Gln | Glu | Asp | Ser | Thr | Asn | His | Val | Asn | Phe | Ser | |
| | | 915 | | | | | 920 | | | | | 925 | | | | |
| TCT | TCC | CAC | GGG | GGG | AGA | AGG | CAA | GAA | GCC | GCA | CAT | CGC | TAT | CGT | GTG | 2832 |
| Ser | Ser | His | Gly | Gly | Arg | Arg | Gln | Glu | Ala | Ala | His | Arg | Tyr | Arg | Val | |
| | 930 | | | | | 935 | | | | | 940 | | | | | |
| AAT | AAC | CTG | AGT | CCA | CTG | AAG | CTG | GCC | GTC | AGA | GTT | AAC | TTC | TGG | GTC | 2880 |
| Asn | Asn | Leu | Ser | Pro | Leu | Lys | Leu | Ala | Val | Arg | Val | Asn | Phe | Trp | Val | |
| 945 | | | | | 950 | | | | 955 | | | | | | 960 | |
| CCT | GTC | CTT | CTG | AAC | GGT | GTG | GCT | GTG | TGG | GAC | GTG | ACT | CTG | AGC | AGC | 2928 |
| Pro | Val | Leu | Leu | Asn | Gly | Val | Ala | Val | Trp | Asp | Val | Thr | Leu | Ser | Ser | |
| | | | | 965 | | | | | 970 | | | | | 975 | | |
| CCA | GCA | CAG | GGT | GTC | TCC | TGC | GTG | TCC | CAG | ATG | AAA | CCT | CCT | CAG | AAT | 2976 |
| Pro | Ala | Gln | Gly | Val | Ser | Cys | Val | Ser | Gln | Met | Lys | Pro | Pro | Gln | Asn | |
| | | | 980 | | | | | 985 | | | | | 990 | | | |
| CCC | GAC | TTT | CTG | ACC | CAG | ATT | CAG | AGA | CGT | TCT | GTG | CTG | GAC | TGC | TCC | 3024 |
| Pro | Asp | Phe | Leu | Thr | Gln | Ile | Gln | Arg | Arg | Ser | Val | Leu | Asp | Cys | Ser | |
| | | 995 | | | | | 1000 | | | | | 1005 | | | | |
| ATT | GCT | GAC | TGC | CTG | CAC | TCC | CGC | TGT | GAC | ATC | CCC | TCC | TTG | GAC | ATC | 3072 |
| Ile | Ala | Asp | Cys | Leu | His | Ser | Arg | Cys | Asp | Ile | Pro | Ser | Leu | Asp | Ile | |
| | 1010 | | | | | 1015 | | | | | 1020 | | | | | |
| CAG | GAT | GAA | CTT | GAC | TTC | ATT | CTG | AGG | GGC | AAC | CTC | AGC | TTC | GGC | TGG | 3120 |
| Gln | Asp | Glu | Leu | Asp | Phe | Ile | Leu | Arg | Gly | Asn | Leu | Ser | Phe | Gly | Trp | |
| 1025 | | | | | 1030 | | | | | 1035 | | | | | 1040 | |
| GTC | AGT | CAG | ACA | TTG | CAG | GAA | AAG | GTG | TTG | CTT | GTG | AGT | GAG | GCT | GAA | 3168 |
| Val | Ser | Gln | Thr | Leu | Gln | Glu | Lys | Val | Leu | Leu | Val | Ser | Glu | Ala | Glu | |
| | | | | 1045 | | | | | 1050 | | | | | 1055 | | |
| ATC | ACT | TTC | GAC | ACA | TCT | GTG | TAC | TCC | CAG | CTG | CCA | GGA | CAG | GAG | GCA | 3216 |
| Ile | Thr | Phe | Asp | Thr | Ser | Val | Tyr | Ser | Gln | Leu | Pro | Gly | Gln | Glu | Ala | |
| | | | | 1060 | | | | | 1065 | | | | | 1070 | | |
| TTT | CTG | AGA | GCC | CAG | GTG | GAG | ACA | ACG | TTA | GAA | GAA | TAC | GTG | GTC | TAT | 3264 |
| Phe | Leu | Arg | Ala | Gln | Val | Glu | Thr | Thr | Leu | Glu | Glu | Tyr | Val | Val | Tyr | |
| | | 1075 | | | | | 1080 | | | | | 1085 | | | | |
| GAG | CCC | ATC | TTC | CTC | GTG | GCG | GGC | AGC | TCG | GTG | GGA | GGT | CTG | CTG | TTA | 3312 |
| Glu | Pro | Ile | Phe | Leu | Val | Ala | Gly | Ser | Ser | Val | Gly | Gly | Leu | Leu | Leu | |
| | | 1090 | | | | | 1095 | | | | | 1100 | | | | |
| CTG | GCT | CTC | ATC | ACA | GTG | GTA | CTG | TAC | AAG | CTT | GGC | TYC | TYC | AAA | CGT | 3360 |
| Leu | Ala | Leu | Ile | Thr | Val | Val | Leu | Tyr | Lys | Leu | Gly | Xaa | Xaa | Lys | Arg | |

|  | 1105 |  |  |  | 1110 |  |  |  | 1115 |  |  |  | 1120 |  |  |
|---|---|---|---|---|---|---|---|---|---|---|---|---|---|---|---|---|
| CAG | TAC | AAA | GAA | ATG | CTG | GAC | GGC | AAG | GCT | GCA | GAT | CCT | GTC | ACA | GCC | 3408 |
| Gln | Tyr | Lys | Glu | Met | Leu | Asp | Gly | Lys | Ala | Ala | Asp | Pro | Val | Thr | Ala | |
|  |  |  |  | 1125 |  |  |  | 1130 |  |  |  |  | 1135 |  |  | |

| GGC | CAG | GCA | GAT | TTC | GGC | TGT | GAG | ACT | CCT | CCA | TAT | CTC | GTG | AGC | TAGGAATC | 3463 |
|---|---|---|---|---|---|---|---|---|---|---|---|---|---|---|---|---|
| Gly | Gln | Ala | Asp | Phe | Gly | Cys | Glu | Thr | Pro | Pro | Tyr | Leu | Val | Ser | | |
|  |  |  | 1140 |  |  |  |  | 1145 |  |  |  |  | 1150 | | | |

CTCTCCTGCC TATCTCTGNA ATGAAGATTG GTCCTGCCTA TGAGTCTACT GGCATGGGAA 3523

CGAGT 3528

(2) INFORMATION FOR SEQ ID NO:37:

(i) SEQUENCE CHARACTERISTICS:
        (A) LENGTH: 1151 amino acids
        (B) TYPE: amino acid
        (D) TOPOLOGY: linear (ii) MOLECULE TYPE: protein (xi) SEQUENCE DESCRIPTION: SEQ ID NO:37:

| Gly | Trp | Ala | Leu | Ala | Ser | Cys | His | Gly | Ser | Asn | Leu | Asp | Val | Glu | Glu |
|---|---|---|---|---|---|---|---|---|---|---|---|---|---|---|---|
| 1 |  |  |  | 5 |  |  |  |  | 10 |  |  |  |  | 15 |  |
| Pro | Ile | Val | Phe | Arg | Glu | Asp | Ala | Ala | Ser | Phe | Gly | Gln | Thr | Val | Val |
|  |  |  | 20 |  |  |  |  | 25 |  |  |  |  | 30 |  |  |
| Gln | Phe | Gly | Gly | Ser | Arg | Leu | Val | Val | Gly | Ala | Pro | Leu | Glu | Ala | Val |
|  |  | 35 |  |  |  |  | 40 |  |  |  |  | 45 |  |  |  |
| Ala | Val | Asn | Gln | Thr | Gly | Arg | Leu | Tyr | Asp | Cys | Ala | Pro | Ala | Thr | Gly |
|  | 50 |  |  |  |  | 55 |  |  |  |  | 60 |  |  |  |  |
| Met | Cys | Gln | Pro | Ile | Val | Leu | Arg | Ser | Pro | Leu | Glu | Ala | Val | Asn | Met |
| 65 |  |  |  |  | 70 |  |  |  |  | 75 |  |  |  |  | 80 |
| Ser | Leu | Gly | Leu | Ser | Leu | Val | Thr | Ala | Thr | Asn | Asn | Ala | Gln | Leu | Leu |
|  |  |  |  | 85 |  |  |  |  | 90 |  |  |  |  | 95 |  |
| Ala | Cys | Gly | Pro | Thr | Ala | Gln | Arg | Ala | Cys | Val | Lys | Asn | Met | Tyr | Ala |
|  |  |  | 100 |  |  |  |  | 105 |  |  |  |  | 110 |  |  |
| Lys | Gly | Ser | Cys | Leu | Leu | Leu | Gly | Ser | Ser | Leu | Gln | Phe | Ile | Gln | Ala |
|  |  | 115 |  |  |  |  | 120 |  |  |  |  | 125 |  |  |  |
| Val | Pro | Ala | Ser | Met | Pro | Glu | Cys | Pro | Arg | Gln | Glu | Met | Asp | Ile | Ala |
|  | 130 |  |  |  |  | 135 |  |  |  |  | 140 |  |  |  |  |
| Phe | Leu | Ile | Asp | Gly | Ser | Gly | Ser | Ile | Asn | Gln | Arg | Asp | Phe | Ala | Gln |
| 145 |  |  |  |  | 150 |  |  |  |  | 155 |  |  |  |  | 160 |
| Met | Lys | Asp | Phe | Val | Lys | Ala | Leu | Met | Gly | Glu | Phe | Ala | Ser | Thr | Ser |
|  |  |  |  | 165 |  |  |  |  | 170 |  |  |  |  | 175 |  |
| Thr | Leu | Phe | Ser | Leu | Met | Gln | Tyr | Ser | Asn | Ile | Leu | Lys | Thr | His | Phe |
|  |  |  | 180 |  |  |  |  | 185 |  |  |  |  | 190 |  |  |
| Thr | Phe | Thr | Glu | Phe | Lys | Asn | Ile | Leu | Asp | Pro | Gln | Ser | Leu | Val | Asp |
|  |  | 195 |  |  |  |  | 200 |  |  |  |  | 205 |  |  |  |
| Pro | Ile | Val | Gln | Leu | Gln | Gly | Leu | Thr | Tyr | Thr | Ala | Thr | Gly | Ile | Arg |
|  | 210 |  |  |  |  | 215 |  |  |  |  | 220 |  |  |  |  |
| Thr | Val | Met | Glu | Glu | Leu | Phe | His | Ser | Lys | Asn | Gly | Ser | Arg | Lys | Ser |
| 225 |  |  |  |  | 230 |  |  |  |  | 235 |  |  |  |  | 240 |
| Ala | Lys | Lys | Ile | Leu | Leu | Val | Ile | Thr | Asp | Gly | Gln | Lys | Tyr | Arg | Asp |
|  |  |  |  | 245 |  |  |  |  | 250 |  |  |  |  | 255 |  |
| Pro | Leu | Glu | Tyr | Ser | Asp | Val | Ile | Pro | Ala | Ala | Asp | Lys | Ala | Gly | Ile |
|  |  |  | 260 |  |  |  |  | 265 |  |  |  |  | 270 |  |  |
| Ile | Arg | Tyr | Ala | Ile | Gly | Val | Gly | Asp | Ala | Phe | Gln | Glu | Pro | Thr | Ala |
|  |  | 275 |  |  |  |  | 280 |  |  |  |  | 285 |  |  |  |

| | | | | | | | | | | | | | | |
|---|---|---|---|---|---|---|---|---|---|---|---|---|---|---|
| Leu | Lys 290 | Glu | Leu | Asn | Thr | Ile 295 | Gly | Ser | Ala | Pro | Pro 300 | Gln | Asp | His | Val |
| Phe 305 | Lys | Val | Gly | Asn | Phe 310 | Ala | Ala | Leu | Arg | Ser 315 | Ile | Gln | Arg | Gln | Leu 320 |
| Gln | Glu | Lys | Ile | Phe 325 | Ala | Ile | Glu | Gly | Thr 330 | Gln | Ser | Arg | Ser 335 | Ser | Ser |
| Ser | Phe | Gln | His 340 | Glu | Met | Ser | Gln | Glu 345 | Gly | Phe | Ser | Ser 350 | Ala | Leu | Thr |
| Ser | Asp | Gly 355 | Pro | Val | Leu | Gly | Ala 360 | Xaa | Gly | Ser | Phe | Ser 365 | Trp | Ser | Gly |
| Gly | Ala 370 | Phe | Leu | Tyr | Pro | Pro 375 | Asn | Thr | Arg | Pro | Thr 380 | Phe | Ile | Asn | Met |
| Ser 385 | Gln | Glu | Asn | Val | Asp 390 | Met | Arg | Asp | Ser | Tyr 395 | Leu | Gly | Tyr | Ser | Thr 400 |
| Ala | Val | Ala | Phe | Trp 405 | Lys | Gly | Val | His | Ser 410 | Leu | Ile | Leu | Gly 415 | Ala | Pro |
| Arg | His | Gln | His 420 | Thr | Gly | Lys | Val | Val 425 | Ile | Phe | Thr | Gln 430 | Glu | Ala | Arg |
| His | Trp | Arg 435 | Pro | Lys | Ser | Glu | Val 440 | Arg | Gly | Thr | Gln | Ile 445 | Gly | Ser | Tyr |
| Phe | Gly 450 | Ala | Ser | Leu | Cys | Ser 455 | Val | Asp | Val | Asp | Arg 460 | Asp | Gly | Ser | Xaa |
| Asp 465 | Leu | Val | Leu | Ile | Gly 470 | Ala | Pro | His | Tyr | Tyr 475 | Glu | Gln | Thr | Arg | Gly 480 |
| Gly | Gln | Val | Ser | Val 485 | Xaa | Pro | Val | Pro | Gly 490 | Val | Arg | Gly | Arg 495 | Trp | Gln |
| Cys | Glu | Ala | Thr 500 | Leu | His | Gly | Glu | Gln 505 | Xaa | His | Pro | Trp | Gly 510 | Arg | Phe |
| Gly | Val | Ala | Leu 515 | Thr | Val | Leu | Gly 520 | Asp | Val | Asn | Gly | Asp 525 | Asn | Leu | Ala |
| Asp | Val 530 | Ala | Ile | Gly | Ala | Pro 535 | Gly | Glu | Glu | Glu | Ser 540 | Arg | Gly | Ala | Val |
| Tyr 545 | Ile | Phe | His | Gly | Ala 550 | Ser | Arg | Leu | Glu | Ile 555 | Met | Pro | Ser | Pro | Ser 560 |
| Gln | Arg | Val | Thr | Gly 565 | Ser | Gln | Leu | Ser | Leu 570 | Arg | Leu | Gln | Tyr | Phe 575 | Gly |
| Gln | Ser | Leu | Ser 580 | Gly | Gly | Gln | Asp | Leu 585 | Thr | Gln | Asp | Gly | Leu 590 | Val | Asp |
| Leu | Ala | Val 595 | Gly | Ala | Gln | Gly | His 600 | Val | Leu | Leu | Leu | Arg 605 | Ser | Leu | Pro |
| Leu | Leu 610 | Lys | Val | Glu | Leu | Ser 615 | Ile | Arg | Phe | Ala | Pro 620 | Met | Glu | Val | Ala |
| Lys 625 | Ala | Val | Tyr | Gln | Cys 630 | Trp | Glu | Arg | Thr | Pro 635 | Thr | Val | Leu | Glu | Ala 640 |
| Gly | Glu | Ala | Thr | Val 645 | Cys | Leu | Thr | Val | His 650 | Lys | Gly | Ser | Pro | Asp 655 | Leu |
| Leu | Gly | Asn | Val 660 | Gln | Gly | Ser | Val | Arg 665 | Tyr | Asp | Leu | Ala | Leu 670 | Asp | Pro |
| Gly | Arg | Leu 675 | Ile | Ser | Arg | Ala | Ile 680 | Phe | Asp | Glu | Thr | Lys 685 | Asn | Cys | Thr |
| Leu | Thr 690 | Gly | Arg | Lys | Thr | Leu 695 | Gly | Leu | Gly | Asp | His 700 | Cys | Glu | Thr | Val |

-continued

| | | | | | | | | | | | | | | |
|---|---|---|---|---|---|---|---|---|---|---|---|---|---|---|
| Lys | Leu | Leu | Leu | Pro | Asp | Cys | Val | Glu | Asp | Ala | Val | Ser | Pro | Ile | Ile |
| 705 | | | | 710 | | | | | 715 | | | | | 720 |
| Leu | Arg | Leu | Asn | Phe | Ser | Leu | Val | Arg | Asp | Ser | Ala | Ser | Pro | Arg | Asn |
| | | | | 725 | | | | | 730 | | | | | 735 |
| Leu | His | Pro | Val | Leu | Ala | Val | Gly | Ser | Gln | Asp | His | Ile | Thr | Ala | Ser |
| | | | 740 | | | | | 745 | | | | | 750 | | |
| Leu | Pro | Phe | Glu | Lys | Asn | Cys | Lys | Gln | Glu | Leu | Leu | Cys | Glu | Gly | Asp |
| | | 755 | | | | | 760 | | | | | 765 | | | |
| Leu | Gly | Ile | Ser | Phe | Asn | Phe | Ser | Gly | Leu | Gln | Val | Leu | Val | Val | Gly |
| | 770 | | | | | 775 | | | | | 780 | | | | |
| Gly | Ser | Pro | Glu | Leu | Thr | Val | Thr | Val | Thr | Val | Trp | Asn | Glu | Gly | Glu |
| 785 | | | | | 790 | | | | | 795 | | | | | 800 |
| Asp | Ser | Tyr | Gly | Thr | Leu | Val | Lys | Phe | Tyr | Tyr | Pro | Ala | Gly | Leu | Ser |
| | | | | 805 | | | | | 810 | | | | | 815 | |
| Tyr | Arg | Arg | Val | Thr | Gly | Thr | Gln | Gln | Pro | His | Gln | Tyr | Pro | Leu | Arg |
| | | | 820 | | | | | 825 | | | | | 830 | | |
| Leu | Ala | Cys | Glu | Ala | Glu | Pro | Ala | Ala | Gln | Glu | Asp | Leu | Arg | Ser | Ser |
| | | 835 | | | | | 840 | | | | | 845 | | | |
| Ser | Cys | Ser | Ile | Asn | His | Pro | Ile | Phe | Arg | Glu | Gly | Ala | Lys | Thr | Thr |
| 850 | | | | | 855 | | | | | 860 | | | | | |
| Phe | Met | Ile | Thr | Phe | Asp | Val | Ser | Tyr | Lys | Ala | Phe | Leu | Gly | Asp | Arg |
| 865 | | | | | 870 | | | | 875 | | | | | | 880 |
| Leu | Leu | Leu | Arg | Ala | Lys | Ala | Ser | Ser | Glu | Asn | Asn | Lys | Pro | Asp | Thr |
| | | | | 885 | | | | | 890 | | | | | 895 | |
| Asn | Lys | Thr | Ala | Phe | Gln | Leu | Glu | Leu | Pro | Val | Lys | Tyr | Thr | Val | Tyr |
| | | | 900 | | | | | 905 | | | | | 910 | | |
| Thr | Leu | Ile | Ser | Arg | Gln | Glu | Asp | Ser | Thr | Asn | His | Val | Asn | Phe | Ser |
| | | 915 | | | | | 920 | | | | | 925 | | | |
| Ser | Ser | His | Gly | Gly | Arg | Arg | Gln | Glu | Ala | Ala | His | Arg | Tyr | Arg | Val |
| | | 930 | | | | 935 | | | | | 940 | | | | |
| Asn | Asn | Leu | Ser | Pro | Leu | Lys | Leu | Ala | Val | Arg | Val | Asn | Phe | Trp | Val |
| 945 | | | | | 950 | | | | | 955 | | | | | 960 |
| Pro | Val | Leu | Leu | Asn | Gly | Val | Ala | Val | Trp | Asp | Val | Thr | Leu | Ser | Ser |
| | | | | 965 | | | | | 970 | | | | | 975 | |
| Pro | Ala | Gln | Gly | Val | Ser | Cys | Val | Ser | Gln | Met | Lys | Pro | Pro | Gln | Asn |
| | | | 980 | | | | | 985 | | | | | 990 | | |
| Pro | Asp | Phe | Leu | Thr | Gln | Ile | Gln | Arg | Arg | Ser | Val | Leu | Asp | Cys | Ser |
| | | 995 | | | | | 1000 | | | | | 1005 | | | |
| Ile | Ala | Asp | Cys | Leu | His | Ser | Arg | Cys | Asp | Ile | Pro | Ser | Leu | Asp | Ile |
| | | 1010 | | | | 1015 | | | | | 1020 | | | | |
| Gln | Asp | Glu | Leu | Asp | Phe | Ile | Leu | Arg | Gly | Asn | Leu | Ser | Phe | Gly | Trp |
| 1025 | | | | | 1030 | | | | | 1035 | | | | | 1040 |
| Val | Ser | Gln | Thr | Leu | Gln | Glu | Lys | Val | Leu | Leu | Val | Ser | Glu | Ala | Glu |
| | | | | 1045 | | | | | 1050 | | | | | 1055 | |
| Ile | Thr | Phe | Asp | Thr | Ser | Val | Tyr | Ser | Gln | Leu | Pro | Gly | Gln | Glu | Ala |
| | | | 1060 | | | | | 1065 | | | | | 1070 | | |
| Phe | Leu | Arg | Ala | Gln | Val | Glu | Thr | Thr | Leu | Glu | Glu | Tyr | Val | Val | Tyr |
| | | 1075 | | | | | 1080 | | | | | 1085 | | | |
| Glu | Pro | Ile | Phe | Leu | Val | Ala | Gly | Ser | Ser | Val | Gly | Gly | Leu | Leu | Leu |
| | | 1090 | | | | 1095 | | | | | 1100 | | | | |
| Leu | Ala | Leu | Ile | Thr | Val | Val | Leu | Tyr | Lys | Leu | Gly | Xaa | Xaa | Lys | Arg |
| 1105 | | | | | 1110 | | | | | 1115 | | | | | 1120 |
| Gln | Tyr | Lys | Glu | Met | Leu | Asp | Gly | Lys | Ala | Ala | Asp | Pro | Val | Thr | Ala |

|  | 1125 |  |  |  |  | 1130 |  |  |  | 1135 |  |
|---|---|---|---|---|---|---|---|---|---|---|---|
| Gly | Gln | Ala | Asp | Phe | Gly | Cys | Glu | Thr | Pro | Pro | Tyr | Leu | Val | Ser |
|  |  |  |  | 1140 |  |  |  | 1145 |  |  |  | 1150 |  |  |

( 2 ) INFORMATION FOR SEQ ID NO:38:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:38:

GTCCAAGCTG TCATGGGCCA G                                          21

( 2 ) INFORMATION FOR SEQ ID NO:39:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:39:

GTCCAGCAGA CTGAAGAGCA CGG                                    23

( 2 ) INFORMATION FOR SEQ ID NO:40:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:40:

TGTAAAACGA CGGCCAGT                                                  18

( 2 ) INFORMATION FOR SEQ ID NO:41:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

GGAAACAGCT ATGACCATG                                               19

( 2 ) INFORMATION FOR SEQ ID NO:42:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

GGACATGTTC ACTGCCTCTA GG                                     22

( 2 ) INFORMATION FOR SEQ ID NO:43:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:43:

```
GGCGGACAGT CAGACGACTG TCCTG                                              25
```

( 2 ) INFORMATION FOR SEQ ID NO:44:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:44:

```
CTGGTTCGGC CCACCTCTGA AGGTTCCAGA ATCGATAG                                38
```

( 2 ) INFORMATION FOR SEQ ID NO:45:

( i ) SEQUENCE CHARACTERISTICS:
    ( A ) LENGTH: 3519 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 52..3519

( x i ) SEQUENCE DESCRIPTION: SEQ ID NO:45:

```
GCTTTCTGAA GGTTCCAGAA TCGATAGTGA ATTCGTGGGC ACTGCTCAGA T ATG GTC         57
                                                        Met Val
                                                          1

CGT GGA GTT GTG ATC CTC CTG TGT GGC TGG GCC CTG GCT TCC TGT CAT         105
Arg Gly Val Val Ile Leu Leu Cys Gly Trp Ala Leu Ala Ser Cys His
        5               10                  15

GGG TCT AAC CTG GAT GTG GAG AAG CCC GTC GTG TTC AAA GAG GAT GCA         153
Gly Ser Asn Leu Asp Val Glu Lys Pro Val Val Phe Lys Glu Asp Ala
     20              25                  30

GCC AGC TTC GGA CAG ACT GTG GTG CAG TTT GGT GGA TCT CGA CTC GTG         201
Ala Ser Phe Gly Gln Thr Val Val Gln Phe Gly Gly Ser Arg Leu Val
 35              40                  45                  50

GTG GGA GCC CCT CTG GAG GCG GTG GCA GTC AAC CAA ACA GGA CAG TCG         249
Val Gly Ala Pro Leu Glu Ala Val Ala Val Asn Gln Thr Gly Gln Ser
                 55                  60                  65

TCT GAC TGT CCG CCT GCC ACT GGC GTG TGC CAG CCC ATC TTA CTG CAC         297
Ser Asp Cys Pro Pro Ala Thr Gly Val Cys Gln Pro Ile Leu Leu His
             70                  75                  80

ATT CCC CTA GAG GCA GTG AAC ATG TCC CTG GGC CTG TCT CTG GTG GCT         345
Ile Pro Leu Glu Ala Val Asn Met Ser Leu Gly Leu Ser Leu Val Ala
             85                  90                  95

GAC ACC AAT AAC TCC CAG TTG CTG GCT TGT GGT CCA ACT GCA CAG AGA         393
Asp Thr Asn Asn Ser Gln Leu Leu Ala Cys Gly Pro Thr Ala Gln Arg
        100                 105                 110
```

```
GCT TGT GCA AAG AAC ATG TAT GCA AAA GGT TCC TGC CTC CTT CTG GGC          441
Ala Cys Ala Lys Asn Met Tyr Ala Lys Gly Ser Cys Leu Leu Leu Gly
115             120                 125                 130

TCC AGC TTG CAG TTC ATC CAG GCA ATC CCT GCT ACC ATG CCA GAG TGT          489
Ser Ser Leu Gln Phe Ile Gln Ala Ile Pro Ala Thr Met Pro Glu Cys
                135                 140                 145

CCA GGA CAA GAG ATG GAC ATT GCT TTC CTG ATT GAT GGC TCC GGC AGC          537
Pro Gly Gln Glu Met Asp Ile Ala Phe Leu Ile Asp Gly Ser Gly Ser
            150                 155                 160

ATT GAT CAA AGT GAC TTT ACC CAG ATG AAG GAC TTC GTC AAA GCT TTG          585
Ile Asp Gln Ser Asp Phe Thr Gln Met Lys Asp Phe Val Lys Ala Leu
        165                 170                 175

ATG GGC CAG TTG GCG AGC ACC AGC ACC TCG TTC TCC CTG ATG CAA TAC          633
Met Gly Gln Leu Ala Ser Thr Ser Thr Ser Phe Ser Leu Met Gln Tyr
    180                 185                 190

TCA AAC ATC CTG AAG ACT CAT TTT ACC TTC ACG GAA TTC AAG AGC AGC          681
Ser Asn Ile Leu Lys Thr His Phe Thr Phe Thr Glu Phe Lys Ser Ser
195             200                 205                 210

CTG AGC CCT CAG AGC CTG GTG GAT GCC ATC GTC CAG CTC CAA GGC CTG          729
Leu Ser Pro Gln Ser Leu Val Asp Ala Ile Val Gln Leu Gln Gly Leu
                215                 220                 225

ACG TAC ACA GCC TCG GGC ATC CAG AAA GTG GTG AAA GAG CTA TTT CAT          777
Thr Tyr Thr Ala Ser Gly Ile Gln Lys Val Val Lys Glu Leu Phe His
            230                 235                 240

AGC AAG AAT GGG GCC CGA AAA AGT GCC AAG AAG ATA CTA ATT GTC ATC          825
Ser Lys Asn Gly Ala Arg Lys Ser Ala Lys Lys Ile Leu Ile Val Ile
        245                 250                 255

ACA GAT GGG CAG AAA TTC AGA GAC CCC CTG GAG TAT AGA CAT GTC ATC          873
Thr Asp Gly Gln Lys Phe Arg Asp Pro Leu Glu Tyr Arg His Val Ile
260             265                 270

CCT GAA GCA GAG AAA GCT GGG ATC ATT CGC TAT GCT ATA GGG GTG GGA          921
Pro Glu Ala Glu Lys Ala Gly Ile Ile Arg Tyr Ala Ile Gly Val Gly
275                 280                 285                 290

GAT GCC TTC CGG GAA CCC ACT GCC CTA CAG GAG CTG AAC ACC ATT GGC          969
Asp Ala Phe Arg Glu Pro Thr Ala Leu Gln Glu Leu Asn Thr Ile Gly
            295                 300                 305

TCA GCT CCC TCG CAG GAC CAC GTG TTC AAG GTG GGC AAT TTT GTA GCA         1017
Ser Ala Pro Ser Gln Asp His Val Phe Lys Val Gly Asn Phe Val Ala
        310                 315                 320

CTT CGC AGC ATC CAG CGG CAA ATT CAG GAG AAA ATC TTT GCC ATT GAA         1065
Leu Arg Ser Ile Gln Arg Gln Ile Gln Glu Lys Ile Phe Ala Ile Glu
        325                 330                 335

GGA ACC GAA TCA AGG TCA AGT AGT TCC TTT CAG CAC GAG ATG TCA CAA         1113
Gly Thr Glu Ser Arg Ser Ser Ser Phe Gln His Glu Met Ser Gln
340                 345                 350

GAA GGT TTC AGC TCA GCT CTC TCA ATG GAT GGA CCA GTT CTG GGG GCT         1161
Glu Gly Phe Ser Ser Ala Leu Ser Met Asp Gly Pro Val Leu Gly Ala
355                 360                 365                 370

GTG GGA GGC TTC AGC TGG TCT GGA GGT GCC TTC TTG TAC CCC TCA AAT         1209
Val Gly Gly Phe Ser Trp Ser Gly Gly Ala Phe Leu Tyr Pro Ser Asn
            375                 380                 385

ATG AGA TCC ACC TTC ATC AAC ATG TCT CAG GAG AAC GAG GAT ATG AGG         1257
Met Arg Ser Thr Phe Ile Asn Met Ser Gln Glu Asn Glu Asp Met Arg
            390                 395                 400

GAC GCT TAC CTG GGT TAC TCC ACC GCA CTG GCC TTT TGG AAG GGG GTC         1305
Asp Ala Tyr Leu Gly Tyr Ser Thr Ala Leu Ala Phe Trp Lys Gly Val
            405                 410                 415

CAC AGC CTG ATC CTG GGG GCC CCT CGC CAC CAG CAC ACG GGG AAG GTT         1353
His Ser Leu Ile Leu Gly Ala Pro Arg His Gln His Thr Gly Lys Val
```

|  |  |  |  |  |  |  |  |  |  |  |  |  |  |  |  |
|---|---|---|---|---|---|---|---|---|---|---|---|---|---|---|---|
| | 420 | | | | | 425 | | | | | 430 | | | | |
| GTC | ATC | TTT | ACC | CAG | GAA | TCC | AGG | CAC | TGG | AGG | CCC | AAG | TCT | GAA | GTC |
| Val | Ile | Phe | Thr | Gln | Glu | Ser | Arg | His | Trp | Arg | Pro | Lys | Ser | Glu | Val |
| 435 | | | | 440 | | | | | 445 | | | | | 450 | |

1401

| AGA | GGG | ACA | CAG | ATC | GGC | TCC | TAC | TTT | GGG | GCA | TCT | CTC | TGT | TCT | GTG |
|---|---|---|---|---|---|---|---|---|---|---|---|---|---|---|---|
| Arg | Gly | Thr | Gln | Ile | Gly | Ser | Tyr | Phe | Gly | Ala | Ser | Leu | Cys | Ser | Val |
| | | | | 455 | | | | | 460 | | | | | 465 | |

1449

| GAC | ATG | GAT | AGA | GAT | GGC | AGC | ACT | GAC | CTG | GTC | CTG | ATT | GGA | GTC | CCC |
|---|---|---|---|---|---|---|---|---|---|---|---|---|---|---|---|
| Asp | Met | Asp | Arg | Asp | Gly | Ser | Thr | Asp | Leu | Val | Leu | Ile | Gly | Val | Pro |
| | | | 470 | | | | | 475 | | | | | 480 | | |

1497

| CAT | TAC | TAT | GAG | CAC | ACC | CGA | GGG | GGG | CAG | GTG | TCG | GTG | TGC | CCC | ATG |
|---|---|---|---|---|---|---|---|---|---|---|---|---|---|---|---|
| His | Tyr | Tyr | Glu | His | Thr | Arg | Gly | Gly | Gln | Val | Ser | Val | Cys | Pro | Met |
| | | 485 | | | | | 490 | | | | | 495 | | | |

1545

| CCT | GGT | GTG | AGG | AGC | AGG | TGG | CAT | TGT | GGG | ACC | ACC | CTC | CAT | GGG | GAG |
|---|---|---|---|---|---|---|---|---|---|---|---|---|---|---|---|
| Pro | Gly | Val | Arg | Ser | Arg | Trp | His | Cys | Gly | Thr | Thr | Leu | His | Gly | Glu |
| | 500 | | | | | 505 | | | | | 510 | | | | |

1593

| CAG | GGC | CAT | CCT | TGG | GGC | CGC | TTT | GGG | GCG | GCT | CTG | ACA | GTG | CTA | GGG |
|---|---|---|---|---|---|---|---|---|---|---|---|---|---|---|---|
| Gln | Gly | His | Pro | Trp | Gly | Arg | Phe | Gly | Ala | Ala | Leu | Thr | Val | Leu | Gly |
| 515 | | | | | 520 | | | | | 525 | | | | | 530 |

1641

| GAC | GTG | AAT | GGG | GAC | AGT | CTG | GCG | GAT | GTG | GCT | ATT | GGT | GCA | CCC | GGA |
|---|---|---|---|---|---|---|---|---|---|---|---|---|---|---|---|
| Asp | Val | Asn | Gly | Asp | Ser | Leu | Ala | Asp | Val | Ala | Ile | Gly | Ala | Pro | Gly |
| | | | 535 | | | | | 540 | | | | | 545 | | |

1689

| GAG | GAG | GAG | AAC | AGA | GGT | GCT | GTC | TAC | ATA | TTT | CAT | GGA | GCC | TCG | AGA |
|---|---|---|---|---|---|---|---|---|---|---|---|---|---|---|---|
| Glu | Glu | Glu | Asn | Arg | Gly | Ala | Val | Tyr | Ile | Phe | His | Gly | Ala | Ser | Arg |
| | | | 550 | | | | | 555 | | | | | 560 | | |

1737

| CAG | GAC | ATC | GCT | CCC | TCG | CCT | AGC | CAG | CGG | GTC | ACT | GGC | TCC | CAG | CTC |
|---|---|---|---|---|---|---|---|---|---|---|---|---|---|---|---|
| Gln | Asp | Ile | Ala | Pro | Ser | Pro | Ser | Gln | Arg | Val | Thr | Gly | Ser | Gln | Leu |
| | | 565 | | | | | 570 | | | | | 575 | | | |

1785

| TTC | CTG | AGG | CTC | CAA | TAT | TTT | GGG | CAG | TCA | TTA | AGT | GGG | GGT | CAG | GAC |
|---|---|---|---|---|---|---|---|---|---|---|---|---|---|---|---|
| Phe | Leu | Arg | Leu | Gln | Tyr | Phe | Gly | Gln | Ser | Leu | Ser | Gly | Gly | Gln | Asp |
| | 580 | | | | | 585 | | | | | 590 | | | | |

1833

| CTT | ACA | CAG | GAT | GGC | CTG | GTG | GAC | CTG | GCC | GTG | GGA | GCC | CAG | GGG | CAC |
|---|---|---|---|---|---|---|---|---|---|---|---|---|---|---|---|
| Leu | Thr | Gln | Asp | Gly | Leu | Val | Asp | Leu | Ala | Val | Gly | Ala | Gln | Gly | His |
| 595 | | | | 600 | | | | | 605 | | | | | 610 | |

1881

| GTG | CTG | CTG | CTT | AGG | AGT | CTG | CCT | TTG | CTG | AAA | GTG | GGG | ATC | TCC | ATT |
|---|---|---|---|---|---|---|---|---|---|---|---|---|---|---|---|
| Val | Leu | Leu | Leu | Arg | Ser | Leu | Pro | Leu | Leu | Lys | Val | Gly | Ile | Ser | Ile |
| | | | | 615 | | | | | 620 | | | | | 625 | |

1929

| AGA | TTT | GCC | CCC | TCA | GAG | GTG | GCA | AAG | ACT | GTG | TAC | CAG | TGC | TGG | GGA |
|---|---|---|---|---|---|---|---|---|---|---|---|---|---|---|---|
| Arg | Phe | Ala | Pro | Ser | Glu | Val | Ala | Lys | Thr | Val | Tyr | Gln | Cys | Trp | Gly |
| | | | 630 | | | | | 635 | | | | | 640 | | |

1977

| AGG | ACT | CCC | ACT | GTC | CTC | GAA | GCT | GGA | GAG | GCC | ACC | GTC | TGT | CTC | ACT |
|---|---|---|---|---|---|---|---|---|---|---|---|---|---|---|---|
| Arg | Thr | Pro | Thr | Val | Leu | Glu | Ala | Gly | Glu | Ala | Thr | Val | Cys | Leu | Thr |
| | | 645 | | | | | 650 | | | | | 655 | | | |

2025

| GTC | CGC | AAA | GGT | TCA | CCT | GAC | CTG | TTA | GGT | GAT | GTC | CAA | AGC | TCT | GTC |
|---|---|---|---|---|---|---|---|---|---|---|---|---|---|---|---|
| Val | Arg | Lys | Gly | Ser | Pro | Asp | Leu | Leu | Gly | Asp | Val | Gln | Ser | Ser | Val |
| | 660 | | | | | 665 | | | | | 670 | | | | |

2073

| AGG | TAT | GAT | CTG | GCG | TTG | GAT | CCG | GGC | CGT | CTG | ATT | TCT | CGT | GCC | ATT |
|---|---|---|---|---|---|---|---|---|---|---|---|---|---|---|---|
| Arg | Tyr | Asp | Leu | Ala | Leu | Asp | Pro | Gly | Arg | Leu | Ile | Ser | Arg | Ala | Ile |
| 675 | | | | | 680 | | | | | 685 | | | | | 690 |

2121

| TTT | GAT | GAG | ACG | AAG | AAC | TGC | ACT | TTG | ACC | CGA | AGG | AAG | ACT | CTG | GGG |
|---|---|---|---|---|---|---|---|---|---|---|---|---|---|---|---|
| Phe | Asp | Glu | Thr | Lys | Asn | Cys | Thr | Leu | Thr | Arg | Arg | Lys | Thr | Leu | Gly |
| | | | | 695 | | | | | 700 | | | | | 705 | |

2169

| CTT | GGT | GAT | CAC | TGC | GAA | ACA | ATG | AAG | CTG | CTT | TTG | CCA | GAC | TGT | GTG |
|---|---|---|---|---|---|---|---|---|---|---|---|---|---|---|---|
| Leu | Gly | Asp | His | Cys | Glu | Thr | Met | Lys | Leu | Leu | Leu | Pro | Asp | Cys | Val |
| | | | 710 | | | | | 715 | | | | | 720 | | |

2217

| GAG | GAT | GCA | GTG | ACC | CCT | ATC | ATC | CTG | CGC | CTT | AAC | TTA | TCC | CTG | GCA |
|---|---|---|---|---|---|---|---|---|---|---|---|---|---|---|---|
| Glu | Asp | Ala | Val | Thr | Pro | Ile | Ile | Leu | Arg | Leu | Asn | Leu | Ser | Leu | Ala |
| | | 725 | | | | | 730 | | | | | 735 | | | |

2265

| GGG | GAC | TCT | GCT | CCA | TCC | AGG | AAC | CTT | CGT | CCT | GTG | CTG | GCT | GTG | GGC |
|---|---|---|---|---|---|---|---|---|---|---|---|---|---|---|---|

2313

```
            Gly  Asp  Ser  Ala  Pro  Ser  Arg  Asn  Leu  Arg  Pro  Val  Leu  Ala  Val  Gly
                 740                 745                 750

TCA  CAA  GAC  CAT  GTA  ACA  GCT  TCT  TTC  CCG  TTT  GAG  AAG  AAC  TGT  GAG        2361
            Ser  Gln  Asp  His  Val  Thr  Ala  Ser  Phe  Pro  Phe  Glu  Lys  Asn  Cys  Glu
            755                 760                 765                 770

GGG  AAC  CTG  GGC  GTC  AGC  TTC  AAC  TTC  TCA  GGC  CTG  CAG  GTC  TTG  GAG        2409
            Gly  Asn  Leu  Gly  Val  Ser  Phe  Asn  Phe  Ser  Gly  Leu  Gln  Val  Leu  Glu
                                775                 780                 785

GTA  GGA  AGC  TCC  CCA  GAG  CTC  ACT  GTG  ACA  GTA  ACA  GTT  TGG  AAT  GAG        2457
            Val  Gly  Ser  Ser  Pro  Glu  Leu  Thr  Val  Thr  Val  Thr  Val  Trp  Asn  Glu
                                790                 795                 800

GGT  GAG  GAC  AGC  TAT  GGA  ACC  TTA  ATC  AAG  TTC  TAC  TAC  CCA  GCA  GAG        2505
            Gly  Glu  Asp  Ser  Tyr  Gly  Thr  Leu  Ile  Lys  Phe  Tyr  Tyr  Pro  Ala  Glu
                      805                 810                 815

CTA  TCT  TAC  CGA  CGG  GTG  ACA  AGA  GCC  CAG  CAA  CCT  CAT  CCG  TAC  CCA        2553
            Leu  Ser  Tyr  Arg  Arg  Val  Thr  Arg  Ala  Gln  Gln  Pro  His  Pro  Tyr  Pro
            820                 825                 830

CTA  CGC  CTG  GCA  TGT  GAG  GCT  GAG  CCC  ACG  GGC  CAG  GAG  AGC  CTG  AGG        2601
            Leu  Arg  Leu  Ala  Cys  Glu  Ala  Glu  Pro  Thr  Gly  Gln  Glu  Ser  Leu  Arg
            835                 840                 845                 850

AGC  AGC  AGC  TGT  AGC  ATC  AAT  CAC  CCC  ATC  TTC  CGA  GAA  GGT  GCC  AAG        2649
            Ser  Ser  Ser  Cys  Ser  Ile  Asn  His  Pro  Ile  Phe  Arg  Glu  Gly  Ala  Lys
                                855                 860                 865

GCC  ACC  TTC  ATG  ATC  ACA  TTT  GAT  GTC  TCC  TAC  AAG  GCC  TTC  CTG  GGA        2697
            Ala  Thr  Phe  Met  Ile  Thr  Phe  Asp  Val  Ser  Tyr  Lys  Ala  Phe  Leu  Gly
                           870                 875                 880

GAC  AGG  TTG  CTT  CTG  AGG  GCC  AGC  GCA  AGC  AGT  GAG  AAT  AAT  AAG  CCT        2745
            Asp  Arg  Leu  Leu  Leu  Arg  Ala  Ser  Ala  Ser  Ser  Glu  Asn  Asn  Lys  Pro
                           885                 890                 895

GAA  ACC  AGC  AAG  ACT  GCC  TTC  CAG  CTG  GAG  CTT  CCG  GTG  AAG  TAC  ACG        2793
            Glu  Thr  Ser  Lys  Thr  Ala  Phe  Gln  Leu  Glu  Leu  Pro  Val  Lys  Tyr  Thr
                 900                 905                 910

GTC  TAT  ACC  GTG  ATC  AGT  AGG  CAG  GAA  GAT  TCT  ACC  AAG  CAT  TTC  AAC        2841
            Val  Tyr  Thr  Val  Ile  Ser  Arg  Gln  Glu  Asp  Ser  Thr  Lys  His  Phe  Asn
            915                 920                 925                 930

TTC  TCA  TCT  TCC  CAC  GGG  GAG  AGA  CAG  AAA  GAG  GCC  GAA  CAT  CGA  TAT        2889
            Phe  Ser  Ser  Ser  His  Gly  Glu  Arg  Gln  Lys  Glu  Ala  Glu  His  Arg  Tyr
                                935                 940                 945

CGT  GTG  AAT  AAC  CTG  AGT  CCA  TTG  ACG  CTG  GCC  ATC  AGC  GTT  AAC  TTC        2937
            Arg  Val  Asn  Asn  Leu  Ser  Pro  Leu  Thr  Leu  Ala  Ile  Ser  Val  Asn  Phe
                           950                 955                 960

TGG  GTC  CCC  ATC  CTT  CTG  AAT  GGT  GTG  GCC  GTG  TGG  GAT  GTG  ACT  CTG        2985
            Trp  Val  Pro  Ile  Leu  Leu  Asn  Gly  Val  Ala  Val  Trp  Asp  Val  Thr  Leu
                      965                 970                 975

AGG  AGC  CCA  GCA  CAG  GGT  GTC  TCC  TGT  GTG  TCA  CAG  AGG  GAA  CCT  CCT        3033
            Arg  Ser  Pro  Ala  Gln  Gly  Val  Ser  Cys  Val  Ser  Gln  Arg  Glu  Pro  Pro
                 980                 985                 990

CAA  CAT  TCC  GAC  CTT  CTG  ACC  CAG  ATC  CAA  GGA  CGC  TCT  GTG  CTG  GAC        3081
            Gln  His  Ser  Asp  Leu  Leu  Thr  Gln  Ile  Gln  Gly  Arg  Ser  Val  Leu  Asp
            995                 1000                1005                1010

TGC  GCC  ATC  GCC  GAC  TGC  CTG  CAC  CTC  CGC  TGT  GAC  ATC  CCC  TCC  TTG        3129
            Cys  Ala  Ile  Ala  Asp  Cys  Leu  His  Leu  Arg  Cys  Asp  Ile  Pro  Ser  Leu
                                1015                1020                1025

GGC  ACC  CTG  GAT  GAG  CTT  GAC  TTC  ATT  CTG  AAG  GGC  AAC  CTC  AGC  TTC        3177
            Gly  Thr  Leu  Asp  Glu  Leu  Asp  Phe  Ile  Leu  Lys  Gly  Asn  Leu  Ser  Phe
                           1030                1035                1040

GGC  TGG  ATC  AGT  CAG  ACA  TTG  CAG  AAA  AAG  GTG  TTG  CTC  CTG  AGT  GAG        3225
            Gly  Trp  Ile  Ser  Gln  Thr  Leu  Gln  Lys  Lys  Val  Leu  Leu  Leu  Ser  Glu
                      1045                1050                1055
```

| | | | | | | | | | | | | | | | | |
|---|---|---|---|---|---|---|---|---|---|---|---|---|---|---|---|---|
| GCT | GAA | ATC | ACA | TTC | AAC | ACA | TCT | GTG | TAT | TCC | CAG | CTG | CCG | GGA | CAG | 3273 |
| Ala | Glu | Ile | Thr | Phe | Asn | Thr | Ser | Val | Tyr | Ser | Gln | Leu | Pro | Gly | Gln | |
| | 1060 | | | | 1065 | | | | | 1070 | | | | | | |
| GAG | GCA | TTT | CTG | AGA | GCC | CAG | GTG | TCA | ACG | ATG | CTA | GAA | GAA | TAC | GTG | 3321 |
| Glu | Ala | Phe | Leu | Arg | Ala | Gln | Val | Ser | Thr | Met | Leu | Glu | Glu | Tyr | Val | |
| 1075 | | | | | 1080 | | | | | 1085 | | | | | 1090 | |
| GTC | TAT | GAG | CCC | GTC | TTC | CTC | ATG | GTG | TTC | AGC | TCA | GTG | GGA | GGT | CTG | 3369 |
| Val | Tyr | Glu | Pro | Val | Phe | Leu | Met | Val | Phe | Ser | Ser | Val | Gly | Gly | Leu | |
| | | | | 1095 | | | | 1100 | | | | | 1105 | | | |
| CTG | TTA | CTG | GCT | CTC | ATC | ACT | GTG | GCG | CTG | TAC | AAG | CTT | GGC | TTC | TTC | 3417 |
| Leu | Leu | Leu | Ala | Leu | Ile | Thr | Val | Ala | Leu | Tyr | Lys | Leu | Gly | Phe | Phe | |
| | | | 1110 | | | | | 1115 | | | | | 1120 | | | |
| AAA | CGT | CAG | TAT | AAA | GAG | ATG | CTG | GAT | CTA | CCA | TCT | GCA | GAT | CCT | GAC | 3465 |
| Lys | Arg | Gln | Tyr | Lys | Glu | Met | Leu | Asp | Leu | Pro | Ser | Ala | Asp | Pro | Asp | |
| | | 1125 | | | | | 1130 | | | | | 1135 | | | | |
| CCA | GCC | GGC | CAG | GCA | GAT | TCC | AAC | CAT | GAG | ACT | CCT | CCA | CAT | CTC | ACG | 3513 |
| Pro | Ala | Gly | Gln | Ala | Asp | Ser | Asn | His | Glu | Thr | Pro | Pro | His | Leu | Thr | |
| | 1140 | | | | | 1145 | | | | | 1150 | | | | | |
| TCC | TAG | | | | | | | | | | | | | | | 3519 |
| Ser | | | | | | | | | | | | | | | | |
| 1155 | | | | | | | | | | | | | | | | |

(2) INFORMATION FOR SEQ ID NO:46:

(i) SEQUENCE CHARACTERISTICS:
        (A) LENGTH: 1155 amino acids
        (B) TYPE: amino acid
        (D) TOPOLOGY: linear (ii) MOLECULE TYPE: protein (xi) SEQUENCE DESCRIPTION: SEQ ID NO:46:

| | | | | | | | | | | | | | | |
|---|---|---|---|---|---|---|---|---|---|---|---|---|---|---|
| Met | Val | Arg | Gly | Val | Val | Ile | Leu | Leu | Cys | Gly | Trp | Ala | Leu | Ala | Ser |
| 1 | | | | 5 | | | | | 10 | | | | | 15 | |
| Cys | His | Gly | Ser | Asn | Leu | Asp | Val | Glu | Lys | Pro | Val | Val | Phe | Lys | Glu |
| | | | 20 | | | | | 25 | | | | | 30 | | |
| Asp | Ala | Ala | Ser | Phe | Gly | Gln | Thr | Val | Val | Gln | Phe | Gly | Gly | Ser | Arg |
| | | 35 | | | | | 40 | | | | | 45 | | | |
| Leu | Val | Val | Gly | Ala | Pro | Leu | Glu | Ala | Val | Ala | Val | Asn | Gln | Thr | Gly |
| | 50 | | | | | 55 | | | | | 60 | | | | |
| Gln | Ser | Ser | Asp | Cys | Pro | Pro | Ala | Thr | Gly | Val | Cys | Gln | Pro | Ile | Leu |
| 65 | | | | | 70 | | | | | 75 | | | | | 80 |
| Leu | His | Ile | Pro | Leu | Glu | Ala | Val | Asn | Met | Ser | Leu | Gly | Leu | Ser | Leu |
| | | | | 85 | | | | | 90 | | | | | 95 | |
| Val | Ala | Asp | Thr | Asn | Asn | Ser | Gln | Leu | Leu | Ala | Cys | Gly | Pro | Thr | Ala |
| | | | 100 | | | | | 105 | | | | | 110 | | |
| Gln | Arg | Ala | Cys | Ala | Lys | Asn | Met | Tyr | Ala | Lys | Gly | Ser | Cys | Leu | Leu |
| | | 115 | | | | | 120 | | | | | 125 | | | |
| Leu | Gly | Ser | Ser | Leu | Gln | Phe | Ile | Gln | Ala | Ile | Pro | Ala | Thr | Met | Pro |
| | 130 | | | | | 135 | | | | | 140 | | | | |
| Glu | Cys | Pro | Gly | Gln | Glu | Met | Asp | Ile | Ala | Phe | Leu | Ile | Asp | Gly | Ser |
| 145 | | | | | 150 | | | | | 155 | | | | | 160 |
| Gly | Ser | Ile | Asp | Gln | Ser | Asp | Phe | Thr | Gln | Met | Lys | Asp | Phe | Val | Lys |
| | | | | 165 | | | | | 170 | | | | | 175 | |
| Ala | Leu | Met | Gly | Gln | Leu | Ala | Ser | Thr | Ser | Thr | Ser | Phe | Ser | Leu | Met |
| | | | 180 | | | | | 185 | | | | | 190 | | |
| Gln | Tyr | Ser | Asn | Ile | Leu | Lys | Thr | His | Phe | Thr | Phe | Thr | Glu | Phe | Lys |
| | | | | 195 | | | | | 200 | | | | | 205 | |

| | | | | | | | | | | | | | | |
|---|---|---|---|---|---|---|---|---|---|---|---|---|---|---|
|Ser|Ser|Leu|Ser|Pro|Gln|Ser|Leu|Val|Asp|Ala|Ile|Val|Gln|Leu|Gln|
| |210| | | |215| | | |220| | | | | |
|Gly|Leu|Thr|Tyr|Thr|Ala|Ser|Gly|Ile|Gln|Lys|Val|Val|Lys|Glu|Leu|
| |225| | | |230| | | |235| | | | | |240|
|Phe|His|Ser|Lys|Asn|Gly|Ala|Arg|Lys|Ser|Ala|Lys|Lys|Ile|Leu|Ile|
| | | | |245| | | |250| | | | |255| | |
|Val|Ile|Thr|Asp|Gly|Gln|Lys|Phe|Arg|Asp|Pro|Leu|Glu|Tyr|Arg|His|
| | | |260| | | | |265| | | | |270| | |
|Val|Ile|Pro|Glu|Ala|Glu|Lys|Ala|Gly|Ile|Ile|Arg|Tyr|Ala|Ile|Gly|
| | |275| | | | |280| | | | |285| | | |
|Val|Gly|Asp|Ala|Phe|Arg|Glu|Pro|Thr|Ala|Leu|Gln|Glu|Leu|Asn|Thr|
| |290| | | | |295| | | |300| | | | | |
|Ile|Gly|Ser|Ala|Pro|Ser|Gln|Asp|His|Val|Phe|Lys|Val|Gly|Asn|Phe|
|305| | | | |310| | | |315| | | | | |320|
|Val|Ala|Leu|Arg|Ser|Ile|Gln|Arg|Gln|Ile|Gln|Glu|Lys|Ile|Phe|Ala|
| | | | |325| | | |330| | | | |335| | |
|Ile|Glu|Gly|Thr|Glu|Ser|Arg|Ser|Ser|Ser|Phe|Gln|His|Glu|Met|
| | | |340| | | |345| | | | |350| | | |
|Ser|Gln|Glu|Gly|Phe|Ser|Ser|Ala|Leu|Ser|Met|Asp|Gly|Pro|Val|Leu|
| | |355| | | | |360| | | | |365| | | |
|Gly|Ala|Val|Gly|Gly|Phe|Ser|Trp|Ser|Gly|Gly|Ala|Phe|Leu|Tyr|Pro|
| |370| | | | |375| | | | |380| | | | |
|Ser|Asn|Met|Arg|Ser|Thr|Phe|Ile|Asn|Met|Ser|Gln|Glu|Asn|Glu|Asp|
|385| | | | |390| | | | |395| | | | |400|
|Met|Arg|Asp|Ala|Tyr|Leu|Gly|Tyr|Ser|Thr|Ala|Leu|Ala|Phe|Trp|Lys|
| | | | |405| | | | |410| | | | |415| |
|Gly|Val|His|Ser|Leu|Ile|Leu|Gly|Ala|Pro|Arg|His|Gln|His|Thr|Gly|
| | | |420| | | | |425| | | | |430| | |
|Lys|Val|Val|Ile|Phe|Thr|Gln|Glu|Ser|Arg|His|Trp|Arg|Pro|Lys|Ser|
| | |435| | | | |440| | | | |445| | | |
|Glu|Val|Arg|Gly|Thr|Gln|Ile|Gly|Ser|Tyr|Phe|Gly|Ala|Ser|Leu|Cys|
| |450| | | | |455| | | | |460| | | | |
|Ser|Val|Asp|Met|Asp|Arg|Asp|Gly|Ser|Thr|Asp|Leu|Val|Leu|Ile|Gly|
|465| | | | |470| | | | |475| | | | |480|
|Val|Pro|His|Tyr|Tyr|Glu|His|Thr|Arg|Gly|Gly|Gln|Val|Ser|Val|Cys|
| | | | |485| | | | |490| | | | |495| |
|Pro|Met|Pro|Gly|Val|Arg|Ser|Arg|Trp|His|Cys|Gly|Thr|Thr|Leu|His|
| | | |500| | | | |505| | | | |510| | |
|Gly|Glu|Gln|Gly|His|Pro|Trp|Gly|Arg|Phe|Gly|Ala|Ala|Leu|Thr|Val|
| | |515| | | | |520| | | | |525| | | |
|Leu|Gly|Asp|Val|Asn|Gly|Asp|Ser|Leu|Ala|Asp|Val|Ala|Ile|Gly|Ala|
| |530| | | | |535| | | | |540| | | | |
|Pro|Gly|Glu|Glu|Glu|Asn|Arg|Gly|Ala|Val|Tyr|Ile|Phe|His|Gly|Ala|
|545| | | | |550| | | | |555| | | | |560|
|Ser|Arg|Gln|Asp|Ile|Ala|Pro|Ser|Pro|Ser|Gln|Arg|Val|Thr|Gly|Ser|
| | | | |565| | | |570| | | | |575| | |
|Gln|Leu|Phe|Leu|Arg|Leu|Gln|Tyr|Phe|Gly|Gln|Ser|Leu|Ser|Gly|Gly|
| | | |580| | | | |585| | | | |590| | |
|Gln|Asp|Leu|Thr|Gln|Asp|Gly|Leu|Val|Asp|Leu|Ala|Val|Gly|Ala|Gln|
| | |595| | | | |600| | | | |605| | | |
|Gly|His|Val|Leu|Leu|Leu|Arg|Ser|Leu|Pro|Leu|Leu|Lys|Val|Gly|Ile|
| |610| | | | |615| | | | |620| | | | |
|Ser|Ile|Arg|Phe|Ala|Pro|Ser|Glu|Val|Ala|Lys|Thr|Val|Tyr|Gln|Cys|

|     |     |     |     |     |     |     |     |     |     |     |     |     |     |     |
| --- | --- | --- | --- | --- | --- | --- | --- | --- | --- | --- | --- | --- | --- | --- |
| 625 |     |     |     |     | 630 |     |     |     |     | 635 |     |     |     | 640 |
| Trp | Gly | Arg | Thr | Pro<br>645 | Thr | Val | Leu | Glu | Ala<br>650 | Gly | Glu | Ala | Thr | Val<br>655 | Cys |
| Leu | Thr | Val | Arg | Lys<br>660 | Gly | Ser | Pro | Asp<br>665 | Leu | Leu | Gly | Asp | Val<br>670 | Gln | Ser |
| Ser | Val | Arg | Tyr<br>675 | Asp | Leu | Ala | Leu<br>680 | Asp | Pro | Gly | Arg | Leu<br>685 | Ile | Ser | Arg |
| Ala | Ile<br>690 | Phe | Asp | Glu | Thr | Lys<br>695 | Asn | Cys | Thr | Leu | Thr<br>700 | Arg | Arg | Lys | Thr |
| Leu<br>705 | Gly | Leu | Gly | Asp | His<br>710 | Cys | Glu | Thr | Met | Lys<br>715 | Leu | Leu | Leu | Pro | Asp<br>720 |
| Cys | Val | Glu | Asp | Ala<br>725 | Val | Thr | Pro | Ile | Ile<br>730 | Leu | Arg | Leu | Asn | Leu<br>735 | Ser |
| Leu | Ala | Gly | Asp<br>740 | Ser | Ala | Pro | Ser | Arg<br>745 | Asn | Leu | Arg | Pro | Val<br>750 | Leu | Ala |
| Val | Gly | Ser<br>755 | Gln | Asp | His | Val | Thr<br>760 | Ala | Ser | Phe | Pro | Phe<br>765 | Glu | Lys | Asn |
| Cys | Glu<br>770 | Gly | Asn | Leu | Gly | Val<br>775 | Ser | Phe | Asn | Phe | Ser<br>780 | Gly | Leu | Gln | Val |
| Leu<br>785 | Glu | Val | Gly | Ser | Ser<br>790 | Pro | Glu | Leu | Thr | Val<br>795 | Thr | Val | Thr | Val | Trp<br>800 |
| Asn | Glu | Gly | Glu | Asp<br>805 | Ser | Tyr | Gly | Thr | Leu<br>810 | Ile | Lys | Phe | Tyr | Tyr<br>815 | Pro |
| Ala | Glu | Leu | Ser<br>820 | Tyr | Arg | Arg | Val | Thr<br>825 | Arg | Ala | Gln | Gln | Pro<br>830 | His | Pro |
| Tyr | Pro | Leu | Arg<br>835 | Leu | Ala | Cys | Glu | Ala<br>840 | Glu | Pro | Thr | Gly | Gln<br>845 | Glu | Ser |
| Leu | Arg<br>850 | Ser | Ser | Ser | Cys | Ser<br>855 | Ile | Asn | His | Pro | Ile<br>860 | Phe | Arg | Glu | Gly |
| Ala<br>865 | Lys | Ala | Thr | Phe | Met<br>870 | Ile | Thr | Phe | Asp | Val<br>875 | Ser | Tyr | Lys | Ala | Phe<br>880 |
| Leu | Gly | Asp | Arg | Leu<br>885 | Leu | Leu | Arg | Ala | Ser<br>890 | Ala | Ser | Ser | Glu | Asn<br>895 | Asn |
| Lys | Pro | Glu | Thr<br>900 | Ser | Lys | Thr | Ala | Phe<br>905 | Gln | Leu | Glu | Leu | Pro<br>910 | Val | Lys |
| Tyr | Thr | Val<br>915 | Tyr | Thr | Val | Ile | Ser<br>920 | Arg | Gln | Glu | Asp | Ser<br>925 | Thr | Lys | His |
| Phe | Asn<br>930 | Phe | Ser | Ser | Ser | His<br>935 | Gly | Glu | Arg | Gln | Lys<br>940 | Glu | Ala | Glu | His |
| Arg<br>945 | Tyr | Arg | Val | Asn | Asn<br>950 | Leu | Ser | Pro | Leu | Thr<br>955 | Leu | Ala | Ile | Ser | Val<br>960 |
| Asn | Phe | Trp | Val | Pro<br>965 | Ile | Leu | Leu | Asn | Gly<br>970 | Val | Ala | Val | Trp | Asp<br>975 | Val |
| Thr | Leu | Arg | Ser<br>980 | Pro | Ala | Gln | Gly | Val<br>985 | Ser | Cys | Val | Ser | Gln<br>990 | Arg | Glu |
| Pro | Pro | Gln | His<br>995 | Ser | Asp | Leu | Leu | Thr<br>1000 | Gln | Ile | Gln | Gly | Arg<br>1005 | Ser | Val |
| Leu | Asp | Cys | Ala<br>1010 | Ile | Ala | Asp | Cys | Leu<br>1015 | His | Leu | Arg | Cys | Asp<br>1020 | Ile | Pro |
| Ser | Leu | Gly | Thr<br>1025 | Leu | Asp | Glu | Leu | Asp<br>1030 | Phe | Ile | Leu | Lys<br>1035 | Gly | Asn | Leu<br>1040 |
| Ser | Phe | Gly | Trp | Ile<br>1045 | Ser | Gln | Thr | Leu | Gln<br>1050 | Lys | Lys | Val | Leu | Leu<br>1055 | Leu |

|   |   |   |   |   |   |   |   |   |   |   |   |   |   |   |
|---|---|---|---|---|---|---|---|---|---|---|---|---|---|---|
|Ser|Glu|Ala|Glu 1060|Ile|Thr|Phe|Asn|Ser 1065|Val|Tyr|Ser|Gln 1070|Leu|Pro|
|Gly|Gln|Glu 1075|Ala|Phe|Leu|Arg|Ala 1080|Gln|Val|Ser|Thr|Met 1085|Leu|Glu|Glu|
|Tyr|Val 1090|Val|Tyr|Glu|Pro|Val 1095|Phe|Leu|Met|Val|Phe 1100|Ser|Ser|Val|Gly|
|Gly 1105|Leu|Leu|Leu|Leu|Ala 1110|Leu|Ile|Thr|Val|Ala 1115|Leu|Tyr|Lys|Leu|Gly 1120|
|Phe|Phe|Lys|Arg|Gln 1125|Tyr|Lys|Glu|Met|Leu 1130|Asp|Leu|Pro|Ser|Ala 1135|Asp|
|Pro|Asp|Pro|Ala 1140|Gly|Gln|Ala|Asp|Ser 1145|Asn|His|Glu|Thr|Pro 1150|Pro|His|
|Leu|Thr|Ser 1155|

(2) INFORMATION FOR SEQ ID NO:47:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

AGTTACGGAT CCGGCACCAT GACCTTCGGC ACTGTGATCC TCCTGTGTG        49

(2) INFORMATION FOR SEQ ID NO:48:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

GCTGGACGAT GGCATCCAC        19

(2) INFORMATION FOR SEQ ID NO:49:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

GTAGAGTTAC GGATCCGGCA CCAT        24

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:50:

GCAGCCAGCT TCGGACAGAC                                                        20

( 2 ) INFORMATION FOR SEQ ID NO:51:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:51:

CCATGTCCAC AGAACAGAGA G                                                      21